US009926601B2

(12) United States Patent
Gertler et al.

(10) Patent No.: US 9,926,601 B2
(45) Date of Patent: Mar. 27, 2018

(54) ALTERNATIVELY SPLICED MRNA ISOFORMS AS PROGNOSTIC INDICATORS FOR METASTATIC CANCER

(75) Inventors: Frank B. Gertler, Boston, MA (US); Christopher Boyce Burge, Belmont, MA (US); Irina M. Shapiro, Chestnut Hill, MA (US); Wu Albert Cheng, Somerville, MA (US); John S. Condeelis, Bronx, NY (US); Maja H. Oktay, Rye, NY (US)

(73) Assignees: Massachusetts Institute of Technology, Cambridge, MA (US); Montefiore Medical Center, Bronx, NY (US); Albert Einstein College of Medicine, Inc., Bronx, NY (US)

( * ) Notice: Subject to any disclaimer, the term of this patent is extended or adjusted under 35 U.S.C. 154(b) by 625 days.

(21) Appl. No.: 14/000,995

(22) PCT Filed: Feb. 24, 2012

(86) PCT No.: PCT/US2012/026424
§ 371 (c)(1),
(2), (4) Date: Nov. 4, 2013

(87) PCT Pub. No.: WO2012/116248
PCT Pub. Date: Aug. 30, 2012

(65) Prior Publication Data
US 2014/0066319 A1 Mar. 6, 2014

Related U.S. Application Data

(60) Provisional application No. 61/446,162, filed on Feb. 24, 2011, provisional application No. 61/498,387, filed on Jun. 17, 2011.

(51) Int. Cl.
C12Q 1/68 (2006.01)
G01N 33/574 (2006.01)
G01N 33/50 (2006.01)
G01N 33/53 (2006.01)

(52) U.S. Cl.
CPC ..... *C12Q 1/6886* (2013.01); *G01N 33/57415* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

2003/0219805 A1 11/2003 Kelman et al.
2004/0115686 A1 6/2004 Dolginow et al.
2009/0311694 A1 12/2009 Gallagher et al.
2011/0177967 A1 7/2011 Carstens et al.

FOREIGN PATENT DOCUMENTS

WO 2010077288 A2 7/2010

OTHER PUBLICATIONS

PCT International Search Report dated May 31, 2012 in connection with PCT International Patent Application No. PCT/US2012/026424, 5 pages.
PCT Written Opinion of the International Searching Authority dated May 31, 2012 in connection with PCT International Patent Application No. PCT/US2012/026424, 7 pages.
The Supplementary European Search Report dated Jun. 15, 2015 for Application No. EP 12749944.0.
Bemmo et al. "Exon-level transcriptome profiling in murine breast cancer reveals splicing changes specific to tumore with different metastatic abilities." Plos One, vol. 5, No. 8, Aug. 6, 2010, e11981.
David et al. "Alternative pre-mRNA splicing regulation in cancer: pathways and programs unhinged." Genes & Development, vol. 24, No. 21, Nov. 1, 2010, pp. 2343-2364.
Srebrow et al. "The connection between splicing and cancer." Journal of Cell Science, vol. 119, No. 13, Jun. 6, 2006, pp. 2635-2641.
Kim et al. "Insights into the connection between cancer and alternative splicing." Trends in Genetics, vol. 24, No. 1, Dec. 3, 2007, pp. 7-10.
Abba MC, Drake JA, Hawkins KA, Hu Y, Sun H, et al. (2004) Transcriptomic changes in human breast cancer progression as determined by serial analysis of gene expression. Breast Cancer Res 6: R499-513.
Audic S, Claverie JM (1997) The significance of digital gene expression profiles. Genome Res 7: 986-995.
Balda MS, Whitney JA, Flores C, Gonzalez S, Cereijido M, et al. (1996) Functional dissociation of paracellular permeability and transepithelial electrical resistance and disruption of the apical-basolateral intramembrane diffusion barrier by expression of a mutant tight junction membrane protein. J Cell Biol 134: 1031-1049.
Bear JE, Loureiro JJ, Libova I, Fassler R, Wehland J, et al. (2000) Negative regulation of fibroblast motility by Ena/VASP proteins. Cell 101: 717-728.
Benjamini Y, Hochberg Y (1995) Controlling the false discovery rate: a practical and powerful approach to multiple testing. Journal of the Royal Statistical Society Series B (Methodological): 289-300.
Blencowe BJ (2006) Alternative splicing: new insights from global analyses. Cell 126: 37-47.
Blick T, Widodo E, Hugo H, Waltham M, Lenburg ME, et al. (2008) Epithelial mesenchymal transition traits in human breast cancer cell lines. Clin Exp Metastasis 25: 629-642.

(Continued)

*Primary Examiner* — Nancy J Leith
(74) *Attorney, Agent, or Firm* — Bryan D. Zerhusen; Locke Lord LLP

(57) ABSTRACT

The present invention provides a method for identifying a tumor as likely to metastasize, or likely to have metastasized, comprising obtaining a sample of the tumor and quantitating alternatively spliced mRNA isoforms of a cell motility gene, a cell adhesion gene and/or an actin cytoskeletal remodeling gene in the sample, or any specified genes or the level of RNA binding proteins compared to a predetermined non-metastasizing control.

10 Claims, 16 Drawing Sheets

(56) References Cited

OTHER PUBLICATIONS

Bolos V, Peinado H, Perez-Moreno MA, Fraga MF, Esteller M, et al. (2003) The transcription factor Slug represses E-cadherin expression and induces epithelial to mesenchymal transitions: a comparison with Snail and E47 repressors. J Cell Sci 116:499511.
Borjesson PK, Postema EJ, Roos JC, Colnot DR, Manes HA, et al. (2003) Phase I therapy study with (186)Re-labeled humanized monoclonal antibody BIWA 4 (bivatuzumab) in patients with head and neck squamous cell carcinoma. Clin Cancer Res 9: 3961S-3972S.
Chikumi H, Barac A, Behbahani B, Gao Y, Teramoto H, et al. (2004) Homo- and heterooligomerization of PDZ-RhoGEF, Larg and p115RhoGEF by their C-tetininal region regulates their in vivo Rho GEF activity and transfoiming potential. Oncogene 23: 233-240.
Christiansen JJ, Rajasekaran AK (2006) Reassessing epithelial to mesenchymal transition as a prerequisite for carcinoma invasion and metastasis. Cancer Res 66: 8319-8326.
Christofori G (2006) New signals from the invasive front. Nature 441: 444-450.
Comijn J, Berx G, Vermassen P, Verschueren K, van Grunsven L, et al. (2001) The twohanded E box binding zinc finger protein SIP1 downregulates E-cadherin and induces invasion. Mol Cell 7: 1267-1278.
Condeelis J, Pollard JW (2006) Macrophages: obligate partners for tumor cell migration, invasion, and metastasis. Cell 124: 263-266.
de Hoon M, Imoto S, Nolan J, Miyano S (2004) Open source clustering software. Bioinformatics 20: 14531454.
Dennis Jr G, Sherman B, Hosack D, Yang J, Gao W, et al. (2003) David: database for annotation, visualization, and integrated discovery. Genome Biol 4: P3.
Elenbaas B, Spirio L, Koerner F, Fleming MD, Zimonjic DB, et al. (2001) Human breast cancer cells generated by oncogenic transformation of primary mammary epithelial cells. Genes Dev 15: 50-65.
Ewald AJ, Brenot A, Duong M, Chan BS, Werb Z (2008) Collective epithelial migration and cell rearrangements drive mammary branching morphogenesis. Dev Cell 14: 570-581.
Gertler FB, Niebuhr K, Reinhard M, Wehland J, Soriano P (1996) Mena, a relative of VASP and Drosophila Enabled, is implicated in the control of microfilament dynamics. Cell 87: 227-239.
Huang, Da Wei, et al., (2008) Systematic and integrative analysis of large gene lists using David bioinformatics resources, Nature Protocols, vol. 4, No. 1, Dec 18, 2008, pp. 44-57.
Hugo H, Ackland ML, Buick T, Lawrence MG, Clements JA, et al. (2007) Epithelial—mesenchymal and mesenchymal—epithelial transitions in carcinoma progression. J Cell Physiol 213: 374-383.
Joslin EJ, Opresko LK, Wells A, Wiley HS, Lauffenburger DA (2007) EGF—receptor mediated mammary epithelial cell migration is driven by sustained ERK signaling from autocrine stimulation. J Cell Sci 120: 3688-3699.
Keirsebilck A, Bonne S, Staes K, van Hengel J, Nollet F, et al. (1998) Molecular cloning of the human p120ctn catenin gene (CTNND1): expression of multiple alternatively spliced isofoinis. Genomics 50: 129146.
Kim HD, Guo TW, Wu AP, Wells A, Gertler FB, et al. (2008) Epidermal growth factor-induced enhancement of glioblastoma cell migration in 3D arises from an intrinsic increase in speed but an extrinsic matrix—and proteolysis—dependent increase in persistence. Mol Biol Cell 19: 4249-4259.
LaGamba D, Nawshad A, Hay Ed (2005) Microarray analysis of gene expression during epithelial—mesenchymal transformation. Dev Dyn 234: 132-142.
Lapuk A, Man H, Jakkula L, Pedro H, Bhattacharya S, et al. Exon—level microarray analyses identify alternative splicing programs in breast cancer. Mol Cancer Res 8: 961-974. Jul. 6, 2010.
Li H, Ruan J, Durbin R (2008) Mapping short DNA sequencing reads and calling variants using mapping quality scores. Genome research 18: 1851.
Lin X, Miller JW, Mankodi A, Kanadia RN, Yuan Y, et al. (2006) Failure of MBNL1-dependent post-natal splicing transitions in myotonic dystrophy. Hum Mol Genet 15:2087-2097.

Mani SA, Guo W, Liao MA, Eaton EA, Ayyanan A, et al. (2008) The epithelial-mesenchymal transition generates cells with properties of stem cells. Cell 133: 704-715.
Mani SA, Yang J, Brooks M, Schwaninger G, Zhou A, et al. (2007) Mesenchyme Forkhead 1 (FOXC2) plays a key role in metastasis and is associated with aggressive basal-like breast cancers. Proc Natl Acad Sci U S A 104: 10069-10074.
Medici D, Hay ED, Olsen BR (2008) Snail and Slug promote epithelial-mesenchymal transition through beta-catenin-T-cell factor-4-dependent expression of transforming growth factor-beta3. Mol Biol Cell 19: 4875-4887.
Mon M, Nakagami H, Koibuchi N, Miura K, Takami Y, et al. (2009) Zyxin mediates actin fiber reorganization in epithelial-mesenchymal transition and contributes to endocardial morphogenesis. Mol Biol Cell 20: 3115-3124.
Mortazavi A, Williams BA, McCue K, Schaeffer L, Wold B (2008) Mapping and quantifying mammalian transcriptomes by RNA-Seq. Nat Methods 5: 621-628.
Nelson WJ (2008) Regulation of cell-cell adhesion by the cadherin-catenin complex. Biochem Soc Trans 36: 149-155.
Pajares MJ, Ezponda T, Catena R, Calvo A, Pio R, et al. (2007) Alternative splicing: an emerging topic in molecular and clinical oncology. Lancet Oncol 8: 349-357.
Philippar U, Roussos ET, Oser M, Yamaguchi H, Kim HD, et al. (2008) A Mena invasion isoform potentiates EGF-induced carcinoma cell invasion and metastasis. Dev Cell 15: 813-828.
Phua DC, Humbert PO, Hunziker W (2009) Vimentin regulates scribble activity by protecting it from proteasomal degradation. Mol Biol Cell 20: 2841-2855.
Pino MS, Balsamo M, Di Modugno F, Mottolese M, Alessio M, et al. (2008) Human Mena+11a isoform serves as a marker of epithelial phenotype and sensitivity to epidernial growth factor receptor inhibition in human pancreatic cancer cell lines. Clin Cancer Res 14: 4943-4950.
Pruitt K, Tatusova T, Maglott D (2006) NCBI reference sequences (RefSeq): a curated non-redundant sequence database of genomes, transcripts and proteins. Nucleic acids research, Nucleic Acids Research, vol. 35, Database issue D61-D65, published Nov. 27, 2006.
Qin Y, Capaldo C, Gumbiner BM, Macara IH (2005) The mammalian Scribble polarity protein regulates epithelial cell adhesion and migration through E-cadherin. J Cell Biol 171: 1061-1071.
Riaz M, Elstrodt F, Hollestelle A, Dehghan A, Klijn JG, et al. (2009) Low-risk susceptibility alleles in 40 human breast cancer cell lines. BMC Cancer 9: 236.
Robinson MD, Oshlack A A scaling normalization method for differential expression analysis of RNA-seq data. Genome Biol 11: R25, pp. 1-9, Mar. 2, 2010.
Rubin MA, Putzi M, Mucci N, Smith DC, Wojno K, et al. (2000) Rapid ("warm") autopsy study for procurement of metastatic prostate cancer. Clin Cancer Res 6: 1038-1045.
Saldanha A (2004) Java Treeview—extensible visualization of microarray data. Bioinforniatics vol. 20, Issue 17, 3246-3248.
Sanford J, Wang X, Mort M, VanDuyn N, Cooper D, et al. (2009) Splicing factor SFRS1 recognizes a functionally diverse landscape of RNA transcripts. Genome research 19: 381.
Savagner P, Valles AM, Jouanneau J, Yamada KM, Thiery JP (1994) Alternative splicing in fibroblast growth factor receptor 2 is associated with induced epithelial-mesenchymal transition in rat bladder carcinoma cells. Mol Biol Cell 5: 851-862.
Shang Y, Hu X, DiRenzo J, Lazar Ma, Brown M (2000) Cofactor dynamics and sufficiency in estrogen receptor-regulated transcription. Cell 103: 843-852.
Sorlie T, Perou Cm, Tibshirani R, Aas T, Geisler S, et al. (2001) Gene expression patterns of breast carcinomas distinguish tumor subclasses with clinical implications. Proc Natl Acad Sci U S A 98: 1086910874.
Srebrow A, Kornblihtt AR (2006) The connection between splicing and cancer. J Cell Sci 119: 2635-2641.

(56) References Cited

OTHER PUBLICATIONS

Taube JH, Herschkowitz JI, Komurov K, Zhou AY, Gupta S, et al. Core epithelial-to mesenchymal transition interactome gene-expression signature is associated with claudinlow and metaplastic breast cancer subtypes. Proc Natl Acad Sci U S A 107: 15449-15454. Aug. 31, 2010.
Terenzi F, Ladd AN Conserved developmental alternative splicing of muscle blind-like (MBNL) transcripts regulates MBNL localization and activity. RNA Biol 7: 43-55. Jan. 1, 2010.
Thierry-Mieg D, Thierry-Mieg J (2006) AceView: a comprehensive cDNA-supported gene and transcripts annotation. Genome Biol 7 Suppl 1: S12 1-14.
Thisse B, el Messal M, Perrin-Schmitt F (1987) The twist gene: isolation of a Drosophila zygotic gene necessary for the establishment of dorsoventral pattern. Nucleic Acids Res 15: 3439-3453.
Thompson EW, Newgreen DF, Tarin D (2005) Carcinoma invasion and metastasis: a role for epithelial-mesenchymal transition? Cancer Res 65: 5991-5995; discussion 5995.
Troxell ML, Gopalakrishnan S, McCormack J, Poteat BA, Pennington J, et al. (2000) Inhibiting cadherin function by dominant mutant E-cadherin expression increases the extent of tight junction assembly. J Cell Sci 113 (Pt 6):985-996.
van 't Veer LJ, Dai H, van de Vijver MJ, He YD, Hart AA, et al. (2002) Gene expression profiling predicts clinical outcome of breast cancer. Nature 415: 530-536.
Venables JP, Klinck R, Bramard A, Inkel L, Dufresne-Martin G, et al. (2008) Identification of alternative splicing markers for breast cancer. Cancer Res 68: 9525-9531.
Venables JP, Klinck R, Koh C, Gervais-Bird J, Bramard A, et al. (2009) Cancer-associated regulation of alternative splicing. Nat Struct Mol Biol 16: 670-676.
Vincent-Salomon A, Thiery JP (2003) Host microenvironment in breast cancer development: epithelial-mesenchymal transition in breast cancer development. Breast Cancer Res 5: 101-106.
Vitorino P, Meyer T (2008) Modular control of endothelial sheet migration. Genes Dev 22:3268-3281.
Vuolo M, Suhrland MJ, Madan R, Oktay MH (2009) Discrepant cytologic and radiographic findings in adjacent galactocele and fibroadenoma: a case report. Acta Cytol 53: 211-214.
Wang ET, Sandberg R, Luo S, Khrebtukova I, Zhang L, et al. (2008) Alternative isofonn regulation in human tissue transcriptomes. Nature 456: 470-476.
Warzecha CC, Jiang P, Amirikian K, Dittmar KA, Lu H, et al. An ESRP-regulated splicing programme is abrogated during the epithelial-mesenchymal transition. Embo J., 2010, vol. 29, No. 19, pp. 3289-3300.
Warzecha CC, Sato TK, Nabet B, Hogenesch JB, Carstens RP (2009) ESRP1 and ESRP2 are epithelial cell-type-specific regulators of FGFR2 splicing. Mol Cell 33: 591-601.
Warzecha CC, Shen S, Xing Y, Carstens RP (2009) The epithelial splicing factors ESRP1 and ESRP2 positively and negatively regulate diverse types of alternative splicing events. RNA Biol 6: 546-562.
Weigelt B, Peterse JL, van 't Veer LJ (2005) Breast cancer metastasis: markers and models. Nat Rev Cancer 5: 591-602.
Xue Y, Zhou Y, Wu T, Zhu T, Ji X, et al. (2009) Genome-wide Analysis of PTB-RNA Interactions Reveals a Strategy Used by the General Splicing Repressor to Modulate Exon Inclusion or Skipping. Molecular cell 36: 99-1006.
Yang J, Mani SA, Donaher JL, Ramaswamy S, Itzykson RA, et al. (2004) Twist, a master regulator of morphogenesis, plays an essential role in tumor metastasis. Cell 117: 927-939.
Yang J, Weinberg RA (2008) Epithelial-mesenchymal transition: at the crossroads of development and tumor metastasis. Dev Cell 14: 818-829.
Yeo GW, Coufal NG, Liang TY, Peng GE, Fu XD, et al. (2009) An RNA code for the FOX2 splicing regulator revealed by mapping RNA-protein interactions in stem cells. Nat Struct Mol Biol 16: 130-137.
Yilmaz M, Christofori G (2009) EMT, the cytoskeleton, and cancer cell invasion. Cancer Metastasis Rev 28:15-33.
Yoneda T, Williams PJ, Hiraga T, Niewolna M, Nishimura R (2001) A bone-seeking clone exhibits different biological properties from the MDA-MB-231 parental human breast cancer cells and a brain-seeking clone in vivo and in vitro. J Bone Miner Res 16: 1486-1495.

ion is a U.S. national stage entry under 35
ALTERNATIVELY SPLICED MRNA ISOFORMS AS PROGNOSTIC INDICATORS FOR METASTATIC CANCER

CROSS-REFERENCE TO RELATED APPLICATIONS

This applicat
U.S.C. § 371 of PCT International Patent Application No. PCT/US2012/026424, filed Feb. 24, 2012, which claims benefit of U.S. Provisional Application No. 61/498,387, filed Jun. 17, 2011 and U.S. Provisional Application No. 61/446,162, filed Feb. 24, 2011, the contents of each of which are incorporated herein by reference into the subject application.

STATEMENT OF GOVERNMENT SUPPORT

This invention was made with government support under grant numbers CA112967, CA113395, CA100324, and RO1 HG002439 awarded by the National Institutes of Health, U.S. Department of Health and Human Services. The government has certain rights in the invention.

FIELD OF THE INVENTION

The present invention relates generally to methods of assessing the metastatic potential of a tumor.

BACKGROUND OF THE INVENTION

The ".txt" Sequence Listing filed with this application by EFS and which is entitled 54887_0006_ST25.txt, is 7 kilobytes in size and which was created on Jan. 30, 2012 is hereby incorporated by reference.

Throughout this application various publications are referred to in brackets. Full citations for these references may be found at the end of the specification. The disclosures of these publications, and of all patents, patent application publications and books referred to herein, are hereby incorporated by reference in their entirety into the subject application to more fully describe the art to which the subject invention pertains.

Breast cancer is one of the most common malignant diseases in the United States: 1 in 8 women are diagnosed with breast cancer during their lifetime (NIH website, breast cancer statistics). The main cause of death for breast cancer patients arises from dissemination of the primary tumor by metastases to other organs, a process that may only manifest as long as 10 or more years after initial diagnosis [1].

Currently established clinical prognostic criteria, including the histopathologic grade of the tumor, tumor size, the presence of the lymph node metastasis and hormone receptor status, can predict systemic metastatic potential in only a subgroup of patients with breast cancer. Microarray gene expression platforms, such as the MammaPrint™ 70 gene signature, are emerging as predictors of distant metastasis [1,2] but lack broad applicability [1] and offer relatively limited predictive power [3]. Therefore, novel prognostic markers are needed to identify patients with the high risk of developing metastasis to drive clinical treatment decisions.

About 90% of human malignancies are carcinomas, tumors of epithelial origin [4]. The early steps in carcinoma metastasis often bear a striking resemblance to developmental programs involving Epithelial-to-Mesenchymal Transition (EMT), a process that converts polarized organized epithelial cells into isolated, migratory cells with a mesenchymal morphology [5]. A growing body of work implicates EMT-like mechanisms in tumor cell invasion and dissemination in experimental systems, and recently, in human cancer [6,7]. Normal epithelia are comprised of cells with aligned apical-basal polarity that are interconnected laterally by several types of junctions including adherens junctions (AJs), which play important roles in establishing and regulating cell-cell adhesion [8]. E-cadherin, the major component of epithelial AJs, is a homophilic transmembrane protein that engages E-cadherin molecules on neighboring cells, and loss of functional E-cadherin is a hallmark of EMT. During EMT, apico-basolateral polarity is lost, cell-cell junctions dissolve and the actin cytoskeleton is remodeled to endow cells with mesenchymal characteristics including an elongated, migratory and invasive phenotype.

Importantly, as a consequence of EMT, cells may escape the tumor, invade the surrounding tissue and migrate towards blood vessels or lymphatic vessels guided by the cells and extracellular matrix present in their microenvironment [9]. Thus, EMT, a mechanism important for embryonic development, plays a critical role during malignant transformation.

While much is known regarding the regulation of EMT at the transcriptional level, alternative splicing of several genes has also been correlated with EMT progression. The extent of splicing changes and their contributions to the morphological conversion accompanying EMT have not been extensively investigated.

The molecular mechanisms underlying EMT have been studied extensively in the last decade. EMT-inducing growth factors can trigger signaling cascades that activate a network of transcription factors, such as ZEB-1, Goosecoid, FOXC2 and Twist [17], that orchestrate the EMT program; ectopic expression of a number of the EMT-associated transcription factors can initiate the program as well. Twist, a potent EMT driver, was identified originally as an inducer of mesoderm formation in Drosophila [18]. Ectopic Twist expression in epithelial cells results in loss of E-cadherin-mediated cell-cell adhesion, acquisition of mesenchymal markers and increased motility of isolated cells [19], a hallmark of the mesenchymal phenotype. E-cadherin expression is suppressed by several EMT-inducing transcription factors [20, 21], while some mesenchymal markers are activated directly by this same repertoire of factors.

The control of EMT is likely also subject to regulation at post-transcriptional levels such as alternative pre-mRNA splicing. Alternative splicing expands the diversity of the proteome by producing multiple mRNA isoforms from each gene [22]. More than 90% of human genes are estimated to undergo alternative splicing, with a majority of alternative splicing events exhibiting tissue-specific splicing differences [23]. A variety of cancer-associated genes express alternatively spliced isoforms [24], indicating that regulation at the level of splicing may play important roles in cancer onset and progression. Alternative splicing of FGFR2 correlates with EMT in rat bladder carcinoma cells, where mutually exclusive inclusion of one of two exons defines the ligand binding specificity of the receptor during EMT [25]. ENAH (also known as Mena), an actin cytoskeleton regulatory protein, contains a small coding exon 11a that is included exclusively within epithelial cells and is excluded in mesenchymal cell lines and during EMT [26,27]. Alternative splicing of p120catenin (CTNND1) generates protein isoforms that display opposite effects on cell motility in epithelial and mesenchymal cells [28].

Recently, two epithelial-specific RNA binding proteins, ESRP1 and ESRP2, homologs of the nematode splicing factor Sym-2, were identified in a screen for FGFR2 splicing regulators [27]. REFOX2 (formerly "Fox2") splicing factor has been recently demonstrated to regulate subtype-specific splicing in a panel of breast cancer cell lines [29]. The ESRPs and RBFOX2 promote epithelial splicing of a number of transcripts including FGFR2 and ENAH, some of which play important roles in EMT [27,30]. Loss of ESRPs in epithelial cells promotes EMT-like changes in cell morphology [31]. However, the full extent of alternative splicing during EMT and its functional consequences to cell phenotype has yet to be elucidated.

The present invention has identified signatures of multi-exon genes that undergo alternative splicing during EMT and are predictive of metastasis.

SUMMARY OF THE INVENTION

A method is provided for identifying a tumor in a subject as likely to metastasize, or likely to have metastasized already, comprising:
treating a sample of the tumor obtained from the subject so as to permit determination of mRNA levels or determination of gene expression product levels in the sample;
determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:
CD44, NUMB, FAM62B, SLK, ENAH, H2AFY, and OSBPL8, and/or SCRIB, CLSTN1, MLPH, and TXNDC14 and/or CTNND1;
wherein determination of a proportion of (1) alternatively spliced mRNA isoforms, or (2) alternatively spliced gene expression products, respectively, for each of CD44, NUMB, FAM62B, SLK, ENAH, H2AFY, and OSBPL8, equal to, or greater than, a control proportion indicates that the tumor is not likely to metastasize or is not likely to have metastasized already,
and wherein determination of a proportion of (1) alternatively spliced mRNA isoforms, or (2) alternatively spliced gene expression products, respectively, for each of SCRIB, CLSTN1, MLPH, and TXNDC14 and/or CTNND1 equal to, or greater than, a control proportion indicates that the tumor is likely to metastasize or is likely to have metastasized already.

Also provided is a method for identifying a tumor in a subject as likely to metastasize, or likely to have metastasized already, comprising:
treating a sample of the tumor obtained from the subject so as to permit determination of mRNA levels or gene expression product levels in the sample;
determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:
CD44, NUMB, FAM62B, SLK, ENAH, H2AFY, OSBPL8, C17orf61/PLSCR3, STARD10/CENTD2, MAP3K7, BMP1, and BTG3, and/or
YWHAB, ILF3, PAM, SCRIB, CLSTN1, MLPH, and TXNDC14/CTNND1;
wherein determination of a proportion of (1) alternatively spliced mRNA isoforms, or (2) alternatively spliced gene expression products, respectively, for each of CD44, NUMB, FAM62B, SLK, ENAH, H2AFY, OSBPL8, C17orf61/PLSCR3, STARD10/CENTD2, MAP3K7, BMP1, and BTG3, equal to, or greater than, a control proportion indicates that the tumor is not likely to metastasize or is not likely to have metastasized already,
and wherein determination of a proportion of (1) alternatively spliced mRNA isoforms, or (2) alternatively spliced gene expression products, respectively, for each of YWHAB, ILF3, PAM, SCRIB, CLSTN1, MLPH, and TXNDC14 and/or CTNND1 equal to, or greater than, a control proportion indicates that the tumor is likely to metastasize or is likely to have metastasized already.

Also provided is a method for identifying a tumor in a subject as likely to metastasize, or likely to have metastasized already, comprising:
treating a sample of the tumor obtained from the subject so as to permit determination of mRNA levels or determination of gene expression product levels in the sample;
determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:
ENAH, SLC37A2, MBNL1 and FLNB and/or MLPH and ARHGEF11;
wherein determination of a proportion of (1) alternatively spliced mRNA isoforms, or (2) alternatively spliced gene expression products, respectively, for each of ENAH, SLC37A2, MBNL1 and FLNB
equal to, or greater than, a control proportion indicates that the tumor is not likely to metastasize or is not likely to have metastasized already,
and wherein determination of a proportion of (1) alternatively spliced mRNA isoforms, or (2) alternatively spliced gene expression products, respectively, for each of MLPH and ARHGEF11 equal to, or greater than, a control proportion indicates that the tumor is likely to metastasize or is likely to have metastasized already.

Also provide is a method for identifying a tumor as likely to metastasize via lymph nodes in a subject, or likely to have metastasized via lymph nodes in a subject, comprising obtaining a sample of the tumor and determining if an alternatively spliced skipped exon mRNA isoform for SLC37A2 gene is present in the sample, wherein the absence of an alternatively spliced skipped exon mRNA isoform for SLC37A2 gene present in the sample, or a reduced level of an alternatively spliced skipped exon mRNA isoform for SLC37A2 gene present in the sample as compared to a non-metastatic control sample, indicates that the tumor is likely to metastasize via lymph nodes in the subject, or has likely metastasized via lymph nodes in the subject.

Also provided is a method for identifying an agent for inhibiting metastasis of a cancer comprising: a) obtaining a sample of the cancer; b) quantitating alternatively spliced mRNA isoforms of a cell motility gene, a cell adhesion gene and/or an actin cytoskeletal remodeling gene in the cancer or any of the genes exhibiting positive M-E.deltaPsi values in inc/excBound column of Table 5 in the absence of the agent; c) contacting the sample with the agent under conditions permitting gene transcription; and d) quantitating the alternatively spliced mRNA isoforms of the cell motility gene, cell adhesion gene and/or actin cytoskeletal remodeling gene in the sample in the presence of the agent, wherein a reduction in the amount of alternatively spliced mRNA isoforms of the cell motility gene, cell adhesion gene and/or the actin cytoskeletal remodeling gene in the presence of the agent compared to in the absence of the agent indicates that the agent inhibits metastasis of a cancer.

Also provided is a method for identifying an agent for inhibiting metastasis of a cancer comprising: a) obtaining a sample of the cancer; b) quantitating RNA binding proteins levels for one or more RNA binding proteins set forth hereinbelow; c) contacting the sample with the agent; and d) quantitating RNA binding proteins levels for one or more RNA binding proteins set forth hereinbelow in the sample in the presence of the agent, wherein a fold change of at least 1.5× either up or down in the sample in the presence of the agent compared to predetermined control RNA binding proteins levels indicates that the agent inhibits metastasis of a cancer.

Also provided is a method of inhibiting metastasis of a tumor in a subject comprising administering to the subject an agent which (i) inactivates or reduces expression of one or more genes having a negative M-E.deltaPsi value in M-E.deltaPsi Column of Table 5 or (ii) inactivates or reduces activity of an alternatively spliced exon gene expression product of one or more genes having a negative M-E.deltaPsi Column of Table-5.

Also provided is a method of inhibiting metastasis of a tumor in a subject comprising administering to the subject an agent which (i) activates or increases expression of one or more genes having a positive M-E.deltaPsi Column of Table 5 or (ii) activates or increases activity of an alternatively spliced exon gene expression product of one or more genes having a negative M-E.deltaPsi Column of Table 5.

Also provided is a method of determining a treatment type for a patient having a tumor comprising determining in a sample of the tumor the proportion of (1) alternatively spliced mRNA isoforms of one or more genes having a positive M-E.deltaPsi Column of Table 5 relative to the total mRNA isoforms of the one or more genes having a positive M-E.deltaPsi value in M-E.deltaPsi Column of Table 5 in the sample or (2) the proportion of alternatively spliced gene expression products of one or more genes having a positive M-E.deltaPsi Column of Table 9 relative to the total gene expression products of the one or more genes having a positive M-E.deltaPsi Column of Table 5 in the sample, wherein determination of a proportion of (1) alternatively spliced mRNA isoforms, or (2) alternatively spliced gene expression products, respectively, for the one or more genes equal to, or greater than, that of a control proportion indicates that the patient should be treated with one or more chemotherapeutic anti-tumor agents,
and wherein determination of a proportion of alternatively spliced mRNA isoforms, or alternatively spliced gene expression products, respectively, for the one or more genes less than that of a control proportion indicates that the patient should be treated with one or more non-chemotherapeutic anti-tumor agents.

Also provided is a product comprising an exon microarray which comprises a plurality of oligonucleotides having sequences corresponding to the sequences of the exons of the genes recited hereinabove.

Also provided is a product comprising an exon microarray which comprises a plurality of oligonucleotides having sequences corresponding to the sequences of exon:exon junctions found in the wildtype of the of the genes comprising the exons listed in inc/excBound Column of Table 5.

This inventions provides a method for identifying a tumor as likely to metastasize, or likely to have metastasized, comprising obtaining a sample of the tumor and quantitating alternatively spliced mRNA isoforms of a cell motility gene, a cell adhesion gene and/or an actin cytoskeletal remodeling gene in the sample, wherein an amount of alternatively spliced mRNA isoforms of the cell motility gene, cell adhesion gene and/or the actin cytoskeletal remodeling gene different to a predetermined control amount indicates that the tumor is likely to metastasize or is likely to have metastasized.

This invention provides a method for identifying a tumor as likely to metastasize via lymph nodes in a subject, or likely to have metastasized via lymph nodes in a subject, comprising obtaining a sample of the tumor and determining if an alternatively spliced skipped exon mRNA isoform for SLC37A2 gene is present in the sample, wherein the absence of an alternatively spliced skipped exon mRNA isoform for SLC37A2 gene present in the sample, or a reduced level of an alternatively spliced skipped exon mRNA isoform for SLC37A2 gene present in the sample as compared to a non-malignant control sample, indicates that the tumor is likely to metastasize via lymph nodes in the subject, or has likely metastasized via lymph nodes in the subject.

This invention provides a method for identifying an agent for inhibiting metastasis of a cancer comprising: a) obtaining a sample of the cancer; b) quantitating alternatively spliced mRNA isoforms of a cell motility gene, a cell adhesion gene and/or an actin cytoskeletal remodeling gene in the cancer; c) contacting the sample with the agent; and d) quantitating the alternatively spliced mRNA isoforms of the cell motility gene, cell adhesion gene and/or actin cytoskeletal remodeling gene in the sample, wherein a reduction in the amount of alternatively spliced mRNA isoforms of the cell motility gene, cell adhesion gene and/or the actin cytoskeletal remodeling gene in the presence of the agent indicates that the agent inhibits metastasis of a cancer.

In an embodiment of the invention, the methods reciting determining the proportion of alternatively spliced mRNA isoforms of the recited human genes relative to the total mRNA isoforms of said human genes can be employed, mutandis mutandis, by instead determining the proportion of alternatively spliced mRNA isoforms of the recited human genes relative to the amount of normally spliced mRNA isoforms of said human genes. In an embodiment, normally spliced mRNA isoforms means the most common mRNA transcript of the gene under non-cancerous and/or non-metastatic states in the subject or in subjects of the same species. In an embodiment of the invention, the methods reciting determining the proportion of alternatively spliced gene expression products of the recited human genes relative to the total amount of gene expression products of said human genes can be employed, mutandis mutandis, by instead determining the proportion of alternatively spliced gene expression products of the recited human genes relative to the amount of normally spliced gene expression products of said human genes. In an embodiment, normally spliced gene expression products means the most common gene expression product of the gene under non-cancerous and/or non-metastatic states in the subject or in subjects of the same species.

This invention provides a method for identifying an agent for inhibiting metastasis of a cancer comprising: a) obtaining a sample of the cancer; b) quantitating RNA binding proteins levels for one or more RNA binding proteins set forth hereinbelow; c) contacting the sample with the agent; and d) quantitating RNA binding proteins levels for one or more RNA binding proteins set forth hereinbelow in the sample in the presence of the agent, wherein a fold change of at least 1.5× either up or down in the sample in the presence of the agent compared to predetermined control RNA binding proteins levels indicates that the agent inhibits metastasis of a cancer.

DETAILED DESCRIPTION OF THE INVENTION

Figures 1A, 1B, 1C, 1D:
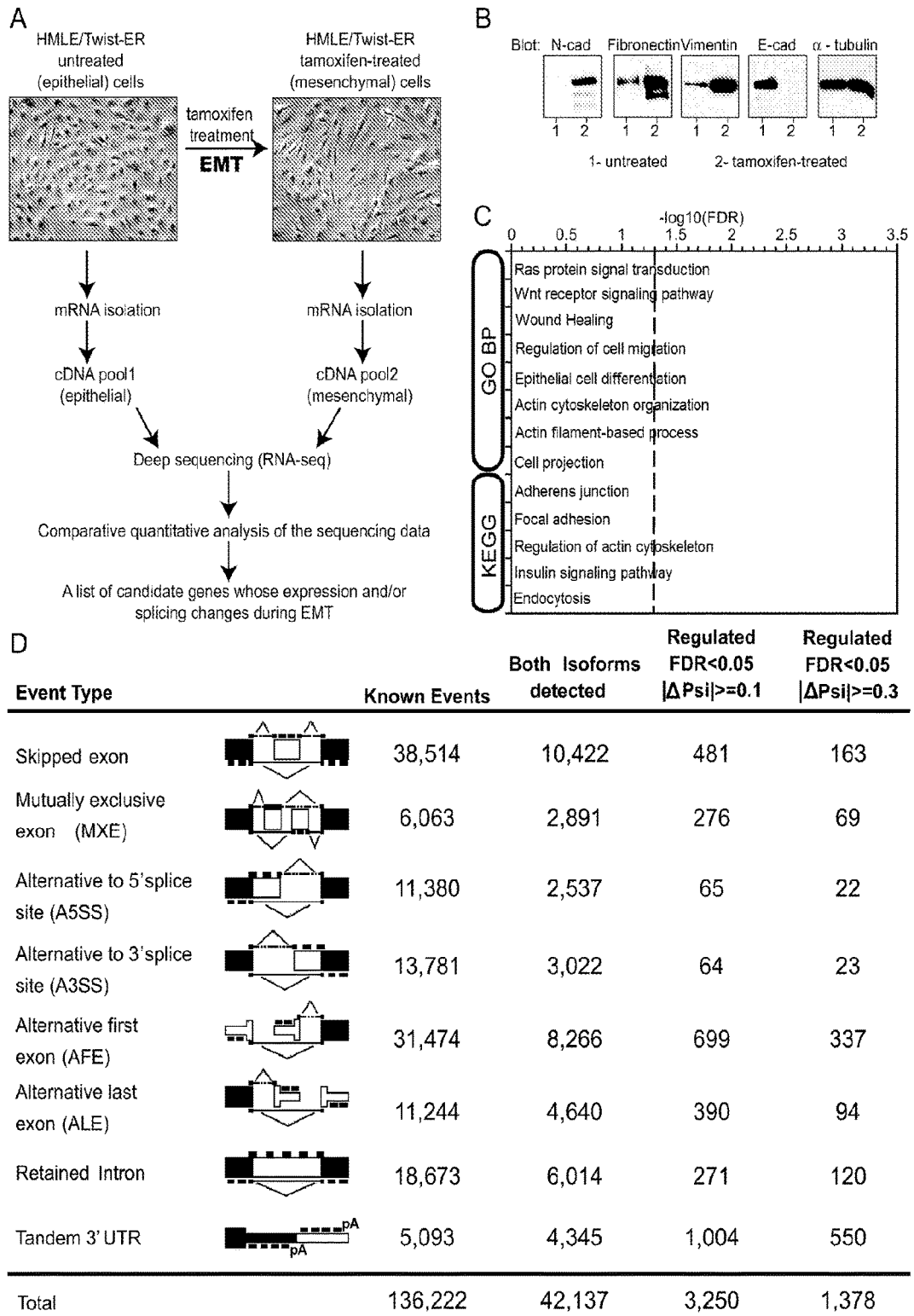
FIG. 1A-1D. Alternative mRNA isoform expression in EMT. (1A) Schematics of the in vitro EMT induction experiment Immortalized human mammary epithelial cells (HMLE) expressing Twist fused to Estrogen Receptor (ER) were induced to undergo EMT by addition of tamoxifen into the culture media. mRNA was collected before EMT induction (epithelial sample) and after EMT induction (mesenchymal sample). cDNA pools from both samples were deep sequenced (RNA-Seq) and analyzed (See Methods). (1B) Western blot analysis of N-cadherin, E-cadherin, fibronectin and vimentin expression with antibodies as indicated in cells lysates that were obtained before (1-untreated) and after (2-tamoxifen-treated) induction of EMT in HMLE/Twist-ER cells. α-tubulin was used as a loading control. (1C) Gene ontology enrichment analysis bar graph of changes in alternative splicing events with $|\Delta\Psi|>=10\%$ between samples. Gene ontology "biological process," GO_BP_FAT, annotation is indicated in light gray (upper) on the y axis. KEGG Pathway (www.genome.jp/kegg/) annotation is indicated in darker gray (lower) on y axis. Benjamini FDR (−log 10) is indicated on the x axis. Vertical dotted line marks Benjamini FDR=0.05. (D) Column 1 shows different kinds of splicing events that have been analyzed. Columns 2-5 show the number of events of each type: (2) all known events based on AceView annotation; (3) events with both isoforms supported by RNA-Seq reads; (4) events detected at a False Discovery Rate (FDR) of 5% with $\Delta\Psi>=10\%$ between samples; (5) events detected at an FDR of 5% with $\Delta\Psi>=30\%$ between samples.

A method is provided for identifying a tumor in a subject as likely to metastasize, or likely to have metastasized already, comprising:

treating a sample of the tumor obtained from the subject so as to permit determination of mRNA levels or determination of gene expression product levels in the sample;

determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:

CD44, NUMB, FAM62B, SLK, ENAH, H2AFY, and OSBPL8, and/or SCRIB, CLSTN1, MLPH, and TXNDC14 and/or CTNND1;

wherein determination of a proportion of (1) alternatively spliced mRNA isoforms, or (2) alternatively spliced gene expression products, respectively, for each of CD44, NUMB, FAM62B, SLK, ENAH, H2AFY, and OSBPL8, equal to, or greater than, a control proportion indicates that the tumor is not likely to metastasize or is not likely to have metastasized already, and wherein determination of a proportion of (1) alternatively spliced mRNA isoforms, or (2) alternatively spliced gene expression products, respectively, for each of SCRIB, CLSTN1, MLPH, and TXNDC14 and/or CTNND1 equal to, or greater than, a control proportion indicates that the tumor is likely to metastasize or is likely to have metastasized already.

Also provided is a method for identifying a tumor in a subject as likely to metastasize, or likely to have metastasized already, comprising:

treating a sample of the tumor obtained from the subject so as to permit determination of mRNA levels or gene expression product levels in the sample;

determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:
CD44, NUMB, FAM62B, SLK, ENAH, H2AFY, OSBPL8, C17orf61/PLSCR3, STARD10/CENTD2, MAP3K7, BMP1, and BTG3; and/or
YWHAB, ILF3, PAM, SCRIB, CLSTN1, MLPH, and TXNDC14 and/or CTNND1;
wherein determination of a proportion of (1) alternatively spliced mRNA isoforms, or (2) alternatively spliced gene expression products, respectively, for each of CD44, NUMB, FAM62B, SLK, ENAH, H2AFY, OSBPL8, C17orf61/PLSCR3, STARD10/CENTD2, MAP3K7, BMP1, and BTG3, equal to, or greater than, a control proportion indicates that the tumor is not likely to metastasize or is not likely to have metastasized already,
and wherein determination of a proportion of (1) alternatively spliced mRNA isoforms, or (2) alternatively spliced gene expression products, respectively, for each of YWHAB, ILF3, PAM, SCRIB, CLSTN1, MLPH, and TXNDC14 and/or CTNND1 equal to, or greater than, a control proportion indicates that the tumor is likely to metastasize or is likely to have metastasized already.

Also provided is a method for identifying a tumor in a subject as likely to metastasize, or likely to have metastasized already, comprising:
treating a sample of the tumor obtained from the subject so as to permit determination of mRNA levels or determination of gene expression product levels in the sample;
determining (1) the proportion of alternatively spliced mRNA isoforms of the following human genes relative to the total mRNA isoforms of the following human genes in the sample or (2) the proportion of alternatively spliced gene expression products of the following human genes relative to the total gene expression products of the following human genes in the sample:
ENAH, SLC37A2, MBNL1 and FLNB and/or MLPH and ARHGEF11;
wherein determination of a proportion of (1) alternatively spliced mRNA isoforms, or (2) alternatively spliced gene expression products, respectively, for each of ENAH, SLC37A2, MBNL1 and FLNB
equal to, or greater than, a control proportion indicates that the tumor is not likely to metastasize or is not likely to have metastasized already,
and wherein determination of a proportion of (1) alternatively spliced mRNA isoforms, or (2) alternatively spliced gene expression products, respectively, for each of MLPH and ARHGEF11 equal to, or greater than, a control proportion indicates that the tumor is likely to metastasize or is likely to have metastasized already.

In an embodiment, determining (1) the proportion of alternatively spliced mRNA isoforms of the human genes relative to the total mRNA isoforms of the human genes in the sample or (2) the proportion of alternatively spliced gene expression products of the human genes relative to the total gene expression products in the sample comprises determining the value of $\psi_{sample}$ for each human gene, wherein $\psi_{sample}$=(i) total number of alternative exon inclusion mRNA isoform reads in the sample/((total number of alternative exon inclusion mRNA isoform reads in the sample)+ (total number of alternative exon exclusion mRNA isoform reads in the sample)), or (ii) total number of alternative exon inclusion gene expression product reads in the sample/((total number of alternative exon inclusion gene expression product reads in the sample)+(total number of alternative exon exclusion gene expression product reads in the sample)), respectively,
wherein a level of $\Delta\psi$=−0.1 or less for each of CD44, NUMB, FAM62B, SLK, ENAH, H2AFY and OSBPL8, indicates that the tumor is not likely to metastasize or is not likely to have metastasized already,
and wherein a level of $\Delta\psi$=+0.1 or more for each of SCRIB, CLSTN1, MLPH, and TXNDC14 and/or CTNND1 indicates that the tumor is likely to metastasize or is likely to have metastasized already,
wherein $\Delta\psi=\psi_{sample}-\psi_{control}$, and wherein $\psi_{control}$=(i) total number of alternative exon inclusion mRNA isoform reads in a control/((total number of alternative exon inclusion mRNA isoform reads in the control)+(total number of alternative exon exclusion mRNA isoform reads in a control)), or (ii) total number of alternative exon inclusion gene expression product reads in a control/((total number of alternative exon inclusion gene expression product reads in the control)+(total number of alternative exon exclusion gene expression product reads in the control)), respectively.

In an embodiment, determining (1) the proportion of alternatively spliced mRNA isoforms of the human genes relative to the total mRNA isoforms of the human genes in the sample or (2) the proportion of alternatively spliced gene expression products of the human genes relative to the total gene expression products in the sample comprises determining the value of $\psi_{sample}$ for each human gene, wherein $\psi_{sample}$=(i) total number of alternative exon inclusion mRNA isoform reads in the sample/((total number of alternative exon inclusion mRNA isoform reads in the sample)+ (total number of alternative exon exclusion mRNA isoform reads in the sample)), or (ii) total number of alternative exon inclusion gene expression product reads in the sample/((total number of alternative exon inclusion gene expression product reads in the sample)+(total number of alternative exon exclusion gene expression product reads in the sample)), respectively,
wherein a level of $\Delta\psi$=−0.1 or less for each of CD44, NUMB, FAM62B, SLK, ENAH, H2AFY, OSBPL8, C17orf61/PLSCR3, STARD10/CENTD2, MAP3K7, BMP1, and BTG3 indicates that the tumor is not likely to metastasize or is not likely to have metastasized already,
and wherein a level of $\Delta\psi$=+0.1 or more for each of YWHAB, ILF3, PAM, SCRIB, CLSTN1, MLPH, and TXNDC14 and/or CTNND1 indicates that the tumor is likely to metastasize or is likely to have metastasized already,
wherein $\Delta\psi=\psi_{sample}-\psi_{control}$, and wherein $\psi_{control}$=(i) total number of alternative exon inclusion mRNA isoform reads in a control/((total number of alternative exon inclusion mRNA isoform reads in the control)+(total number of alternative exon exclusion mRNA isoform reads in a control)), or (ii) total number of alternative exon inclusion gene expression product reads in a control/((total number of alternative exon inclusion gene expression product reads in the control)+(total number of alternative exon exclusion gene expression product reads in the control)), respectively.

In an embodiment, determining (1) the proportion of alternatively spliced mRNA isoforms of the human genes relative to the total mRNA isoforms of the human genes in the sample or (2) the proportion of alternatively spliced gene expression products of the human genes relative to the total gene expression products in the sample comprises determining the value of $\psi_{sample}$ for each human gene, wherein $\psi_{sample}$=(i) total number of alternative exon inclusion mRNA isoform reads in the sample/((total number of alternative exon inclusion mRNA isoform reads in the sample)+ (total number of alternative exon exclusion mRNA isoform reads in the sample)), or (ii) total number of alternative exon inclusion gene expression product reads in the sample/((total number of alternative exon inclusion gene expression product reads in the sample)+(total number of alternative exon exclusion gene expression product reads in the sample)), respectively, wherein a level of $\Delta\psi=-0.1$ or less for each of ENAH, SLC37A2, MBNL1 and FLNB, indicates that the tumor is not likely to metastasize or is not likely to have metastasized already, and wherein a level of $\Delta\psi=+0.1$ or more for each of MLPH and ARHGEF11 indicates that the tumor is likely to metastasize or is likely to have metastasized already, wherein $\Delta\psi=\psi_{sample}-\psi_{control}$, and wherein $\psi_{control}$=total number of alternative exon inclusion mRNA isoform reads in a control/((total number of alternative exon inclusion mRNA isoform reads in the control)+(total number of alternative exon exclusion mRNA isoform reads in a control)), or (ii) total number of alternative exon inclusion gene expression product reads in a control/((total number of alternative exon inclusion gene expression product reads in the control)+(total number of alternative exon exclusion gene expression product reads in the control)), respectively.

In an embodiment, the sample is a breast cancer sample. In an embodiment, the tumor is an invasive duct carcinoma. In an embodiment, the sample is obtained by fine needle aspiration.

In an embodiment, the alternatively spliced mRNA isoforms or alternatively spliced gene expression products result from a skipped exon, a mutually exclusive exon, a retained intron, an alternative 5' splice site, an alternative 3' splice site, an alternative 3' UTR, an alternative first exon, and/or an alternative last exon.

In an embodiment, quantitating the alternatively spliced mRNA isoforms is effected indirectly by isolating mRNA from the sample and subjecting it to a reverse transcriptase polymerase chain reaction so as to produce cDNAs corresponding to the alternatively spliced mRNA isoforms and then quantitating the cDNA corresponding to the alternatively spliced mRNA isoforms. In embodiments of all of the methods described herein involving mRNA amplification and/or the various types of PCR, the proportionality of the mRNA isoforms in the sample is substantially maintained (e.g. as reflected in the proportions of the different resultant corresponding cDNAs or in the amplified mRNAs) when the one or more amplification procedures and/or reverse transcriptase polymerase chain reactions, have been performed.

In an embodiment, quantitating the alternatively spliced gene expression products is effected indirectly by isolating alternatively spliced gene expression products corresponding to the alternatively spliced mRNA isoforms and then quantitating the alternatively spliced gene expression products corresponding to the alternatively spliced mRNA isoforms.

In an embodiment, a level of $\Delta\psi=-0.2$ or less for each of CD44, NUMB, FAM62B, SLK, ENAH, H2AFY and OSBPL8; CD44, NUMB, FAM62B, SLK, ENAH, H2AFY, OSBPL8, C17orf61/PLSCR3, STARD10/CENTD2, MAP3K7, BMP1, and BTG3; or ENAH, SLC37A2, MBNL1 and FLNB, indicates that the tumor is not likely to metastasize or is not likely to have metastasized already, and wherein a level of $\Delta\psi=+0.2$ or more for each of SCRIB, CLSTN1, MLPH, TXNDC14 and CTNND1; YWHAB, ILF3, PAM, SCRIB, CLSTN1, MLPH, and TXNDC14 and/or CTNND1; or MLPH and ARHGEF11, indicates that the tumor is likely to metastasize or is likely to have metastasized already.

In an embodiment, a level of $\Delta\psi=-0.3$ or less for each of CD44, NUMB, FAM62B, SLK, ENAH, H2AFY and OSBPL8; CD44, NUMB, FAM62B, SLK, ENAH, H2AFY, OSBPL8, C17orf61/PLSCR3, STARD10/CENTD2, MAP3K7, BMP1, and BTG3; or ENAH, SLC37A2, MBNL1 and FLNB, indicates that the tumor is not likely to metastasize or is not likely to have metastasized already, and wherein a level of $\Delta\psi=+0.3$ or more for each of SCRIB, CLSTN1, MLPH, TXNDC14 and CTNND1; YWHAB, ILF3, PAM, SCRIB, CLSTN1, MLPH, and TXNDC14 and/or CTNND1; or MLPH and ARHGEF11, indicates that the tumor is likely to metastasize or is likely to have metastasized already.

In an embodiment, the control proportion corresponds to the alternatively spliced mRNA isoforms proportion in a non-malignant, non-tumor epithelial cell of the tissue type that the tumor is present in. In an embodiment, the control proportion corresponds to the alternatively spliced mRNA isoforms proportion in a benign fibroadenoma cell. In an embodiment, the tumor is in a subject. In an embodiment, the tumor is a primary tumor which has been excised from a subject and the method is for identifying if the tumor has likely metastasized. In an embodiment, the method is for identifying if the tumor will likely metastasize. In an embodiment, the tumor is a pancreas, prostate, colon, brain, liver, lung, head or neck tumor, or a secretory epithelial tumor. In an embodiment, determining the levels of alternatively spliced mRNA isoforms is effected using an exon microarray.

Also provide is a method for identifying a tumor as likely to metastasize via lymph nodes in a subject, or likely to have metastasized via lymph nodes in a subject, comprising obtaining a sample of the tumor and determining if an alternatively spliced skipped exon mRNA isoform for SLC37A2 gene is present in the sample, wherein the absence of an alternatively spliced skipped exon mRNA isoform for SLC37A2 gene present in the sample, or a reduced level of an alternatively spliced skipped exon mRNA isoform for SLC37A2 gene present in the sample as compared to a non-metastatic control sample, indicates that the tumor is likely to metastasize via lymph nodes in the subject, or has likely metastasized via lymph nodes in the subject.

In an embodiment, the presence of the alternatively spliced skipped exon mRNA isoform for SLC37A2 gene is determined by performing a quantitative reverse transcriptase polymerase chain reaction ("qRT-PCR") on the sample with a primer pair targeting the skipped exon and a primer pair targeting an independent constitutive exon of SLC37A2, wherein a ratio of the quantity of the cDNAs comprising sequences corresponding to the primer pair targeting the skipped exon to the quantity of the cDNAs comprising sequences corresponding to the primer pair targeting the independent constitutive exon of SLC37A2 of 0.5 or less indicates that the tumor is likely to metastasize via lymph nodes in the subject, or has likely metastasized via lymph nodes in the subject. In an embodiment, the SLC37A2 gene is a human SLC37A2 gene.

Also provided is a method for identifying an agent for inhibiting metastasis of a cancer comprising: a) obtaining a sample of the cancer; b) quantitating alternatively spliced mRNA isoforms of a cell motility gene, a cell adhesion gene and/or an actin cytoskeletal remodeling gene in the cancer or any of the genes exhibiting positive M-E.deltaPsi values in inc/excBound column of Table 5; c) contacting the sample with the agent; and d) quantitating the alternatively spliced mRNA isoforms of the cell motility gene, cell adhesion gene and/or actin cytoskeletal remodeling gene or the gene(s) exhibiting positive M-E.deltaPsi values in inc/excBound column of Table 5 in the sample, wherein a reduction in the amount of alternatively spliced mRNA isoforms of the cell motility gene, cell adhesion gene, the actin cytoskeletal remodeling gene, and/or the gene(s) exhibiting positive M-E.deltaPsi values in inc/excBound column of Table 5 in the presence of the agent indicates that the agent inhibits metastasis of a cancer.

In an embodiment, the genes are chosen from ENAH, SLC37A2, MBNL1, FLNB, MLPH, and ARHGEF11. In an embodiment, at least one of the alternatively spliced mRNA isoforms encodes a hinge region (H1) located between stretches of filamin repeats. In an embodiment, at least one of the alternatively spliced mRNA isoforms encodes an extracellular domain of a transmembrane protein. In an embodiment, quantitating the alternatively spliced mRNA isoforms is effected indirectly by isolating mRNA from the sample and subjecting it to a reverse transcriptase polymerase chain reaction so as to produce cDNAs corresponding to the alternatively spliced mRNA isoforms and then quantitating the cDNA corresponding to the alternatively spliced mRNA isoforms. In an embodiment, quantitating the alternatively spliced mRNA isoforms is effected indirectly by isolating protein isoforms corresponding to the alternatively spliced mRNA isoforms and then quantitating the protein isoforms corresponding to the alternatively spliced mRNA isoforms.

Also provided is a method for identifying an agent for inhibiting metastasis of a cancer comprising: a) obtaining a sample of the cancer; b) quantitating, in the absence of the agent, the level of one or more RNA binding proteins set forth hereinbelow; c) contacting the sample with the agent; and d) quantitating the level of the one or more RNA binding proteins in the presence of the agent, wherein a fold change of at least 1.5× either up or down in the sample in the presence of the agent as compared to predetermined control RNA binding proteins levels indicates that the agent inhibits metastasis of a cancer.

In an embodiment, the predetermined control RNA binding proteins levels are determined from non-malignant epithelial cells. In an embodiment, the sample is from cancer identified as metastatic.

In an embodiment, the RNA binding proteins are chosen from the group consisting of MBNL1, RBM9, PTBP1, PTBP2, HNRNPF, HNRNPH, ESRP1, ESRP2, RBM47. In an embodiment, the RNA binding proteins are splicing factors including one, more than one, or all of the classes: MBNL, CELF, RBFOX, hnRNP and ESRP. In an embodiment, the RBFOX is RBFOX2. In an embodiment, the hnRNP is hnRNP F/H or L. In an embodiment, the ESRP is ESRP1 or ESRP2. In an embodiment and agent that increases, or prevents a reduction in ESRP1 and in ESRP2 levels is an agent that inhibits metastasis of a cancer. In an embodiment, an agent that increases ESRP1 and in ESRP2 levels by at least 1.5× is an agent that inhibits metastasis of a cancer. In an embodiment, the method is carried out in vitro.

RNA binding proteins as referred to in the methods (and which show a statistically significant change and a fold change of 1.5× either up or down in mesenchymal cells compared to control epithelial cells): RNA binding motif protein 35A; RNA binding motif protein 35B; poly(A) binding protein, cytoplasmic 1-like; ribosomal protein L3-like; eukaryotic translation initiation factor 5A-like 1; nuclear receptor subfamily 0, group B, member 1; RNA binding motif protein 47; peroxisome proliferator-activated receptor gamma, coactivator 1 beta; zinc finger protein 36, C3H type, homolog; splicing factor, arginine/serine-rich 16; tRNA splicing endonuclease 54 homolog; peroxisomal proliferator-activated receptor A interacting complex 285; DEAD (Asp-Glu-Ala-Asp) box polypeptide 51; ribonuclease P/MRP 25 kDa subunit; DEAD/H (Asp-Glu-Ala-Asp/His) box polypeptide 11 (CRL1-like helicase homolog); PRP40 pre-mRNA processing factor 40 homolog B; telomerase reverse transcriptase; pseudouridylate synthase-like 1; A kinase (PRKA) anchor protein 1; mitochondrial rRNA methyltransferase 1 homolog; RNA pseudouridylate synthase domain containing 1; spen homolog, transcriptional regulator; mex-3 homolog D; PHD and ring finger domains 1; DEAD (Asp-Glu-Ala-Asp) box polypeptide 54; surfeit 6; THO complex 3; ELAV (embryonic lethal, abnormal vision, Drosophila)-like 2 (Hu antigen B); telomerase-associated protein 1; spermatid perinuclear RNA binding protein; transcription termination factor, RNA polymerase II; ribonucleoprotein, PTB-binding 1; pseudouridylate synthase 1; distal-less homeobox 2; splicing factor, arginine/serine-rich 8 (suppressor-of-white-apricot homolog); breast cancer 1, early onset; peter pan homolog; zinc finger protein 74; mitochondrial ribosomal protein L12; serine/arginine repetitive matrix 2; exosome component 5; lon peptidase 1, mitochondrial; dead end homolog 1; bromodomain adjacent to zinc finger domain, 2A; UPF3 regulator of nonsense transcripts homolog B; UPF1 regulator of nonsense transcripts homolog; small nuclear ribonucleoprotein 70 kDa polypeptide (RNP antigen); HpaII tiny fragments locus 9C; THO complex 6 homolog; AD51 associated protein 1; eukaryotic translation initiation factor 2C, 2; ribosomal RNA processing 7 homolog A; heterogeneous nuclear ribonucleoprotein H2 (H'); calcium homeostasis endoplasmic reticulum protein; cleavage and polyadenylation specific factor 1, 160 kDa; nuclear assembly factor 1 homolog; SET domain containing 1A; TRM1 tRNA methyltransferase 1 homolog; serine/arginine repetitive matrix 1; interferon stimulated exonuclease gene 20 kDa; RAD52 motif 1; 2',5'-oligoadenylate synthetase 1, 40/46 kDa; peroxisome proliferator-activated receptor gamma, coactivator-related 1; RNA binding motif protein 19; XPA binding protein 2; F-box and leucine-rich repeat protein 10; gem (nuclear organelle) associated protein 4; chromosome 19 open reading frame 29; programmed cell death 7; zinc finger CCCH-type containing 3; DAZ associated protein 1; similar to ribonucleic acid binding protein S1; immunoglobulin mu binding protein 2; chromosome 14 open reading frame 21; exosome component 6; tRNA splicing endonuclease 34 homolog; TAR (HIV-1) RNA binding protein 1; DEAH (Asp-Glu-Ala-His) box polypeptide 34; DEAH (Asp-Glu-Ala-His) box polypeptide 30; exosome component 3; fibrillarin; PIN2-interacting protein 1; splicing factor 3a, subunit 2, 66 kDa; 2'-5'-oligoadenylate synthetase 3, 100 kDa; RNA binding motif protein 15; nucleolin; La ribonucleoprotein domain family, member 6; scaffold attachment factor B; pseudouridylate synthase 7 homolog; exosome component 4; heterogeneous nuclear ribonucleoprotein D (AU-rich element RNA binding protein 1, 37 kDa); RNA binding motif protein 38; enhancer of mRNA decapping 4; nucleolar protein 14; SAFB-like, transcription modulator; terminal uridylyl transferase 1, U6 snRNA-specific; pinin, desmosome associated protein; peptidylprolyl isomerase G (cyclophilin G); RNA pseudouridylate synthase domain containing 3; interleukin enhancer binding factor 3, 90 kDa; dicer 1, ribonuclease type III; splicing factor, arginine/serine-rich 4;

eukaryotic translation initiation factor 4 gamma, 1; phenylalanyl-tRNA synthetase, alpha subunit; RNA binding motif protein 41; IMP3, U3 small nucleolar ribonucleoprotein, homolog; endoplasmic reticulum to nucleus signaling 1; muscleblind-like 3; heterogeneous nuclear ribonucleoprotein M; DEAD (Asp-Glu-Ala-Asp) box polypeptide 55; La ribonucleoprotein domain family, member 1; BTB (POZ) domain containing 2; U2-associated SR140 protein; cyclin-dependent kinase 9; RNA binding motif protein 4; leucine rich repeat containing 47; tRNA 5-methylaminomethyl-2-thiouridylate methyltransferase; splicing factor, arginine/serine-rich 15; polyribonucleotide nucleotidyltransferase 1; influenza virus NS1A binding protein; similar to ribosomal protein L29; UPF3 regulator of nonsense transcripts homolog A; DEAD (Asp-Glu-Ala-Asp) box polypeptide 21; RNA binding motif protein 10; nucleolar protein family A, member 2 (H/ACA small nucleolar RNPs); symplekin; splicing factor, arginine/serine-rich 2; polypyrimidine tract binding protein 1; TAR (HIV-1) RNA binding protein 2; adenosine deaminase, RNA-specific, B1; polymerase (RNA) II (DNA directed) polypeptide A, 220 kDa; nucleolar protein 12; fragile X mental retardation, autosomal homolog 2; exosome component 2; small nuclear ribonucleoprotein polypeptide A; polymerase (RNA) II (DNA directed) polypeptide E, 25 kDa; ROD1 regulator of differentiation 1; U2 small nuclear RNA auxiliary factor 2; UPF2 regulator of nonsense transcripts homolog; mitochondrial ribosomal protein L23; eukaryotic translation initiation factor 4E binding protein 3; activator of basal transcription 1; RNA binding motif protein 33; eukaryotic elongation factor, selenocysteine-tRNA-specific; apolipoprotein B mRNA editing enzyme, catalytic polypeptide-like 3G; similar to ribosomal protein L18a; TAF15 RNA polymerase II, TATA box binding protein (TBP)-associated factor, 68 kDa; hexamthylene bis-acetamide inducible 2; squamous cell carcinoma antigen recognized by T cells 3; methyltransferase like 3; polymerase (RNA) II (DNA directed) polypeptide J, 13.3 kDa; ribonucleoprotein, PTB-binding 2; nucleolar protein 1, 120 kDa; interferon induced with helicase C domain 1; RNA binding protein, autoantigenic (hnRNP-associated with lethal yellow homolog); Ewing sarcoma breakpoint region 1; squamous cell carcinoma antigen recognized by T cells; myelin expression factor 2; KIAA0020; NOL1/NOP2/Sun domain family, member 2; CCR4-NOT transcription complex, subunit 6-like; hypothetical protein LOC100130562; DIS3 mitotic control homolog-like 2; methyl-CpG binding domain protein 2; PRP38 pre-mRNA processing factor 38 domain containing B; splicing factor, arginine/serine-rich 11; alanyl-tRNA synthetase 2, mitochondrial (putative); proliferation-associated 2G4, 38 kDa; heterogeneous nuclear ribonucleoprotein F; ribosomal RNA processing 9, small subunit (SSU) processome component homolog; gem (nuclear organelle) associated protein 5; RNA binding motif protein 25; Mov10, Moloney leukemia virus 10 homolog; trinucleotide repeat containing 6B; dihydrouridine synthase 2-like, SMM1 homolog; ribosomal protein L13 pseudogene; RNA binding motif protein 26; DEAD (Asp-Glu-Ala-Asp) box polypeptide 39; SERPINE1 mRNA binding protein 1; LSM4 homolog, U6 small nuclear RNA associated; RNA binding motif protein 15B; La ribonucleoprotein domain family, member 7; tudor and KH domain containing; splicing factor 1; PRP31 pre-mRNA processing factor 31 homolog; SR-related CTD-associated factor 1; SECIS binding protein 2; DEAH (Asp-Glu-Ala-His) box polypeptide 16; jerky homolog; glutamyl-tRNA synthetase 2, mitochondrial (putative); DEAH (Asp-Glu-Ala-His) box polypeptide 35; trinucleotide repeat containing 6A; splicing factor, arginine/serine-rich 12; RNA pseudouridylate synthase domain containing 2; splicing factor, arginine/serine-rich 9; DEXH (Asp-Glu-X-His) box polypeptide 58; heterogeneous nuclear ribonucleoprotein A/B; RNA binding motif protein 28; eukaryotic translation initiation factor 5A-like 1; cisplatin resistance-associated overexpressed protein; cytoplasmic polyadenylation element binding protein 3; AU RNA binding protein/enoyl-Coenzyme A hydratase; nucleolar protein 5A (56 kDa with KKE/D repeat); programmed cell death 11; cleavage stimulation factor, 3' pre-RNA, subunit 2, 64 kDa; KH-type splicing regulatory protein; RNA binding motif protein 27; heterogeneous nuclear ribonucleoprotein A0; insulin-like growth factor 2 mRNA binding protein 2; methenyltetrahydrofolate synthetase domain containing; RNA methyltransferase like 1; jumonji domain containing 6; heterogeneous nuclear ribonucleoprotein A1; zinc finger protein 36, C3H type-like 1; nucleolar protein family 6 (RNA-associated); heterogeneous nuclear ribonucleoprotein U (scaffold attachment factor A); scaffold attachment factor B2; WD repeat domain 79; eukaryotic translation initiation factor 2C, 4; cell division cycle and apoptosis regulator 1; exosome component 7; structural maintenance of chromosomes 1A; ribosomal protein L8 pseudogene 2; superkiller viralicidic activity 2-like; KIAA1604 protein; DEAD (Asp-Glu-Ala-Asp) box polypeptide 46; thyroid hormone receptor, alpha (erythroblastic leukemia viral (v-erb-a) oncogene homolog); PRKR interacting protein 1 (IL11 inducible); hexamethylene bis-acetamide inducible 1; eukaryotic translation initiation factor 3, subunit B; poly-U binding splicing factor 60 KDa; stem-loop binding protein; DCP2 decapping enzyme homolog; heterogeneous nuclear ribonucleoprotein U-like 1; YTH domain containing 1; RNA binding motif protein 42; CCR4-NOT transcription complex, subunit 6; eukaryotic translation initiation factor 4A, isoform 1; 2'-5'-oligoadenylate synthetase-like; SON DNA binding protein; PCF11, cleavage and polyadenylation factor subunit, homolog; DiGeorge syndrome critical region gene 14; DEAD (Asp-Glu-Ala-Asp) box polypeptide 41; RCAN family member 3; eukaryotic translation initiation factor 3, subunit G; SFRS protein kinase 1; PRP40 pre-mRNA processing factor 40 homolog A; poly(rC) binding protein 1; RNA binding protein with multiple splicing; eukaryotic translation initiation factor 2-alpha kinase 2; DEAD (Asp-Glu-Ala-Asp) box polypeptide 28; zinc finger protein 346; DEAD (Asp-Glu-Ala-Asp) box polypeptide 18; tRNA splicing endonuclease 2 homolog; mitochondrial ribosomal protein S5; heterogeneous nuclear ribonucleoprotein A2/B1; THO complex 2; RNA pseudouridylate synthase domain containing 4; similar to hCG1791993; RNA binding motif protein 6; DEAD (Asp-Glu-Ala-Asp) box polypeptide 59; gem (nuclear organelle) associated protein 8; ataxin 2; DEAH (Asp-Glu-Ala-His) box polypeptide 38; similar to hCG1820375; RNA binding motif protein 12B; splicing factor, arginine/serine-rich 5; ribosomal L1 domain containing 1; splicing factor, arginine/serine-rich 14; protein phosphatase 1, regulatory (inhibitor) subunit 9B; CUG triplet repeat, RNA binding protein 1; eukaryotic translation initiation factor 4E; DEAD (Asp-Glu-Ala-Asp) box polypeptide 31; protein arginine methyltransferase 7; activating signal cointegrator 1 complex subunit 3-like 1; mitochondrial ribosomal protein L16; elongation factor Tu GTP binding domain containing 2; leucine-rich PPR-motif containing; nucleolar protein 3 (apoptosis repressor with CARD domain); translocase of inner mitochondrial membrane 50 homolog; PRP19/PSO4 pre-mRNA processing factor 19 homolog; Era G-protein-like 1; zinc finger CCCH-type containing 8; TruB pseudouridine (psi) synthase homolog 2;

cyclin T1; polymerase (RNA) II (DNA directed) polypeptide H; BRCA1 associated RING domain 1; small nuclear ribonucleoprotein polypeptide A; fusion (involved in malignant liposarcoma); DCP1 decapping enzyme homolog A; PRP39 pre-mRNA processing factor 39 homolog; polymerase (RNA) II (DNA directed) polypeptide I, 14.5 kDa; family with sequence similarity 120A; muscleblind-like 2; DEAD (Asp-Glu-Ala-Asp) box polypeptide 23; DEAD (Asp-Glu-Ala-As) box polypeptide 19A; similar to E3 ubiquitin protein ligase, HECT domain containing, 1; cleavage and polyadenylation specific factor 6, 68 kDa; HLA-B associated transcript 1; splicing factor 3b, subunit 2, 145 kDa; exportin 1 (CRM1 homolog); PRP38 pre-mRNA processing factor 38 domain containing A; within bgcn homolog; poly(A) binding protein, nuclear 1; eukaryotic translation initiation factor 4 gamma, 3; DEAD (Asp-Glu-Ala-Asp) box polypeptide 56; general transcription factor IIF, polypeptide 1, 74 kDa; ankyrin repeat domain 17; amyloid beta (A4) precursor protein; similar to 60S ribosomal protein L3 (L4); WW domain binding protein 11; mitochondrial ribosomal protein S7; nuclear fragile X mental retardation protein interacting protein 1; DEAD (Asp-Glu-Ala-Asp) box polypeptide 10; ribonuclease H2, subunit A; RNA binding motif protein 17; heterogeneous nuclear ribonucleoprotein K; DEAD (Asp-Glu-Ala-Asp) box polypeptide 49; splicing factor, arginine/serine-rich 7, 35 kDa; dyskeratosis congenita 1, dyskerin; protein phosphatase 2 (formerly 2A), regulatory subunit A, alpha isoform; ribosomal protein L18; WD repeat domain 77; THO complex 4; gem (nuclear organelle) associated protein 7; solute carrier family 4 (anion exchanger), member 1, adaptor protein; KRR1, small subunit (SSU) processome component, homolog; nucleolar protein 8; heat shock protein 90 kDa beta (Grp94), member 1; fragile X mental retardation 1; ribosomal protein, large, P1; RNA binding motif protein, X-linked; KH domain containing, RNA binding, signal transduction associated 1; heterogeneous nuclear ribonucleoprotein A3; DIS3 mitotic control homolog; adenosine deaminase, tRNA-specific 1; hypothetical protein LOC100129492; splicing factor 3b, subunit 4, 49 kDa; PRP8 pre-mRNA processing factor 8 homolog; RNA binding motif protein 8A; LSM14A, SCD6 homolog A; NFKB repressing factor; protein phosphatase 1, regulatory (inhibitor) subunit 10; signal recognition particle 9 kDa; heterogeneous nuclear ribonucleoprotein D-like; DnaJ (Hsp40) homolog, subfamily C, member 17; polymerase (RNA) II (DNA directed) polypeptide L, 7.6 kDa; PAP associated domain containing 1; protein arginine methyltransferase 5; similar to U5 snRNP-associated 102 kDa protein (U5-102 kDa protein); CDKN2A interacting protein; zinc finger protein 638; TruB pseudouridine (psi) synthase homolog 1; chromosome 6 open reading frame 151; poly(A) binding protein, cytoplasmic 1; ribosomal protein, large, P0; synaptotagmin binding, cytoplasmic RNA interacting protein; pseudouridylate synthase 7 homolog-like; nuclear RNA export factor 1; chromosome 14 open reading frame 156; SYF2 homolog, RNA splicing factor; hypothetical LOC727826; similar to mCG146274; programmed cell death 4 (neoplastic transformation inhibitor); ribosomal protein S13; signal recognition particle 19 kDa; peptidylprolyl isomerase (cyclophilin)-like 3; nudix (nucleoside diphosphate linked moiety X)-type motif 16; ribosomal protein L26; ribosomal protein S25; polymerase I and transcript release factor; ribonuclease L (2',5'-oligoisoadenylate synthetase-dependent); aconitase 1, soluble; signal recognition particle 14 kDa (homologous Alu RNA binding protein); ribosomal protein L37; proteasome (prosome, macropain) subunit, alpha type, 6; ribosomal protein S20; ribosomal protein L34; malignant T cell amplified sequence 1; ribosomal protein L24; RNA binding motif, single stranded interacting protein; similar to mCG49427; ribosomal protein L38; eukaryotic translation initiation factor 4E family member 3; ribosomal protein L35a; small nuclear ribonucleoprotein polypeptide N; LSM1 homolog, U6 small nuclear RNA associated; similar to hCG1643032; similar to Sm protein G; 2'-5'-oligoadenylate synthetase 2, 69/71 kDa; cytoplasmic polyadenylation element binding protein 1; bicaudal C homolog 1; apolipoprotein B mRNA editing enzyme, catalytic polypeptide-like 3B; angiogenin, ribonuclease, RNase A family, 5; mex-3 homolog B; zinc finger, matrin type 3; Mov10l1, Moloney leukemia virus 10-like 1, homolog; amyloid beta (A4) precursor-like protein 1; ribonuclease, RNase A family, 4; toll-like receptor 3. In an embodiment, the RNA binding proteins listed hereinabove are the human protein or human homolog.

Also provided is a method of inhibiting metastasis of a tumor in a subject comprising administering to the subject an amount of an agent which (i) inactivates or reduces expression of one or more genes having a negative M-E.deltaPsi value in M-E.deltaPsi Column of Table 5 or (ii) inactivates or reduces activity of an alternatively spliced exon gene expression product of one or more genes having a negative M-E.deltaPsi Column of Table 5.

Also provided is a method of inhibiting metastasis of a tumor in a subject comprising administering to the subject an amount of an agent which (i) activates or increases expression of one or more genes having a positive M-E.deltaPsi Column of Table 5 or (ii) activates or increases activity of an alternatively spliced exon gene expression product of one or more genes having a negative M-E.deltaPsi Column of Table 5. In an embodiment, the agent is a monoclonal antibody. In an embodiment, the agent is small organic molecule having a mass of 1200 daltons or less, or 1000 daltons or less, or 800 daltons or less. In an embodiment, the agent is an siRNA. In an embodiment, the agent is an shRNA. In an embodiment, the agent which xxx is an siRNA (small interfering RNA) or shRNA. The siRNA/shRNA comprises a portion which is complementary to an mRNA sequence encoded by the gene of interest, and the siRNA or shRNA is effective to inhibit expression of the gene product. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding a gene expression product to be inhibited. In another embodiment, a siRNA of the invention comprises a double-stranded RNA wherein one strand of the RNA comprises a portion having a sequence the same as a portion of 18-25 consecutive nucleotides of an RNA transcript of a gene expression product to be inhibited. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure. In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length. In yet another embodiment, a siRNA of the invention is 46 nucleotides in length. In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

The short hairpin RNA ("shRNA") can be introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

Also provided is a method of determining a treatment type for a patient having a tumor comprising determining in a sample of the tumor the proportion of (1) alternatively spliced mRNA isoforms of one or more genes having a positive M-E.deltaPsi Column of Table 5 relative to the total mRNA isoforms of the one or more genes having a positive M-E.deltaPsi value in M-E.deltaPsi Column of Table 5 in the sample or (2) the proportion of alternatively spliced gene expression products of one or more genes having a positive M-E.deltaPsi Column of Table 5 relative to the total gene expression products of the one or more genes having a positive M-E.deltaPsi Column of Table 5 in the sample, wherein determination of a proportion of (1) alternatively spliced mRNA isoforms, or (2) alternatively spliced gene expression products, respectively, for the one or more genes equal to, or greater than, that of a control proportion indicates that the patient should be treated with one or more chemotherapeutic anti-tumor agents, and wherein determination of a proportion of alternatively spliced mRNA isoforms, or alternatively spliced gene expression products, respectively, for the one or more genes less than that of a control proportion indicates that the patient should be treated with one or more non-chemotherapeutic anti-tumor agents. In an embodiment, the control proportion is 0.1. In an embodiment, the control proportion is 0.2. In an embodiment, the control proportion is 0.3. In an embodiment, the control proportion is determined from a tumor sample from one or more subjects susceptible to chemotherapy.

As used herein, unless context indicates otherwise, a "control" value (e.g. a control proportion, a control amount, a $\psi_{control}$ value) is determined from a suitable comparison sample which would be readily identified by one of ordinary skill in the art. For example, the control value can be determined from a non-cancerous and/or non-metastatic sample. For example, such a sample can be matched by one or more of age, position, tissue type, collection conditions, size etc. and may be normalized and/or standardized as desired.

Also provided is a product comprising an exon microarray which comprises a plurality of oligonucleotides having sequences corresponding to the sequences of the exons of the genes recited hereinabove. The exon microarray can comprise one or more probes for each exon of one or more of the genes, for identified skipped or mutually exclusive exons of one or more the genes, or any subset thereof.

Also provided is a product comprising an exon microarray which comprises a plurality of oligonucleotides having sequences corresponding to the sequences of exon:exon junctions found in the wildtype of the of the genes comprising the exons listed in inc/excBound Column of Table 5. The exon microarray can comprise one or more probes for each exon of one or more of the genes, for identified skipped or mutually exclusive exons of one or more the genes, or any subset thereof.

In an embodiment, the product further comprises one or more cDNA probes derived from a tumor being tested for likelihood of metastases.

As used herein an "mRNA isoform" is any one of a plurality of different mRNAs resulting from RNA splicing of a primary transcript of a given gene. In an embodiment of all the methods described herein, the mRNA(s) is/are mature mRNA(s).

This inventions provides a method for identifying a tumor as likely to metastasize, or likely to have metastasized, comprising obtaining a sample of the tumor and quantitating alternatively spliced mRNA isoforms of a cell motility gene, a cell adhesion gene and/or an actin cytoskeletal remodeling gene in the sample, wherein an amount of alternatively spliced mRNA isoforms of the cell motility gene, cell adhesion gene and/or the actin cytoskeletal remodeling, gene different to a predetermined control amount indicates that the tumor is likely to metastasize or is likely to have metastasized.

In an embodiment, the genes are chosen from the group consisting of ENAH, SLC37A2, MBNL1, FLNB, MLPH, and ARHGEF11. In an embodiment, the sample is a breast cancer sample. In an embodiment, the tumor is an invasive duct carcinoma. In an embodiment, the sample is obtained by fine needle aspiration. In an embodiment, the alternatively spliced mRNA isoforms result from a skipped exon, a mutually exclusive exon, a retained intron, an alternative 5' splice site, an alternative 3' splice site, an alternative 3' UTR, an alternative first exon, and/or an alternative last exon. In an embodiment, quantitating the alternatively spliced mRNA isoforms is effected indirectly by isolating mRNA from the sample and subjecting it to a reverse transcriptase polymerase chain reaction so as to produce cDNAs corresponding to the alternatively spliced mRNA isoforms and then quantitating the cDNA corresponding to the alternatively spliced mRNA isoforms. In an embodiment, quantitating the alternatively spliced mRNA isoforms is effected indirectly by isolating protein isoforms corresponding to the alternatively spliced mRNA isoforms and then quantitating the protein isoforms corresponding to the alternatively spliced mRNA isoforms. In an embodiment, the alternatively spliced mRNA isoforms are altered or increased at least 10% compared to the predetermined control amount, that is ΔΨ>0.1 or ΔΨ<−0.1. In an embodiment, the alternatively spliced mRNA isoforms are altered or increased 30% or more compared to the predetermined control amount, that is ΔΨ>0.3 or ΔΨ<−0.3. In an embodiment, the predetermined control amount corresponds to the alternatively spliced mRNA isoforms amount in a non-malignant, non-tumor epithelial cell. In an embodiment, the predetermined control amount corresponds to the alternatively spliced mRNA isoforms amount in a benign fibroadenoma cell. In an embodiment, the tumor is in a subject. In an embodiment, the tumor is a primary tumor which has been excised from a subject and the method is for identifying if the tumor has likely metastasized. In an embodiment, the alternatively spliced cell motility gene, cell adhesion gene, or actin cytoskeletal remodeling gene encodes at least an extracellular domain of a transmembrane protein. In an embodiment, the tumor is a pancreas, prostate, colon, brain, liver, lung, head or neck tumor, or a secretory epithelial tumor. In an embodiment, the alternatively spliced mRNA isoforms are quantitated using a microarray.

This invention provides a method for identifying a tumor as likely to metastasize via lymph nodes in a subject, or likely to have metastasized via lymph nodes in a subject, comprising obtaining a sample of the tumor and determining if an alternatively spliced skipped exon mRNA isoform for SLC37A2 gene is present in the sample, wherein the absence of an alternatively spliced skipped exon mRNA isoform for SLC37A2 gene present in the sample, or a reduced level of an alternatively spliced skipped exon mRNA isoform for SLC37A2 gene present in the sample as compared to a non-malignant control sample, indicates that the tumor is likely to metastasize via lymph nodes in the subject, or has likely metastasized via lymph nodes in the subject.

In an embodiment, the presence of the alternatively spliced skipped exon mRNA isoform for SLC37A2 gene is determined by performing a quantitative reverse transcriptase polymerase chain reaction ("qRT-PCR") on the sample with a primer pair targeting the skipped exon and a primer pair targeting an independent constitutive exon of SLC37A2, wherein a ratio of the quantity of the cDNAs comprising the primer pair targeting the skipped exon to the quantity of the cDNAs comprising the primer pair targeting the independent constitutive exon of SLC37A2 of 0.5 or less indicates that the tumor is likely to metastasize via lymph nodes in the subject, or has likely metastasized via lymph nodes in the subject.

This invention provides a method for identifying an agent for inhibiting metastasis of a cancer comprising: a) obtaining a sample of the cancer; b) quantitating alternatively spliced mRNA isoforms of a cell motility gene, a cell adhesion gene and/or an actin cytoskeletal remodeling gene in the cancer; c) contacting the sample with the agent; and d) quantitating the alternatively spliced mRNA isoforms of the cell motility gene, cell adhesion gene and/or actin cytoskeletal remodeling gene in the sample, wherein a reduction in the amount of alternatively spliced mRNA isoforms of the cell motility gene, cell adhesion gene and/or the actin cytoskeletal remodeling gene in the presence of the agent indicates that the agent inhibits metastasis of a cancer.

In an embodiment, the genes are chosen from the group consisting of ENAH, SLC37A2, MBNL1, FLNB, MLPH, and ARHGEF11. In an embodiment, at least one of the alternatively spliced mRNA isoforms encodes a hinge region (H1) located between stretches of filamin repeats. In an embodiment, at least one of the alternatively spliced mRNA isoforms encodes an extracellular domain of a transmembrane protein. In an embodiment, quantitating the alternatively spliced mRNA isoforms is effected indirectly by isolating mRNA from the sample and subjecting it to a reverse transcriptase polymerase chain reaction so as to produce cDNAs corresponding to the alternatively spliced mRNA isoforms and then quantitating the cDNA corresponding to the alternatively spliced mRNA isoforms. In an embodiment, quantitating the alternatively spliced mRNA isoforms is effected indirectly by isolating protein isoforms corresponding to the alternatively spliced mRNA isoforms and then quantitating the protein isoforms corresponding to the alternatively spliced mRNA isoforms.

This invention provides a method for identifying an agent for inhibiting metastasis of a cancer comprising: a) obtaining a sample of the cancer; b) quantitating RNA binding proteins levels for one or more RNA binding proteins listed hereinabove; c) contacting the sample with the agent; and d) quantitating RNA binding proteins levels for one or more RNA binding proteins set forth hereinabove in the sample in the presence of the agent, wherein a fold change of at least 1.5× either up or down in the sample in the presence of the agent compared to predetermined control RNA binding proteins levels indicates that the agent inhibits metastasis of a cancer.

In an embodiment, the predetermined control RNA binding proteins levels are determined from non-malignant epithelial cells. In an embodiment, the RNA binding proteins are chosen from the group consisting of MBNL1, RBM9, PTBP1, PTBP2, HNRNPF, HNRNPH, ESRP1, ESRP2, RBM47. In an embodiment, the method is carried out in vitro. In an embodiment, the agent is a monoclonal antibody. In an embodiment, the agent is small organic molecule having a mass of 800 daltons or less. In an embodiment, the agent is an siRNA.

Also provided is a product comprising an exon microarray which comprises a plurality of oligonucleotides having sequences corresponding to the sequences of the exons of the genes recited above.

Also provided is a product comprising an exon microarray which comprises a plurality of oligonucleotides having sequences corresponding to the sequences of exon:exon junctions found in the wildtype of the of the genes recited above.

In an embodiment of the products, the product further comprises one or more cDNA probes derived from a tumor being tested for likelihood of metastases.

In an embodiment of the products, the plurality of oligonucleotides having sequences corresponding to the sequences of exon:exon junctions found in the wildtype of the of the genes recited above comprises oligonucleotides having sequences corresponding to the sequences of every exon:exon junction found in the wildtype of the of the genes recited above.

In an embodiment of the products, the plurality of oligonucleotides further comprises probes corresponding to skipped exon splice variant(s), mutually exclusive exon splice variant(s), alternative first exon splice variant(s), alternative last exon splice variant(s), retained intron splice variant(s), alternative to 5' splice site splice variant(s), alternative to 3' splice site splice variant(s) and/or tandem 3' UTR splice variants of the genes recited above.

In an embodiment, the product or exon microarray is a microarray comprising probes attached via surface engineering to a solid surface by a covalent bond to a chemical matrix (via, in non-limiting examples, epoxy-silane, amino-silane, lysine, polyacrylamide). Suitable solid surface can be, in non-limiting examples, glass or a silicon chip, a solid bead forms of, for example, polystyrene. As used herein, unless otherwise specified, a microarray includes both solid-phase microarrays and bead microarrays. In an embodiment, the microarray is a solid-phase microarray. In an embodiment, the microarray is a plurality of beads microarray. In an embodiment, the microarray is a spotted microarray. In an embodiment, the microarray is an oligonucleotide microarray. The oligonucleotide probes of the microarray may be of any convenient length necessary for unique discrimination of targets. In non limiting examples, the oligonucleotide probes are 20 to 30 nucleotides in length, 31 to 40 nucleotides in length, 41 to 50 nucleotides in length, 51 to 60 nucleotides in length, 61 to 70 nucleotides in length, or 71 to 80 nucleotides in length. In an embodiment, the target sample, or nucleic acids derived from the target sample, such as mRNA or cDNA, are contacted with a detectable marker, such as one or more fluorophores, under conditions permitting the fluorophore to attach to the target sample or nucleic acids derived from the target sample. In non-limiting examples the fluorophores are cyanine 3, cyanine 5. In an embodiment, the target hybridized to the probe can be detected by conductance, MS, electrophoresis etc. The microarray can be manufactured by any method known in the art including by photolithography, pipette, drop-touch, piezoelectric (ink-jet), and electric techniques.

As used herein the term "and/or" means that in an embodiment it is the conjunctive "and", and in another embodiment it is the disjunctive "or". For example, "TXNDC14 and/or CTNND1" includes the embodiments of "TXNDC14 and CTNND1" and the embodiment "TXNDC14 or CTNND1".

In regard to the methods herein involving ratios, it is understood that determining ratios can confer significant advantages over simply determining absolute amounts. For example, if a particular mRNA transcript is increased in expression in a metastatic cancer cell relative to a normal cell that may be because, inter alia, it is metastasis-associated or it msay be because the metastatic cancer cell has increased expression of all or many genes, period. However, the ratio of a given transcript to one or more others is not susceptible in the same way as absolute amounts are to the problem of the global increased expression of genes, and as such rationing can reveal patterns and associations otherwise not discernible.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Using an established cell culture model and an RNA-Seq analysis, an alternative splicing signature of EMT was determined to exist. It was found that thousands of multi-exon genes underwent alternative splicing during EMT. Many of the alternatively spliced genes showed enrichment in functions important for EMT-driven changes in cell phenotype like actin cytoskeleton remodeling, regulation of cell-cell junction formation and regulation of cell migration. The analysis demonstrated that most of the EMT-associated alternative splicing is regulated by Fox, MBNL, CELF, hnRNP and ESRP classes of splicing factors. The alternative isoform expression was confirmed in human breast cancer cell lines, which could be classified into basal and luminal subtypes based exclusively on their EMT-associated splicing pattern.

Expression of EMT-associated alternative mRNA transcripts was also validated in primary breast cancer samples, indicating that EMT-dependent splicing changes occur commonly in human tumors. Expression of the epithelial-specific splicing factor ESRP1 in mesenchymal cells shifted their morphology and motility towards an epithelial phenotype, suggesting that splicing regulation alone can drive critical aspects of EMT-associated phenotypic changes. Since EMT is considered an early step in metastatic progression, the molecular description obtained herein provides new diagnostic and prognostic markers for analysis of breast cancer progression.

Using an established in vitro model of EMT, the amount of gene expression and alternative splicing changes during EMT was evaluated. Using deep sequencing analysis of the transcriptomes of epithelial and mesenchymal cells, it was discovered that a global alternative splicing program that alters splicing of key regulators of cell phenotype including proteins that control cell adhesion and cytoskeletal dynamics exists. The analysis indicates that EMT-associated splicing is likely regulated by several splicing factors including the ESRPs and members of the Fox, CELF, MBNL, and hnRNP classes of splicing factors. Supporting a key role for alternative splicing during EMT, it was found that partial induction of the epithelial splicing program via ectopic expression of ESRP1 conferred epithelial junctional, barrier and migration properties to mesenchymal cells. Multiple EMT-associated alternative splicing events were confirmed in breast cancer cell lines and in primary human breast cancer samples. This EMT-associated splicing signature likely represents a broadly conserved program involved in the acquisition of mesenchymal-like phenotypes in vivo that could be used to detect EMT in primary human cancers with potentially significant prognostic value.

Large-scale changes in gene expression accompany EMT: To assess gene and alternative mRNA isoform expression during EMT an in vitro model was used in which mammary epithelial cells (HMLE) expressing Twist fused to a modified estrogen receptor (ER) undergo EMT when the fusion protein is activated by addition of the ER ligand 4-hydroxytamoxifen (4-OHT; tamoxifen) [32]. Untreated HMLE/Twist-ER epithelial cells maintained highly organized cell-cell adhesions and cell polarity (FIG. 1A). Following tamoxifen treatment, the cobblestone-like appearance of HMLE/Twist-ER cells was replaced by a spindle-like, fibroblastic morphology, consistent with previously published results (FIG. 1A; [32]). This morphological transformation represents one of the hallmarks of an EMT. As expected, phenotypic changes coincided with the loss of E-cadherin and an onset of N-cadherin, Fibronectin and Vimentin expression (FIG. 1B). Tamoxifen competes with estrogen for binding to ER to form a complex that translocates into the nucleus where it recruits co-repressors of transcription, thus preventing activation of ER downstream targets [33]. Since HMLE cells do not express any endogenous ER (FIG. 7B), EMT induction in HMLE/Twist-ER cells is likely initiated exclusively by downstream targets of Twist, making HMLE/Twist-ER cells a useful in vitro model of EMT.

To obtain an in-depth analysis of gene expression and splicing changes during EMT, mRNA was collected from untreated (epithelial) and from tamoxifen-treated (mesenchymal) HMLER/Twist-ER cells. Deep sequencing of fragments of polyA-selected mRNAs (RNA-Seq) was used to obtain a digital inventory of gene and mRNA isoform expression (FIG. 1A).

Between 27 million and 30 million 39-base-pair (bp) cDNA fragments were sequenced from each sample. Sequenced cDNA fragments (reads) were mapped to the human genome (hg18 version) and to a splice junction database derived from AceView annotation [34]. In total, 75% of reads mapped uniquely to the genome or to splice junctions, allowing up to 2 mismatches. Less than 1% of total reads mapped uniquely to rRNA sequences (Data not shown). Read density (coverage) was over 400-fold higher in exons than in introns or intergenic regions (FIG. 7C), indicating that most reads derived from mature mRNA.

Figures 8A, 8B, 8C:
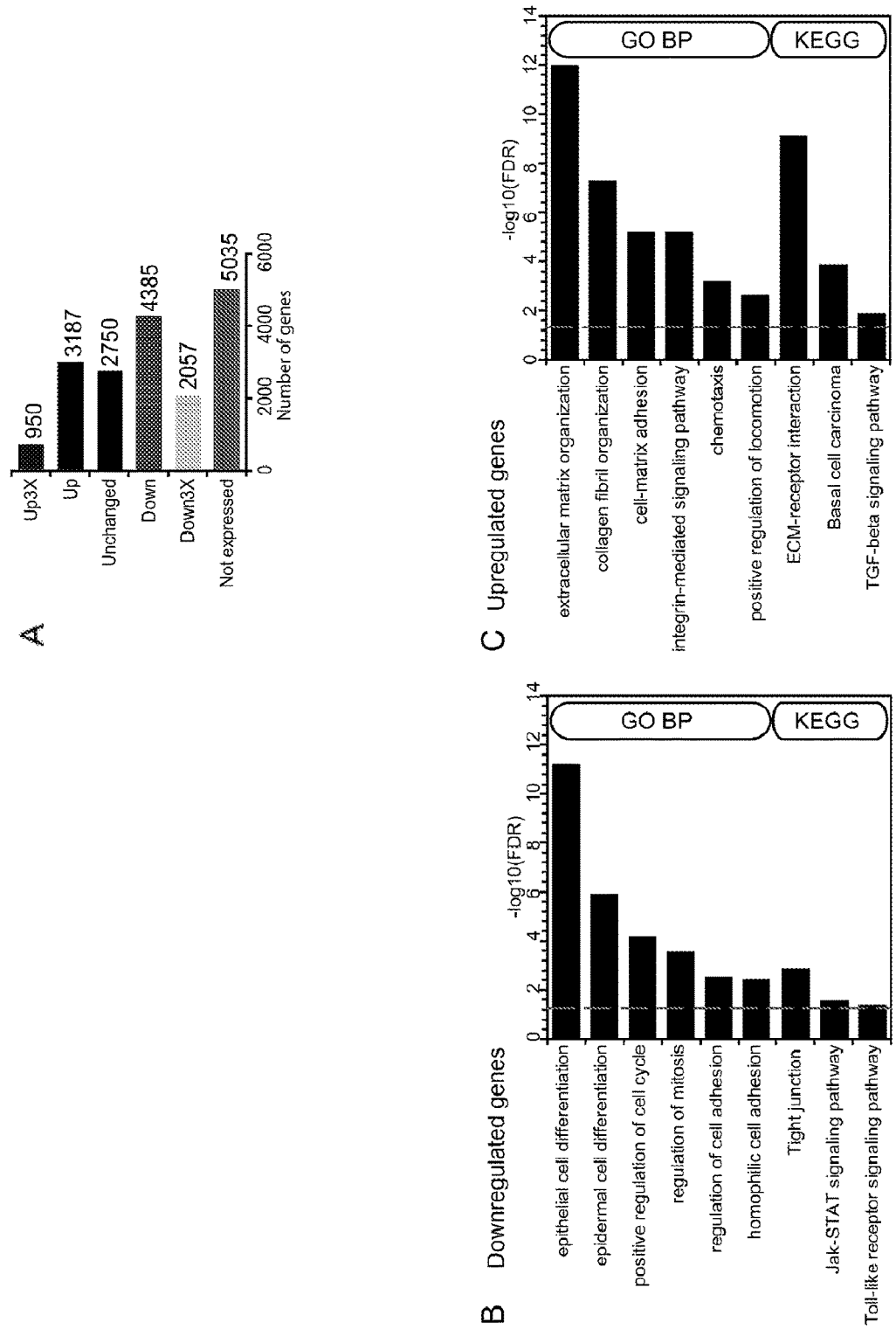
FIG. 8A-8C: EMT is accompanied by a massive change in gene expression. (8A) Gene expression during EMT. (8B) and (8C) Gene ontology enrichment analysis of genes down-regulated (8B) and upregulated in EMT. Gene ontology 'biological process', GO_BP_FAT, annotation is depicted in red on the y axis. KEGG Pathway analysis (www.genome.jp/kegg/) annotation is also depicted on y axis. Benjamini FDR (−log 10) is indicated on the x axis. Vertical dotted line marks Benjamini FDR=0.05.

First, gene expression changes during EMT was estimated using "Reads Per Kilobase of Exon Model per Million Mapped Reads" (RPKM), a measure of expression that reflects the molar concentration of a transcript in the sample by normalizing read counts for mRNA length and for the total read number in the sample [35]. Applying both a statistical cut-off based on Audic-Claverie statistics for read-based expression profiling [36] and an arbitrary cut-off of 3-fold changes, it was observed that ~2,060 genes were downregulated, while ~950 were upregulated in EMT (FIG. 8A), indicating a large-scale reorganization of the transcriptome during this process in agreement with recently published data [37]. As expected, E-cadherin was downregulated, while N-cadherin was upregulated during EMT [19]; actin transcript levels remained unchanged (FIG. 8A). These observations revealed that Twist-induced EMT is accompanied by massive changes in gene expression similarly to developmental EMT, as has been previously shown by the genomic profiling of the mouse palate closure stages [38].

A gene ontology (GO) enrichment analysis of up- and down-regulated genes provided clues to the functional significance of these expression changes. Genes involved in epithelial cell differentiation, encoding components of cell cycle machinery and cell-cell junction components were downregulated during EMT (FIG. 9B). Concomitantly, genes associated with cell-matrix adhesion, extracellular matrix organization and cell motility were upregulated (FIG. 8C). Thus, the most significant EMT-driven changes in gene expression are associated with gene categories involved in the phenotypic conversion that occurs during EMT, in agreement with previously published data [38].

Alternative isoform expression is grossly affected in EMT: To explore the extent of regulated RNA processing during EMT, eight common types of alternative isoform expression events were examined, each capable of producing multiple mRNA isoforms from a gene through alternative splicing, alternative cleavage and polyadenylation (APA) and/or alternative promoter usage (FIG. 1D; [23]). These eight types of events included: skipped exons (SE), retained introns (RI), mutually exclusive exons (MXEs), alternative 5' and 3' splice sites (A5SS and A3SS), alternative first exons (AFE), alternative last exons (ALE) and tandem 3' untranslated regions (tandem 3' UTR5). A comprehensive set of ~136,000 events of these eight types was derived from the AceView gene annotations [34]. The fraction of mRNAs that contained an alternative exon—the "percent spliced in" (PSI or $\Psi$) value—was estimated by the ratio of the density of inclusion reads to the sum of the densities of inclusion reads and exclusion reads, with a variant of this method used for tandem 3' UTRs, as described previously [23]. Thus, $\Psi$ values range from ~0, indicating predominant exclusion of an alternative exon from mRNAs to ~1, indicating predominant inclusion of the exon. The extent of EMT-specific regulation of these events was assessed by comparison of the mesenchymal (post-EMT) to the epithelial (pre-EMT) RNA-Seq data (FIG. 1D).

In all, for ~40% of genes with documented alternative isoforms, both isoforms were detected by RNA-Seq reads. Of the events where both isoforms were detected, about 1 in 10 skipped exons (SE) and 1 in 20 mutually exclusive exons (MXE) exhibited a significant change in $\Psi$ value >10%, with hundreds of other splicing-related events also regulated at this level (FIG. 1D). At the gene level, 4.5% of genes contained an event(s) with an absolute change in $\Psi$ value greater than 10% during EMT, and 2% of genes contained an event(s) with a $\Psi$ value change greater than 30%. The data obtained indicate that a substantial change in splicing accompanies EMT.

Figures 7A, 7B, 7C, 7D:
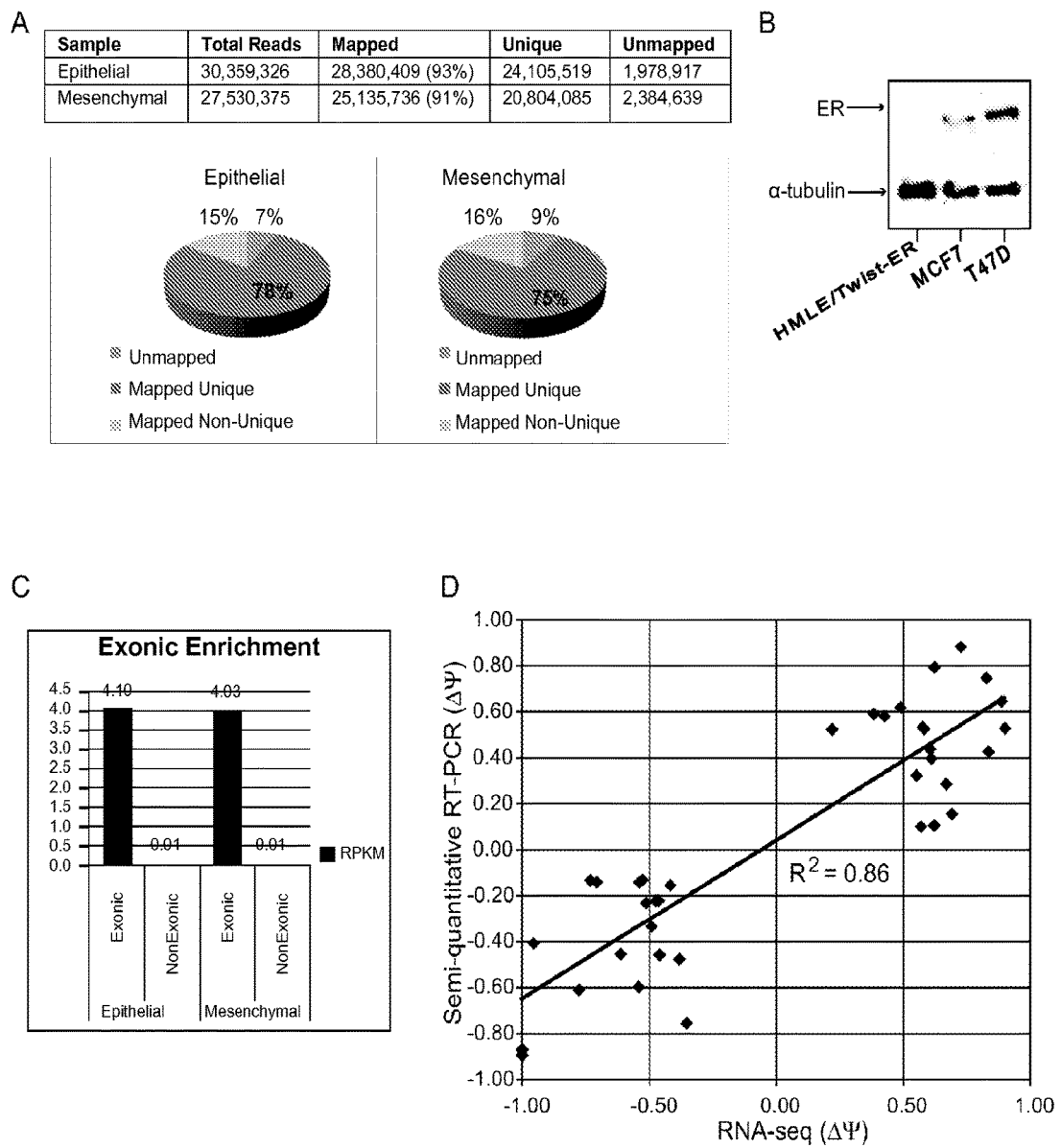
FIG. 7A-7D: (7A) 39-base-pair (bp) cDNA fragments were sequenced from each sample; (7B) HMLE cells do not express any endogenous ER; (7C) Read density (coverage) was over 400-fold higher in exons than in introns or intergenic regions; (7D) Change in splicing $\Delta\Psi$ ($=\Psi M-\Psi E$) detected by RT-PCR in the same direction as that determined by RNA-Seq.

To confirm the ability of the RNA-Seq to correctly detect changes in alternative splicing during EMT, a subset of SE and MXE events was chosen from the FDR<0.05 and $|\Delta\Psi|>0.1$ set of splicing events for semi-quantitative RT-PCR (sqRT-PCR) analysis using cDNA from HMLE/Twist-ER cells before and after EMT induction by tamoxifen treatment. Alternative splicing events with $|\Delta\Psi|>0.1$ have been previously suggested to be functionally important, since they are enriched for evolutionarily conserved sequences surrounding the alternative exons compared to constitutive exons [23]. The tested subset included 37 alternative exons that showed relatively large changes in splicing based on the analysis of the RNA-seq data or whose host genes encoded functionally interesting molecules with respect to EMT (e.g., adhesion molecules). This subset also included a few events that showed relatively small changes in isoform expression in order to assess the robustness of our statistical test. In all cases, the change in splicing $\Delta\Psi$ ($=\Psi M-\Psi E$) detected by RT-PCR was in the same direction as that determined by RNA-Seq (FIG. 7D), and in 78% of cases, the change in $\Psi$ observed by sqRT-PCR was 20% or more. Altogether, a strong concordance ($R^2=0.86$; FIG. 7D) was observed between splicing changes detected by RNA-Seq and measurements by sqRT-PCR. The high validation rate and quantitative concordance by an independent method (sqRT-PCR) support the reliability of the alternative splicing events identified by the RNA-seq analysis.

The genes with altered splicing during EMT showed strong functional enrichment. Analyses of alternatively spliced genes showed preferential enrichment of biological processes related to the regulation of the actin cytoskeleton, cell-cell junctions, regulation of cell migration and wound healing. The KEGG pathway enrichment analysis implicated EMT-associated alternative splicing in aspects of signaling involving Wnt, Ras and Insulin pathways (FIG. 1C). These enriched terms suggested that alternative splicing plays important roles in processes crucial for the morphological and motility-related changes associated with EMT.

Figures 2A, 2B, 2C:
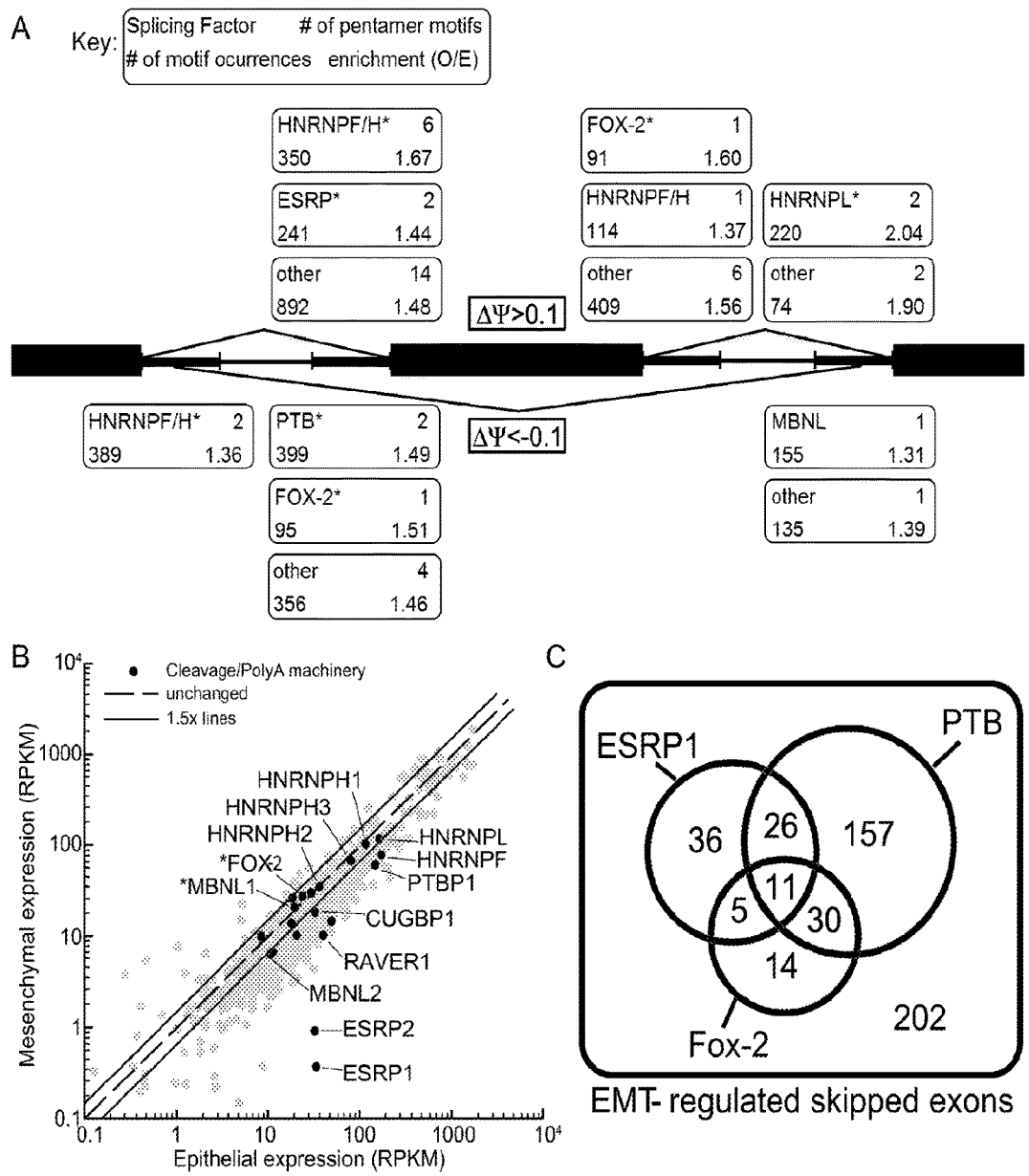
FIG. 2A-2C. Motif analysis reveals splicing factors that are involved in the regulation of EMT-specific splicing. (2A) Pentamer motifs significantly enriched (FDR<0.1) in the 4 flanking 250-nt intronic regions of EMT-regulated skipped exons. Statistics of motifs resembling known binding sites of splicing factors are annotated as described in the key. Motifs that are not recognized as known binding sites are grouped into the "Other" group. *=at least one known motif of that splicing factor has an FDR<0.05. (2B) Scatter plot of expression levels of RNA binding proteins and mRNA splicing regulators in epithelial and mesenchymal cells. Some splicing factors whose motifs were enriched in (2A) are highlighted. Asterisks mark splicing factors which are also regulated by alternative splicing of their mRNA transcripts. Genes encoding components of cleavage/polyadenylation machinery are also highlighted. (2C) A Venn diagram showing potential regulation of EMT-associated skipped exon events by ESRP1, PTP and FOX splicing factors based on the microarray analysis of ESRP1 depleted MDA-MB-231 cells (Carstens R., personal communication) and CLIP-Seq analysis of FOX and PTB [30,39] (See Methods). The universe of the Venn diagram consists of all EMT-regulated SE events by FDR of 5% and $|\Delta\Psi|>=10\%$. P(RBFOX2)=8.58e-05; p (PTB)=0.0013; p (ESRP1)=9.27e-16.

Regulatory motifs and factors associated with the EMT splicing program: A substantial shift in the levels or activity of the major splicing factors is likely to underlie the large-scale program of splicing changes that occur during EMT. To explore the nature of this shift, the incidence of oligonucleotide motifs occurring in regulated alternative transcripts was analyzed, and changes in the expression of RNA binding protein (RBP) genes examined. As most splicing factors bind short RNA oligomers a few bases long, pentanucleotides (5mers) were identified that were enriched in regions adjacent to the splice sites involved in splicing of exons induced or repressed upon EMT (FIG. 2A). These analyses identified a few dozen 5mers enriched in each region relative to control alternative introns, including motifs corresponding to the Fox, CELF, ESRP and MBNL families of tissue-specific factors, and motifs for several heterogeneous nuclear ribonucleoprotein (hnRNP) factors, including hnRNPs F and H, PTB/hnRNP I, and hnRNP L (Tables 3 and 4). A subset of these motifs was specifically enriched adjacent to exons whose Ψ values increased following EMT relative to exons whose splicing did not change (FIG. 2A). These included motifs associated with Fox and ESRP families of splicing factors and with hnRNPs F/H and L. An overlapping subset of motifs were enriched adjacent to exons whose Ψ values decreased following EMT, again including motifs associated with the Fox and hnRNP F/H families and also motifs associated with PTB and MBNL family proteins (FIG. 2A). Several 5-mers of unknown cognate RNA binding proteins were identified from the motif analysis.

TABLE 1

The 5-mer motif enrichment analysis on alternative splicing events with FDR < 0.05, ΔΨ > 0.1.

| Exon | Element | p-value | FDR | background rate | Expected freq | Foreground rate | foreground freq | word |
|---|---|---|---|---|---|---|---|---|
| inDFSeq | I3 | 1.30E-13 | 1.33E-10 | 0.000979829 | 50 | 0.00211628 | 110 | CACAC |
| inDFSeq | I3 | 4.95E-10 | 2.53E-07 | 0.00112502 | 58 | 0.00211628 | 110 | ACACA |
| inDFSeq | I3 | 0.000120232 | 0.0409589 | 0.000462737 | 24 | 0.000846512 | 44 | CUAGC |
| inDFSeq | I3 | 0.000332771 | 0.0850231 | 0.000289658 | 15 | 0.000577167 | 30 | CGUGC |
| inMFSeq | I3 | 5.57E-07 | 0.000570035 | 0.00059723 | 31 | 0.00117518 | 61 | GCGGG |
| inMFSeq | I3 | 1.87E-06 | 0.00095860 | 50.00067513 | 35 | 0.00125224 | 65 | GGCGG |
| inMFSeq | I3 | 1.96E-05 | 0.0066868 | 90.00169082 | 87 | 0.00246595 | 128 | GGUGG |
| inMFSeq | I3 | 4.20E-05 | 0.0107292 | 0.000174775 | 9 | 0.0004431 | 23 | CGCCG |
| inMFSeq | I3 | 6.06E-05 | 0.0124036 | 0.000608216 | 31 | 0.00105959 | 55 | GGGCG |
| inMFSeq | I3 | 0.000162306 | 0.0276732 | 0.000617204 | 32 | 0.00104032 | 54 | CGGGG |
| inMFSeq | I3 | 0.000270332 | 0.039507 | 0.000630188 | 32 | 0.00104032 | 54 | CCCGG |
| inMFSeq | I3 | 0.00027288 | 0.0348945 | 0.000136824 | 7 | 0.000346774 | 18 | UCGGA |
| inMFSeq | I3 | 0.00027877 | 0.0316868 | 0.00155599 | 80 | 0.00217697 | 113 | UGGUG |
| inMFSeq | I3 | 0.000316934 | 0.0324223 | 0.000560278 | 29 | 0.000943996 | 49 | CCGGG |
| inMFSeq | I3 | 0.000316946 | 0.0294759 | 0.00099743 | 10 | 0.0004431 | 23 | AGCGC |
| inMFSeq | I3 | 0.000368174 | 0.0313868 | 0.000505349 | 26 | 0.000866935 | 45 | GCCCG |
| inMFSeq | I3 | 0.000441672 | 0.0347562 | 0.0013163 | 68 | 0.00186873 | 97 | GGGGC |
| inMFSeq | I3 | 0.000583398 | 0.0426297 | 0.00349849 | 181 | 0.00435394 | 226 | UCUUU |
| inMFSeq | I3 | 0.000667352 | 0.0455134 | 0.000360535 | 18 | 0.000655018 | 34 | GCCGC |
| inMFSeq | I3 | 0.000750919 | 0.0480119 | 0.00209929 | 108 | 0.00275493 | 143 | CUUUC |
| inMFSeq | I3 | 0.00103113 | 0.0620495 | 0.000230703 | 11 | 0.000462365 | 24 | CCGGU |
| inMFSeq | I3 | 0.00126113 | 0.0716745 | 0.000247681 | 12 | 0.000481631 | 25 | UUCCG |
| inMFSeq | I3 | 0.00131331 | 0.0707115 | 0.000168782 | 8 | 0.000366039 | 19 | CGGAA |
| inMFSeq | I3 | 0.00162337 | 0.0830352 | 0.00241489 | 125 | 0.00306317 | 159 | UUUCC |
| inMFSeq | I3 | 0.00197592 | 0.0962556 | 0.000384504 | 19 | 0.000655018 | 34 | CCGUG |
| inMFSeq | I3 | 0.00197592 | 0.0918803 | 0.000384504 | 19 | 0.000655018 | 34 | CGGGA |
| inMFSeq | I5 | 1.65E-05 | 0.0168813 | 0.00110678 | 57 | 0.00175074 | 91 | GCAUG |
| inMFSeq | I5 | 2.02E-05 | 0.0103411 | 0.000213136 | 11 | 0.000519451 | 27 | ACCGU |
| inMFSeq | I5 | 4.43E-05 | 0.0150921 | 0.00116795 | 60 | 0.00178922 | 93 | GGCUU |
| inMFSeq | I5 | 9.09E-05 | 0.0232482 | 0.000868792 | 45 | 0.0013852 | 72 | ACUAA |
| inMFSeq | I5 | 0.000112722 | 0.0230629 | 0.000210269 | 10 | 0.000480973 | 25 | UUCCG |

TABLE 1-continued

The 5-mer motif enrichment analysis on alternative splicing events with FDR < 0.05, ΔΨ > 0.1.

| Exon | Element | p-value | FDR | background rate | Expected freq | Foreground rate | foreground freq | word |
|---|---|---|---|---|---|---|---|---|
| inMFSeq | I5 | 0.00044314 | 0.0755553 | 0.00144321 | 75 | 0.00202009 | 105 | CCCCA |
| inMFSeq | I5 | 0.000534133 | 0.0780597 | 0.00159804 | 83 | 0.00219324 | 114 | GGGUG |
| inMFSeq | I5 | 0.000755347 | 0.0965901 | 0.00117464 | 61 | 0.00167379 | 87 | GCCCC |

TABLE 2

The 5-mer motif enrichment analysis on alternative splicing events

| Exon | Element | p-value | FDR | background rate | expected foreground freq | foreground rate | foreground freq | word |
|---|---|---|---|---|---|---|---|---|
| inDFSeq | I3 | 3.22E-06 | 0.00329109 | 0.00175271 | 97 | 0.00243107 | 135 | CUUUC |
| inDFSeq | I3 | 4.51E-05 | 0.0230923 | 0.00214287 | 118 | 0.00279123 | 155 | CUGCC |
| inMFSeq | I3 | 8.86E-09 | 9.08E-06 | 0.00207539 | 113 | 0.00321004 | 176 | CUCUC |
| inMFSeq | I3 | 5.32E-08 | 2.73E-05 | 0.00283303 | 155 | 0.00406726 | 223 | UCUCU |
| inMFSeq | I3 | 6.43E-05 | 0.02 938 | 0.00180733 | 99 | 0.00251696 | 138 | UCUUC |
| inMFSeq | I3 | 6.78E-05 | 0.0173448 | 0.005833 | 63 | 0.001732691 | 95 | UGCAU |
| inMFSeq | I3 | 0.000167073 | 0.0342165 | 0.000479697 | 26 | 0.000838987 | 46 | ACAAC |
| inMFSeq | I3 | 0.000208215 | 0.0355353 | 0.000595388 | 32 | 0.000984898 | 54 | CAACU |
| inMFSeq | I3 | 0.000576154 | 0.0842831 | 0.00158864 | 87 | 0.00215219 | 118 | CCCCC |
| inUFSeq | I5 | 3.32E-06 | 0.00339913 | 0.00311114 | 170 | 0.0041767 | 229 | CGGGG |
| inUFSeq | I5 | 4.05E-05 | 0.0207318 | 0.00214085 | 117 | 0.00291822 | 160 | GGGGU | with FDR <0.05, ΔΨ < −0.1.

For Tables 1 and 2: The 5-mers enriched in foreground set over background set of unchanged exons in 250 nt flanking intronic sequences of skipped exons and upstream and downstream exons.
Table 1: FDR<0.05, ΔΨ>0.1.
Table 2: FDR<0.05, ΔΨ<−0.1.
Annotation details: [ ] are the two flanking exons, < > is the skipped exon:
[inUFSeq] I5 - - - I3<in MFSeq >I1 - - - I3 [in DFSeq].
Column 1 (Exon) indicates a reference exon of the intronic element analyzed. Column 2 (Element) indicates intronic element analyzed: I5-5' sequence of the intron, I3-3' sequence of the intron. Column 3 (p-value)—the hypergeometric p-value of the 5-mer frequency in foreground over that of the background. Column 4 (FDR)—B-H multiple comparison FDR of the p-value. Column 5 (background rate)—the density of the 5-mer in the background (set of unchanged SE events). Column 6 (expected frequency)—the expected count of the 5-mer in the foreground given the background rate. Column 7 (foreground rate)—the density of the 5-mer in the foreground (set of changed SE events). Column 8 (foreground frequency)—the count of the 5-mer in the foreground. Column 8 (word) demonstrates the sequence of the 5-mer.

The most striking changes in RBP expression occurred for the related epithelial specific splicing factors ESRP1 (RBM35A) and ESRP2 (RBM35B) [27]. During EMT, the expression of these factors decreased by ~90-fold and ~35-fold, respectively, from relatively high initial levels (FIG. 2B). Motif enrichment for ESRP splicing factors was observed in upstream sequence of cassette exons upregulated during EMT (FIG. 2A) consistent with the recent observation that ESRP binding sites are present at greater numbers upstream of silenced exon than the enhanced exons [31]. As ESRPs are downregulated during EMT, these silenced exons are relaxed from ESRP inhibition and thus appear up-regulated during EMT.

The pattern of motif enrichment for Fox family factors— enriched downstream of exons whose inclusion increased during EMT, and upstream of exons whose inclusion decreased (FIG. 2A)—suggested that Fox proteins may play a role in both activation and repression of splicing during EMT. Recently, it has been suggested that RBFOX2 activity plays a role in regulating a set of breast cancer subtype— specific alternative splicing events [29]. Splicing factor activity often switches between positive and negative regulation depending on the location of binding relative to the regulated exon. Since Fox family splicing factors tend to enhance splicing when bound downstream and to repress splicing when bound upstream of alternative exons [30], the observed patterns of enrichment of Fox motifs are consistent with an increase in the activity of Fox family factors during EMT.

The expression levels of many other RBPs changed during EMT (FIG. 2B). Among well known and highly expressed splicing factors, these changes included downregulation of the splicing repressor PTBP1 (PTB/hnRNP I) by ~2.5-fold, downregulation of the PTB-associated splicing co-repressor RAVER1 by ~4-fold, and downregulation of the myotonic dystrophy-associated splicing factors MBNL2 and MBNL3 and of hnRNP F by ~1.6- to 2.5-fold, all factors associated with motifs enriched near EMT-regulated exons (FIG. 2B). These observations suggested that changes in the levels and activity of several different splicing factors may contribute to the splicing changes observed in EMT.

Figures 3A, 3B, 3C, 3D:
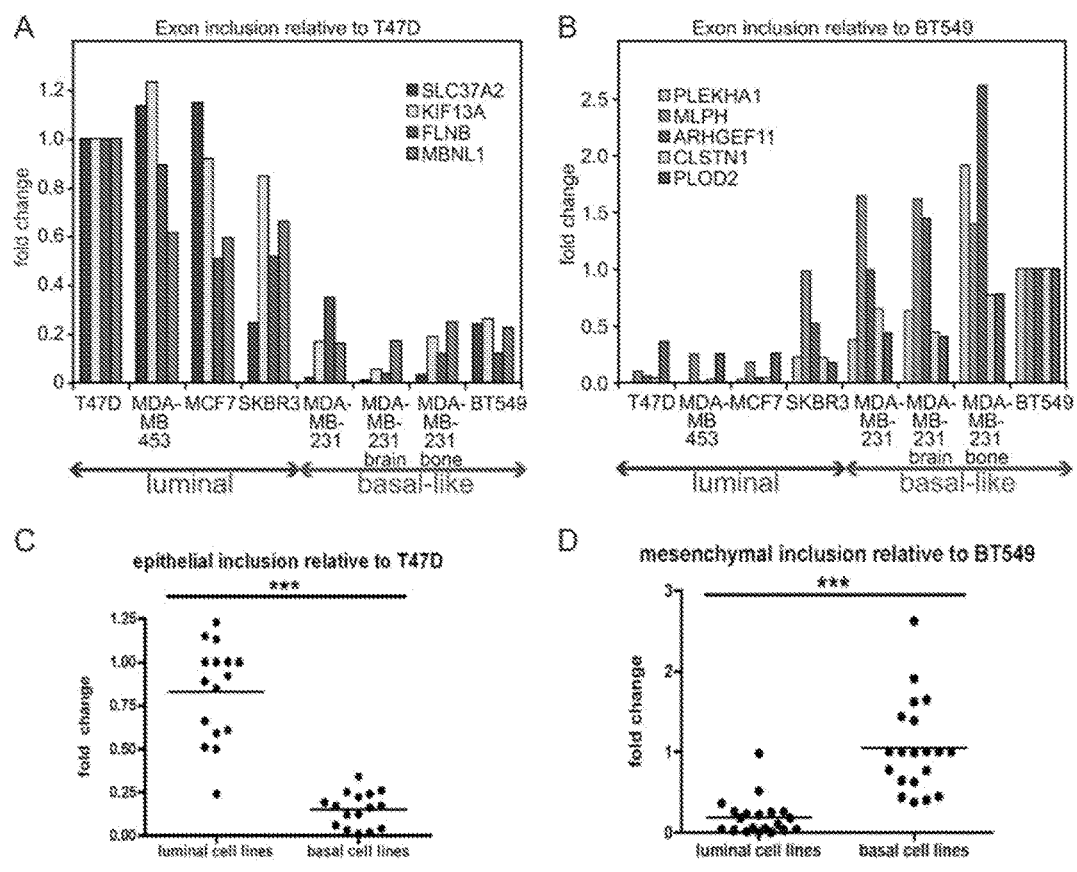
FIG. 3A-3D. EMT-associated alternative splicing events are confirmed in breast cancer cell lines. (3A) Alternative exon inclusion in 4 mRNA transcripts, as indicated, in 8 breast cancer cell lines determined by a qRT-PCR analysis and depicted as a fold change relative to exon inclusion in T47D luminal cell line. (3B) Alternative exon inclusion in 5 mRNA transcripts, as indicated, in 8 breast cancer cell lines depicted as a fold change relative to exon inclusion in BT549 basal B cell line. (3C) Distribution of all epithelial inclusion events combined. Each event is depicted as a fold change relative to inclusion in T47D. (3D) Distribution of all mesenchymal inclusion events combined. Each event is depicted as a fold change relative to inclusion in BT549 cells. For (3C) and (3D), ***=p<0.001.

To explore the potential contributions of splicing factors to splicing of EMT-regulated alternative exons, published cross-linking/immunoprecipitation-sequencing (CLIPSeq) data from human cell lines was analyzed. In addition, a significant fraction of the observed EMT-regulated splicing events overlapped with a set of ESRP1-regulated exons recently identified by Carstens and coworkers using RNAi and a splicing-sensitive microarray analysis (FIG. 3C; [31]). Dozens of EMT-regulated skipped exons were associated with Fox-2 CLIP-Seq clusters, and hundreds were associated with PTB CLIP-Seq clusters (FIG. 2C, [30,39]). Together, the RNAi and CLIP-Seq data demonstrate the potential for regulation of a substantial portion—perhaps a majority of EMT-regulated exons—by these three factors. Thus, the data disclosed herein are consistent with a model in which several splicing factors collaborate in the regulation of splicing during EMT, potentially adding an additional level of post-transcriptional regulation to the EMT program.

EMT-associated alternative transcripts are expressed in breast cancer cell lines: Alternatively spliced mRNA isoforms that exhibit EMT-associated changes in exon inclusion can serve as valuable prognostic markers for metastatic disease, since EMT is considered an early event in metastatic progression. As an initial step towards eventual analysis of primary human samples, alternative isoform expression in a panel of human breast cancer cell lines of luminal (generally poorly metastatic) and basal-like origin (generally aggressive and metastatic) was assessed. Luminal cell lines, like MCF7 and T47D, have been shown to express high levels of epithelial markers including E-cadherin, while basal-like cell lines have been demonstrated to express mesenchymal markers including N-cadherin, vimentin and fibronectin [15]. In addition, in the analysis two cell lines were used—derivatives of MDA-MB-231 cell metastases to the brain and bone—that exhibited a more aggressive phenotype compared to the parental MDA-MB-231 cells [40]. It was hypothesized that splicing events with high inclusion ratio in the pre-EMT/epithelial sample (epithelial inclusion) would be expressed in luminal breast cancer cell lines, and conversely that splicing events with high inclusion ratio in the post-EMT/mesenchymal sample (mesenchymal inclusion) would be expressed in basal-like cell lines. A quantitative RT-PCR (qRT-PCR) analysis of 9 skipped exons, that demonstrated the largest change in the inclusion ratio ($\Delta\Psi$) in the validated set of 37 alternative splicing events, using cDNA from the panel of luminal and basal-like cell lines, indicated that 4 epithelial inclusion events, in the SLC37A2, KIF13A, FLNB, and MBNL1 genes, were included at high frequency in luminal cell lines, whereas inclusion of these events was low in basal-like cells compared to T47D epithelial cells (FIG. 3A). Conversely, 5 mesenchymal-enriched inclusion events in PLEKHA1, MLPH, ARHGEF11, CLSTN1, PLOD2, were observed enriched in basal-like cell lines with only low inclusion levels in luminal cells relative to BT549 mesenchymal cells (FIG. 3B), in agreement with recently published results [31]. Thus, taken together, epithelial inclusion events were confirmed in corresponding mRNA transcripts in luminal cells and were detected at very low levels in basal-like cells, while mesenchymal inclusion events were detected at low levels in luminal cells but showed high inclusion ratio in basal-like cells (FIG. 3C,D). Therefore, the qRT-PCR analysis of skipped exons using cDNA from a panel of luminal and basal-like breast cancer cell lines detected EMT-associated splicing events, as predicted by the RNA-seq analysis of Twist-induced EMT.

To explore the expression of EMT-associated alternative splicing events in breast cancer cell lines further and to determine whether EMT-associated alternative exons could classify breast cancer cell line subtypes, the expression of SEs from the EMT RNA-seq analysis was compared to available exon array data from luminal and basal B breast cancer cell lines in the NCI-60 panel [41]. Unsupervised hierarchical clustering of exon array data on 307 EMT-associated SE events ($|\Delta\Psi|>0.1$, FDR<0.05; foreground set) detected by the array, segregated basal B cell lines from luminal cell lines with only 2 outliers, MDA-MB-436 and SUM149, basal cell lines misclassified in the luminal cluster. In contrast, clustering of the exon array data using the background set of 8839 events resulted in cell line subtype classification with 9 outliers indicating the whole set of analyzed events is not intrinsically biased and that the SE events identified by our EMT RNA-seq conferred sufficient discriminative power to classify the luminal and basal B cell lines. Furthermore, a randomization-clustering procedures demonstrated that the clustering classification using our set of SE events was statistically significant (p-value=0.0014). Thus, the EMT-associated splicing program identified by the RNA-seq analysis is conserved in breast cancer cell lines and correlates with their invasive and metastatic properties.

Figures 4A, 4B, 4C:
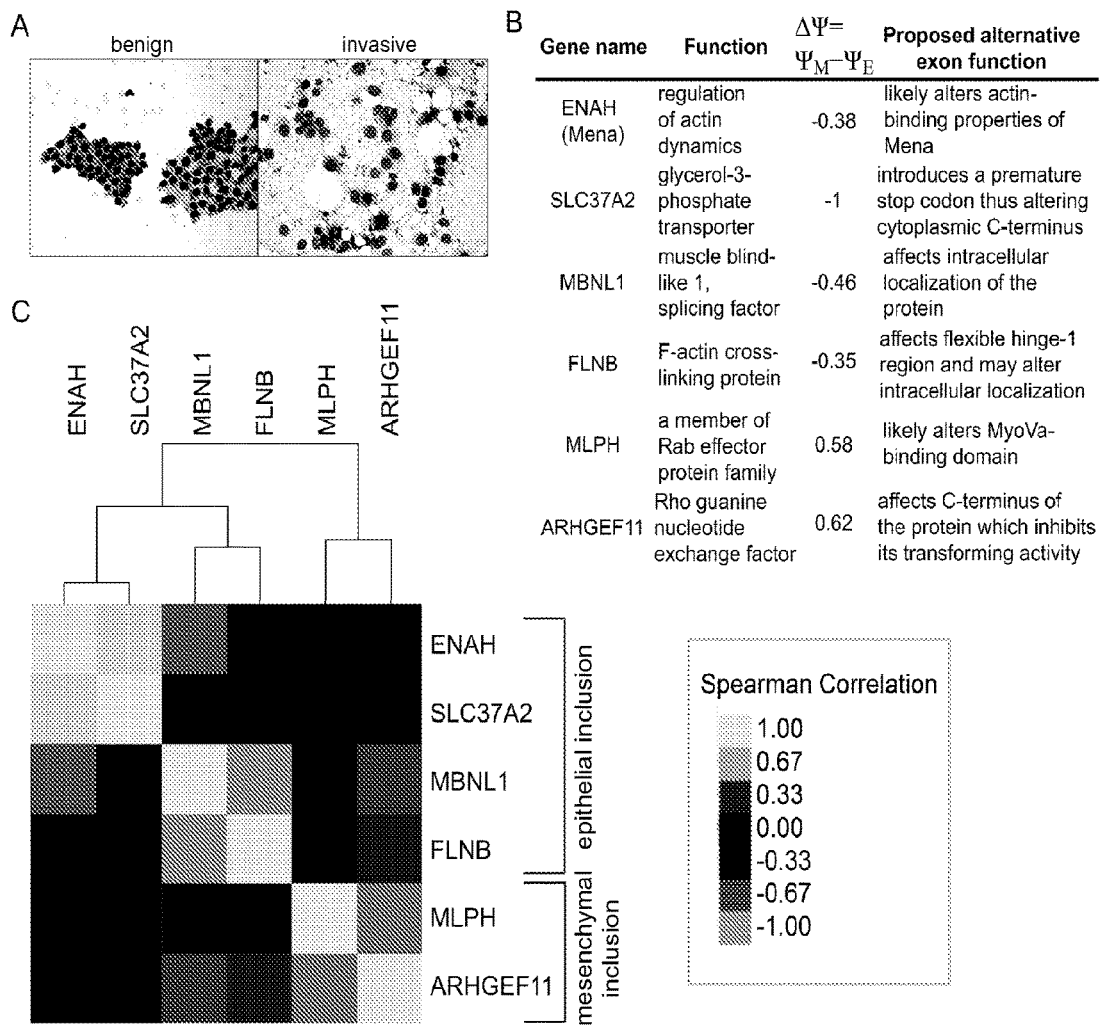
FIG. 4A-4C. Alternative mRNA isoforms are expressed in FNA samples from breast cancer patients. (4A) An example of a fine needle aspiration (FNA) spread from a benign and an invasive human breast tumor. (4B) A table describing gene names, gene functions, change in inclusion levels during EMT ($\Delta\Psi$) and proposed functions of 6 SE events used in the FNA qRT-PCR analysis in (4C). (4C) Spearman correlation analysis of fold change in exon inclusion ratios compared to an average fibroadenoma samples for 6 alternative splicing events depicted as a heat plot of pairwise correlation. Lightest gray indicates a correlation of 1, black indicates a correlation of 0.
Figure 9:
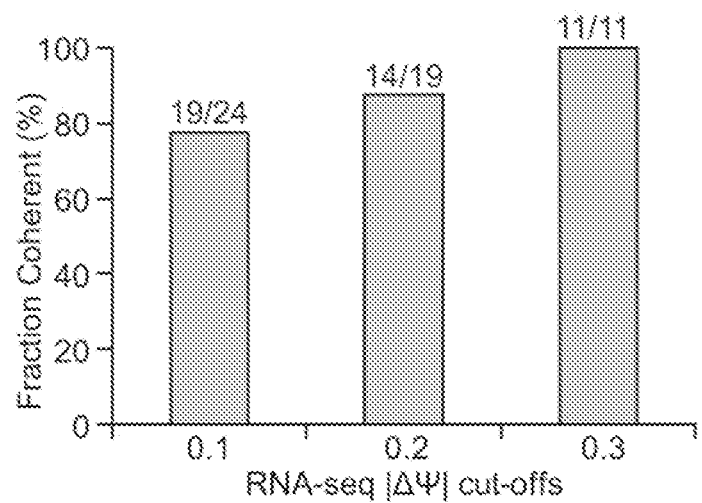
FIG. 9: Coherence between NCI-60 array data and EMT RNA-Seq dataset increases for highly changed EMT-associated SE events. A bar graph demonstrating the fraction of coherent events between EMT RNA-seq and a panel of NCI-60 breast cancer cell lines [41] as a function of RNA-seq |ΔΨ| cut-offs. The number of events called significant at the corresponding RNA-seq |ΔΨ| cut-offs and exon array FDR<0.25 is depicted above each column.

Possibly due to the heterogeneity of cancer cell lines, the correlation between samples was not high (FIG. 4A). To find a "core" EMT alternative splicing signature that can unambiguously distinguish between breast cancer cell line subtypes, EMT-driven SE events were compared to the SE events that were differentially regulated between the luminal and basal B cell lines. Of the SE events that changed significantly in the EMT RNA-Seq dataset ($|\Delta\Psi|>0.1$, FDR<0.05) and were represented on the array, a total of 28 events changed significantly between luminal and basal B cell lines with an FDR<0.25. Of these, 19 (79%) changed in a coherent manner in the sense that the change in exon inclusion was in the same direction between mesenchymal and epithelial sample in EMT RNA-seq dataset as between basal B and luminal cell lines in the exon array dataset (FIG. 9). Interestingly, coherence increased for events that changed more dramatically in the EMT RNA-Seq dataset, with 100% (11) of SE events (RNA-seq $|\Delta\Psi|>0.3$) exhibiting coherence between the two datasets (FIG. 9). Notably, clustering analysis of luminal and basal B breast cancer cell lines using 19 coherent SE events demonstrated that luminal cell lines could be unambiguously distinguished from basal B cell lines based exclusively on these splicing events alone. These "core" EMT-associated alternative splicing events may comprise a common program that contributes to the phenotypic changes that endow cancer cells with invasive and metastatic capabilities.

Alternative Isoforms Detected in the In Vitro EMT Model are Expressed in Primary Human Breast Cancer Samples:

To determine whether the alternative mRNA isoforms confirmed in human breast cancer cell lines are relevant to human disease, expression of these events was assessed in fine needle aspiration (FNA) biopsies from breast cancer patients. FNA is the most minimally invasive method of collecting diagnostic material from patients with breast mass. This procedure is performed using a small gauge needle that gently disrupts the tissue and allows loose tumor cells to travel up the needle via capillary action. The FNA sample is usually enriched in tumor cells and can be analyzed by quantitative reverse transcriptase PCR (qRT-PCR) [42], however, due to the small volume of the sample, RNA recovery is low ~tens of nanograms of total RNA at the most. In FNA spreads from human benign ductal lesions, tumor cells appeared cohesive and tightly attached to each other. FNA smears from human invasive ductal carcinomas (IDCs) contained discohesive populations of enlarged tumor cells (FIG. 4A), typical for a highly invasive phenotype. Analysis of 15 random FNA smears from IDCs used in this study for the percentage of tumor, inflammatory and stromal cells demonstrated almost a complete absence of adipocytes, macrophages and inflammatory cells indicating that all of the cells present in FNA samples were ductal cancer cells. The phenotypic characteristics of FNA collected cells suggested that they might represent an appropriate human sample for assessment of alternative mRNA transcript expression found in our in vitro screen for EMT-associated splicing.

To check expression of alternative mRNA isoforms, FNA samples were obtained from 30 patients with IDCs of various grades and growth hormone receptor status. IDCs in patients were classified as well, moderately or poorly differentiated according to the modified Bloom Richardson scale. The clinical and demographic data including patients age, tumor size, lymph node status, estrogen, progesterone and Her2/neu receptor status were also collected.

TABLE 3

Characteristics of the invasive ductal carcinoma (IDC) samples used for the FNA qPCR analysis.

| FNA samples | Size (cm) | Greatest Diameter (cm) | Grade | ER | PR | Her2 | LN |
|---|---|---|---|---|---|---|---|
| 1 | 2 < x < 5 | 2.5 | 6M | pos | pos | neg | pos |
| 2 | <2 | 1.7 | 8P | neg | neg | pos | neg |
| 3 | 2 < x < 5 | 3.2 | 6M | pos | pos | neg | pos |
| 4 | <2 | 2.7 | 8P | pos | pos | neg | neg |
| 5 | <2 | 1.1 | 5W | pos | pos | neg | neg |
| 6 | 2 < x < 5 | 3 | 9P | neg | neg | neg | neg |
| 7 | >5 | 8 | 9P | neg | neg | neg | pos |
| 8 | 2 < x < 5 | 3 | 8P | neg | neg | neg | neg |
| 9 | 2 < x < 5 | 2.1 | 6M | pos | pos | neg | neg |
| 10 | 2 < x < 5 | 3.5 | 8P | pos | pos | neg | neg |
| 11 | <2 | 2.3 | 8P | neg | neg | neg | pos |
| 12 | 2 < x < 5 | 2.5 | 8P | pos | pos | neg | neg |
| 13 | 2 < x < 5 | 2.7 | 9P | pos | pos | neg | pos |
| 14 | 2 < x < 5 | 4 | 8P | pos | pos | pos | neg |
| 15 | 2 < x < 5 | 4 | 8P | pos | pos | neg | pos |
| 16 | 2 < x < 5 | 3 | 7M | pos | neg | neg | pos |
| 17 | <2 | 1.9 | 7M | neg | neg | pos | pos |
| 18 | 2 < x < 5 | 2.2 | 6M | pos | pos | neg | pos |
| 19 | 2 < x < 5 | 2.1 | 7M | pos | pos | neg | neg |
| 20 | <2 | 1.1 | 8P | pos | pos | pos | pos |
| 21 | 2 < x < 5 | 2.5 | 8P | pos | pos | neg | ITC |
| 22 | 2 < x < 5 | 3.8 | 9P | neg | neg | neg | pos |
| 23 | 2 < x < 5 | 2.1 | 7M | pos | pos | pos | neg |
| 24 | 2 < x < 5 | 2.2 | 9P | pos | pos | pos | pos |
| 25 | 2 < x < 5 | 2.7 | 9P | pos | pos | neg | neg |
| 26 | 2 < x < 5 | 2.5 | 8P | neg | neg | neg | pos |
| 27 | <2 | 0.4 | 6M | pos | pos | neg | pos |
| 28 | <2 | 1.1 | 6M | pos | neg | neg | neg |
| 29 | <2 | 1.6 | 8P | neg | neg | neg | neg |
| 30 | <2 | 1.2 | 7M | pos | pos | neg | neg |

Column 1 - samples number; Column 2- tumor size (cm); Column 3 - greatest diameter of the tumor (cm); Column 4 - tumor grade according to the modified Bloom-Richardson scale (1-9). Differentiation status: M—moderate, P—poor, W—well; Columns 5-8 - growth hormone receptor and lymph node status: ER—estrogen receptor, PR—progesterone receptor, Her2—EGF receptor, LN—lymph node Using the cDNA from 40 IDC samples, inclusion ratios were determined for 6 SE events that exhibited the most change in exon inclusion levels based on the analysis of breast cancer cell lines. These included epithelial inclusion events in ENAH, MBNL1, FLNB and SLC37A2, and mesenchymal inclusion events in MLPH and ARHGEF11 (FIG. 4B). The small amount of RNA isolated from FNA samples permitted analysis of only 6 alternative splicing events per sample. Inclusion ratios were represented as a fold change compared to the average inclusion ratio in fibroadenoma (FA) samples for the same event. Splicing events were then clustered based on the pairwise Spearman correlations among fold change values to assess the relationships between events (FIG. 4C). Interestingly, ENAH and SLC37A2 inclusion events were highly correlated as were MLPH and ARHGEF11 inclusion events. Some epithelial and mesenchymal inclusion events were inversely correlated, e.g., increases in MBNL1 inclusion tended to be associated with decreases in inclusion of the ARHGEF11 alternative exon. Little or no correlation was observed between SLC37A2 and MLPH, SLC37A2 and ARHGEF11 inclusion events. Overall, many IDCs expressed the mesenchymal mRNA isoforms, indicating that EMT-associated splicing occurs in human tumors in vivo.

Unsupervised clustering of splicing ratios of 6 alternative exons in 34 FNA samples demonstrated a significant correlation between 2 mesenchymal markers, MLPH and ARHGEF11, and 4 epithelial markers, ENAH, SLC37A2, FLNB and MBNL1, while epithelial and mesenchymal marker groups were anti-correlated. Approximately Unbiased (AU) p-values obtained from the Pvclust analysis (www.is-.titech.ac.jp/~shimo/prog/pvclust/) were >99% thus supporting reliability of the clustering tree. This result suggests that the IDC samples tended to have either epithelial or mesenchymal splicing patterns but rarely exhibited mixed inclusion patterns, indicating that IDCs could be unambiguously classified into two groups on this basis.

Figures 5A, 5B, 5C:
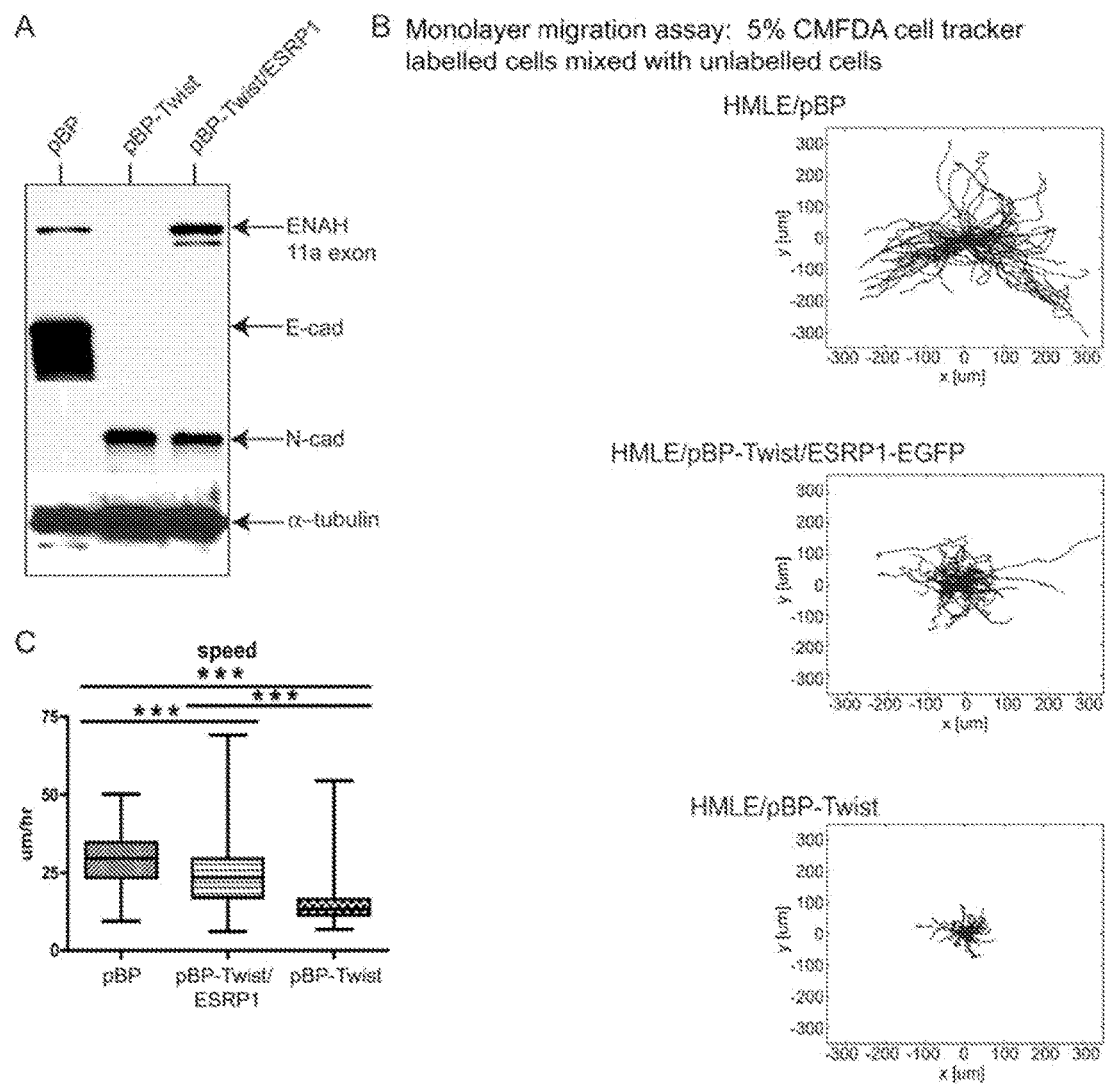
FIG. 5A-5C. Expression of ESRP1 confers epithelial migration properties on mesenchymal cells. (5A) Western blot analysis of cell lysates from HMLE/pBP, HMLE/pBP-Twist and MLE/pBPTwist/ESRP1 cells probed with antibodies as indicated. α-tubulin was used as a loading control. (5B) in a live cell-tracking experiment cells were labeled with a cellular dye CMFDA and plated in the monolayer mixed 1:20 with unlabeled cells. Cells were tracked for 12 hours. Cell tracks were generated using semi-automated cell tracking and represent single cell tracks over 12 hours with 10 minutes intervals. Windrose plots of the range of motion of individual cells of each cell type are shown. Windrose plots were generated by placing starting points of all cell tracks obtained in the cell tracking experiment into the same spot. (5C) The box plot depicts speed distribution of individual cells inferred from live-cell imaging of cells in (5A) and analyzed by the Imaris software. Edges of the boxes indicate 25th and 75th percentile and the whiskers 5th and 95th percentile. The line in the box indicates the median of the distribution. n=138 cells for HMLE/pBP; n=125 cells for HMLE/pBP-Twist; n=113 cells for HMLE/pBPTwist/ESRP1-EGFP. ***=p<0.001.

The ESRP1 splicing factor confers epithelial-like properties to mesenchymal cells. By far the most strongly down-regulated RBPs in EMT were the related factors ESRP1 and ESRP2 (FIG. 2B), which were identified in a screen for regulators of FGFR2 alternative splicing [27]. They have been proposed to promote epithelial phenotype by facilitating epithelial-specific splicing of a number of genes some of which have well documented and essential roles in EMT [27,43]. Silencing of ESRP1/2 in epithelial cells caused re-expression of N-cadherin without affecting E-cadherin levels and lead to a slight, but significant, increase in the rate of monolayer wound healing [31]. It was hypothesized that expression of ESRP1 in mesenchymal cells would convert part of the splicing program to an epithelial state and allow us to examine the role of alternative splicing in the reverse process, a Mesenchymal-to-Epithelial Transition (MET). ESRP1-EGFP was introduced into HMLE/pBPTwist cells, immortalized human mammary epithelial cells that ectopically express Twist [19], and analyzed expression of canonical EMT markers. As expected, control MLE/pBP epithelial cells expressed high levels of E-cadherin while HMLE/pBP-Twist mesenchymal cells expressed high levels of N-cadherin (FIG. 5A; [19]). Expression of ESRP1 in HMLE/pBP-Twist cells was sufficient to switch ENAH splicing to an epithelial pattern, as evident by the inclusion of epithelial-specific 11a exon of ENAH (FIG. 5A). However, ESRP1-expressing cells still had high levels of N-cadherin and low levels of E-cadherin. Thus, ESRP1 expression is sufficient to alter splicing of some targets but is not sufficient to alter expression of EMT markers in mesenchymal HMLE/pBP-Twist cells.

Figure 10:
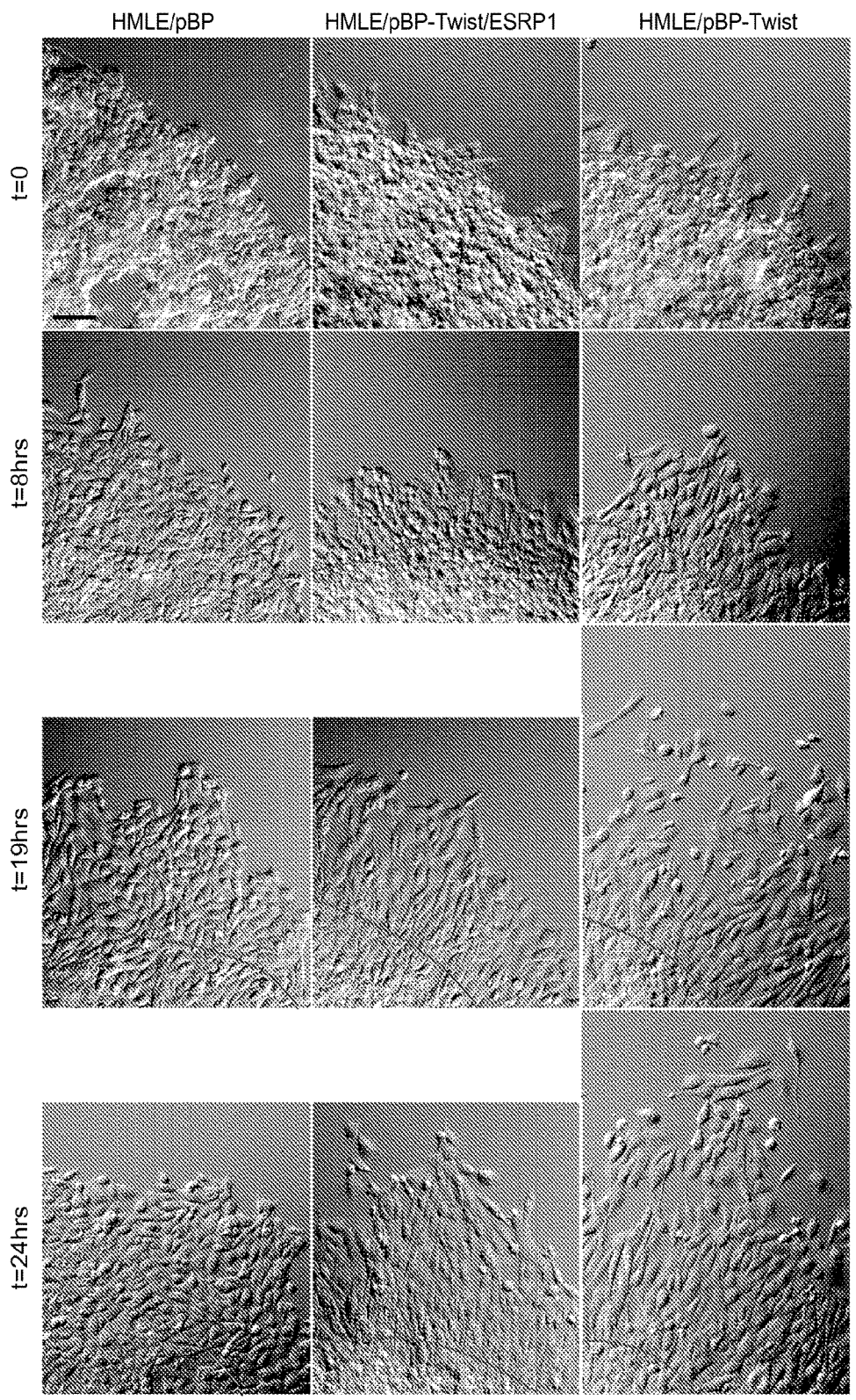
FIG. 10: Comparison of the migration behavior of HMLE/pBP, HMLE/pBP-Twist and HMLE/pBP-Twist/ESPR1 cells. Cells were plated in a matrigel drop on top of a thin matrigel layer and allowed to migrate out of the drop for 24 hrs. Migration was followed using 10×DIC imaging at time intervals after the start of the experiment, as indicated. Dark gray line marks the boundary of the initial matrigel drop. Scale bar, 100 μm.
Figure 11:
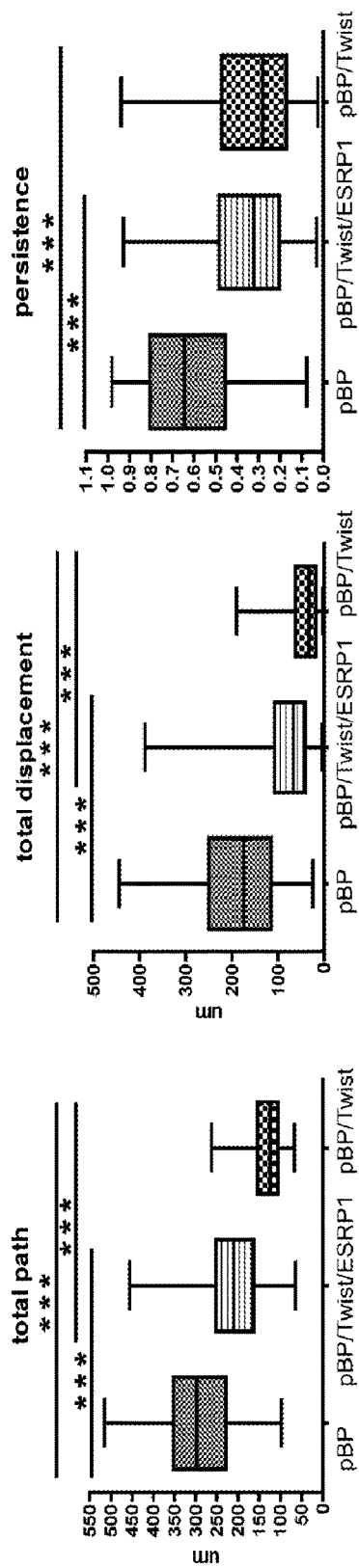
FIG. 11: Monolayer migration assay analysis. Box plots depict migration parameters inferred from live-cell imaging experiment of cells in FIG. 6 and analyzed by the Imaris software. Edges of the boxes indicate 25th and 75th percentile and the whiskers 5th and 95th percentile. The line in the box indicates the median of the distribution. n=138 cells for HMLE/pBP; n=125 cells for HMLE/pBP-Twist; n=113 cells for HMLE/pBP-Twist/ESRP1-EGFP. ***=p<0.001.
Figure 12:
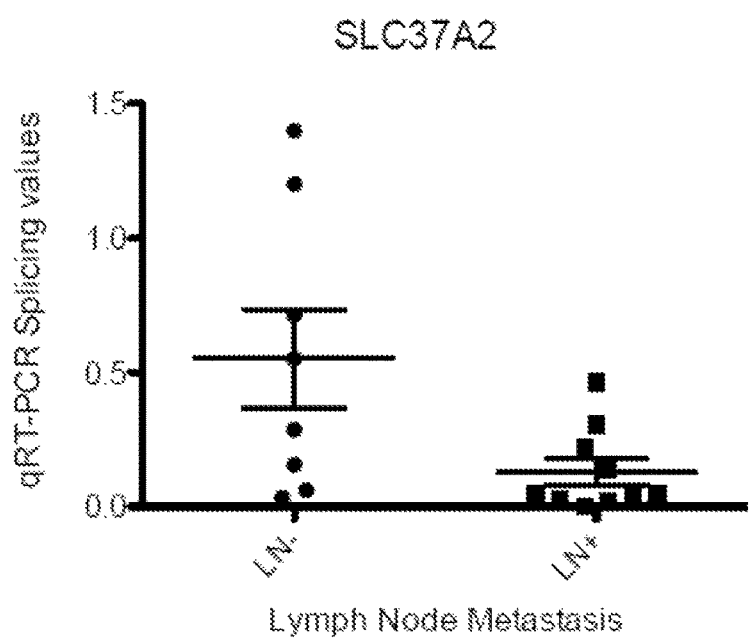
FIG. 12: Figure showing the distribution of qRT-PCR splicing values of epithelial-high SLC37A2 skipped exon event in FNA samples from patients positive (LN+) or negative (LN−) for lymph node metastasis. Mann-Whitney p-value <0.05. Dots and small squares show individual SLC37A2 splicing values in FNA samples. Median and standard error of mean are also shown. The qRT-PCR splicing values were calculated as a ratio of qRT-PCR value (2^Ct) of primer pair targeting the cassette exon of the skipped exon event to the value of primer pair targeting an independent constitutive exon of SLC37A2.
Figure 13:
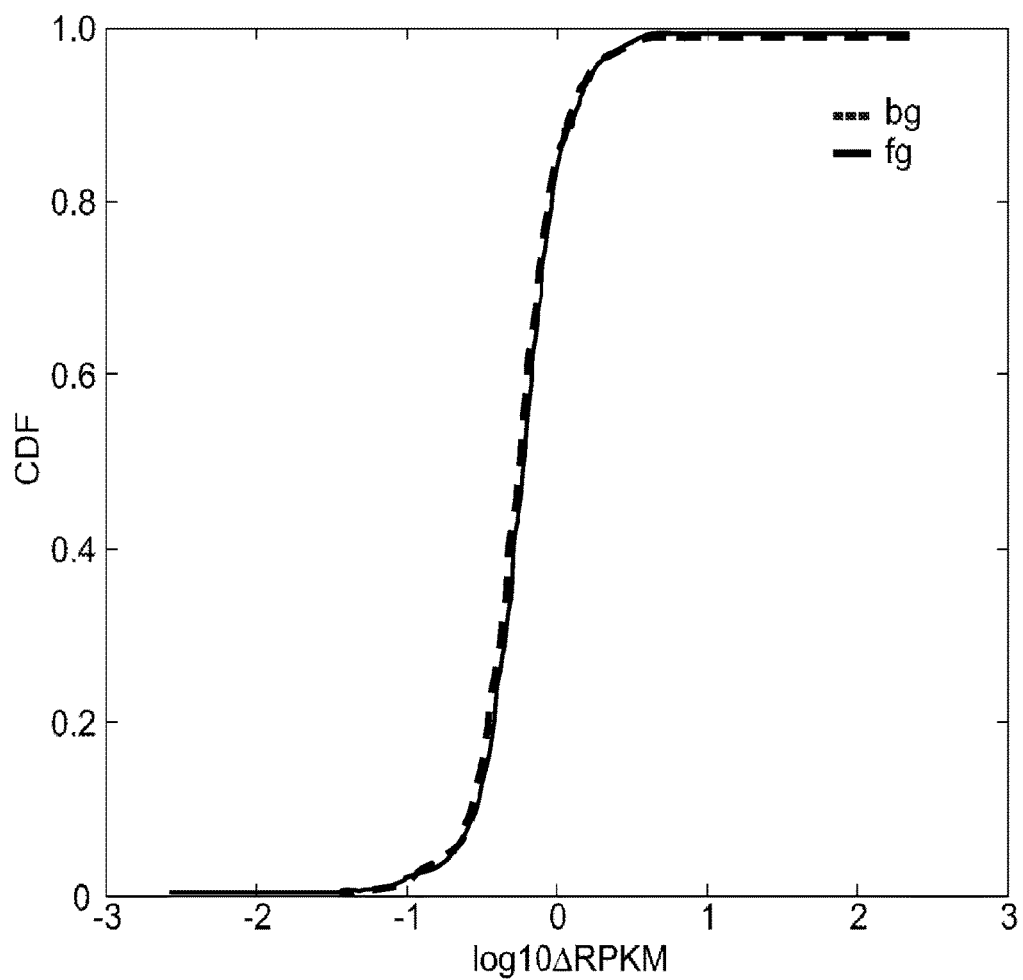
FIG. 13: Regulation of gene expression is independent from regulation of alternative splicing during Twist-induced EMT. Cumulative Density Function (CDF) plot of the distribution of gene expression changes among genes that are alternative spliced (fg (genes with SE events FDR<0.05, |dPsi|>0.1), red line), and not alternatively spliced during EMT (bg (genes in powerset but not in fg), blue dotted line). Kolmogorov-Smirnov (KS) test p-value=0.69.
Figures 14A, 14B, 14C:
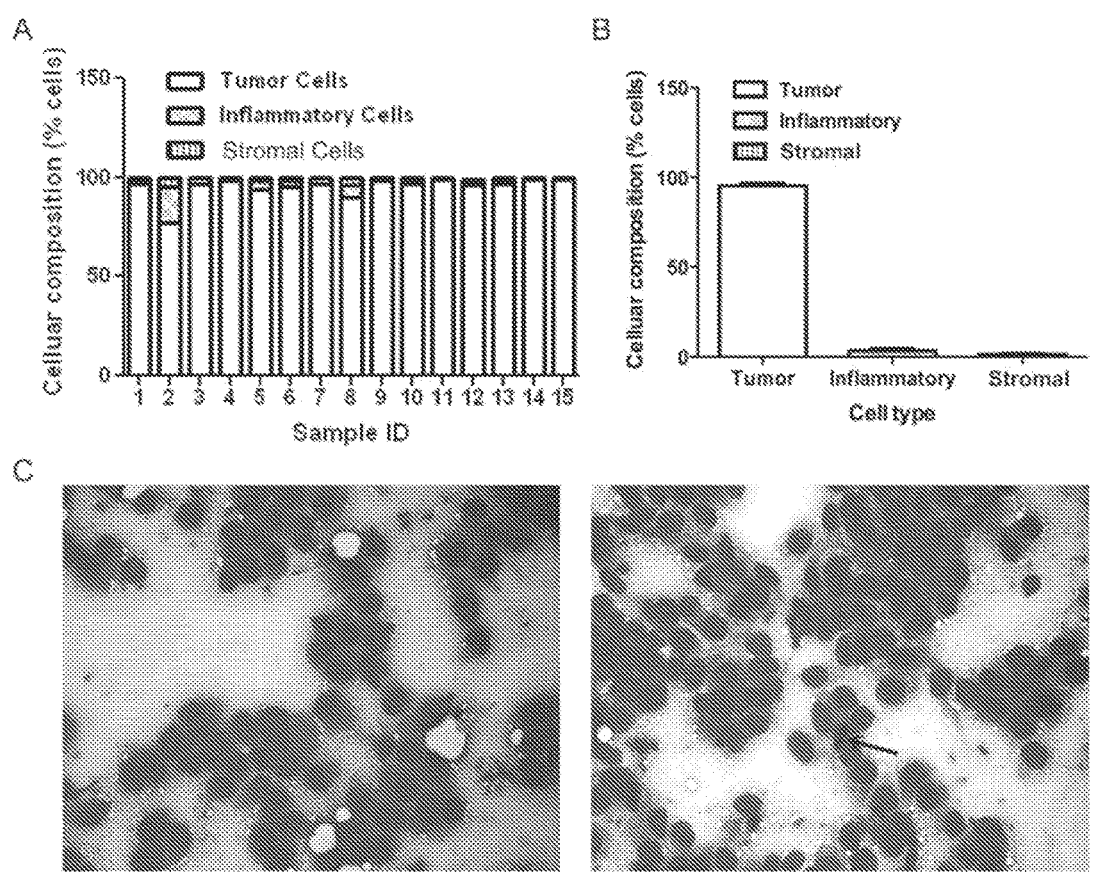
FIG. 14: FNA samples contain negligible amounts of stromal or inflammatory cells. (A) Cellular composition of 15 IDC FNA samples randomly chosen from the 40 FNA samples analyzed in this study. Relative amounts of ductal carcinoma cells (tumor cells), inflammatory cells, and adipocytes and macrophages (stromal cells) are depicted for each sample. (B) Average cellular composition of 15 IDC FNA samples randomly chosen from the 40 FNA samples analyzed in this study. Average relative amounts of ductal carcinoma cells (Tumor cells), inflammatory cells and adipocytes and macrophages (stromal cells) are depicted. Error bars represent SEM. (C) Two representative images of IDC FNA spread. Red error marks fatty droplet. Black error marks inflammatory cell.
Figures 15A, 15B, 15C, 15D:
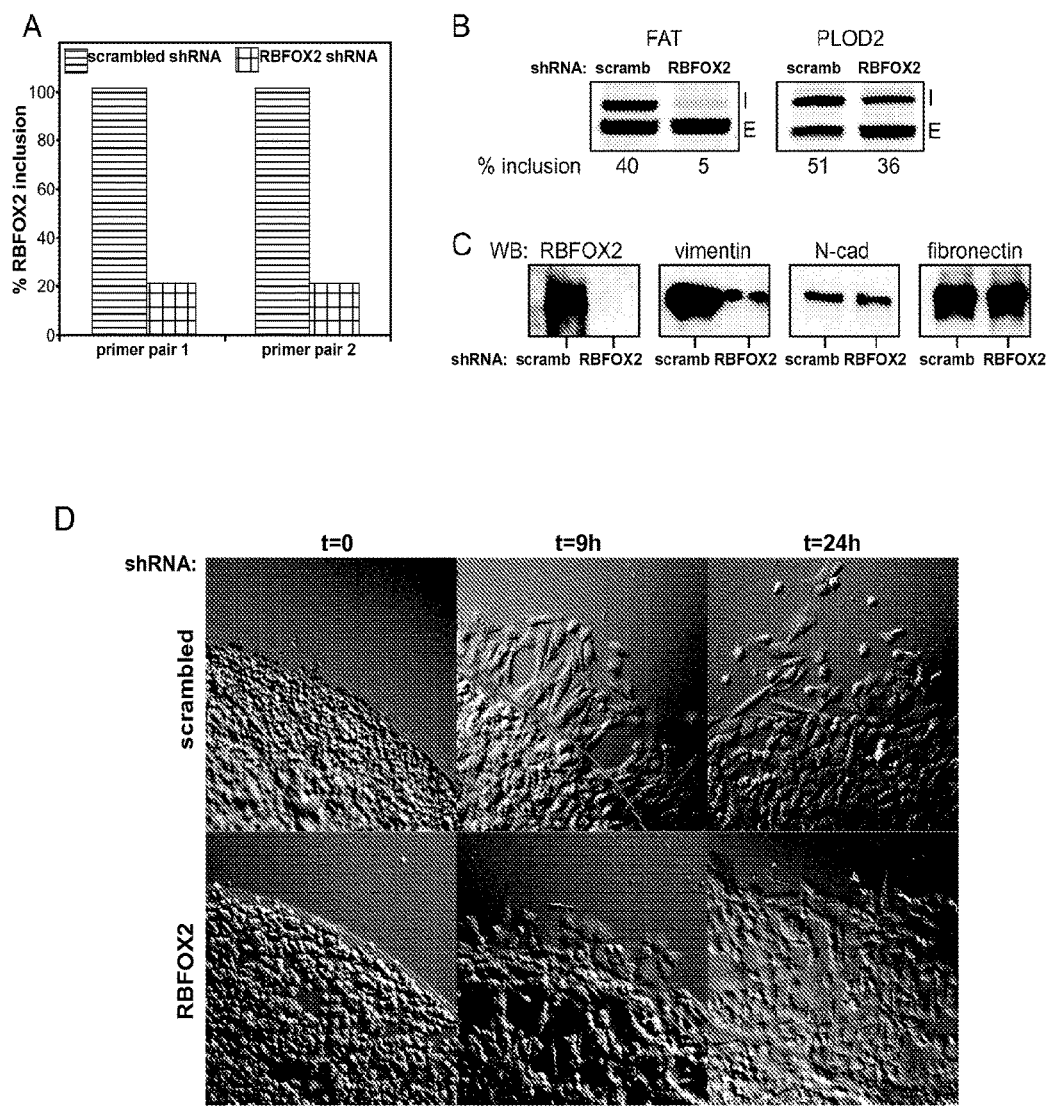
FIG. 15A-15D: Depletion of RBFOX2 confers epithelial-like properties to mesenchymal cells. (15A) qPCR analysis of RBFOX2 levels in HMLE/pBP-Twist cells expressing scrambled shRNA or RBFOX2 shRNA using two different primer pairs. (15B) RT-PCR analysis of alternative exon inclusion in FAT and PLOD2 in HMLE/pBP-Twist cells expressing scrambled shRNA or RBFOX2 shRNA, as indicated. E marks excluded isoform, I marks included isoform. (15C) Western blot analysis of EMT markers and RBFOX2 expression in scrambled or RBFOX2 shRNA treated cells, as indicated. Cell junctions were analyzed using anti-ZO-1, anti-p120catenin, anti-alpha-catenin antibodies and Alexa-350 phalloidin. (15D) Comparison of the migration behavior of HMLE/pBP-Twist cells expressing scrambled or RBFOX2 shRNA.
Figure 16:
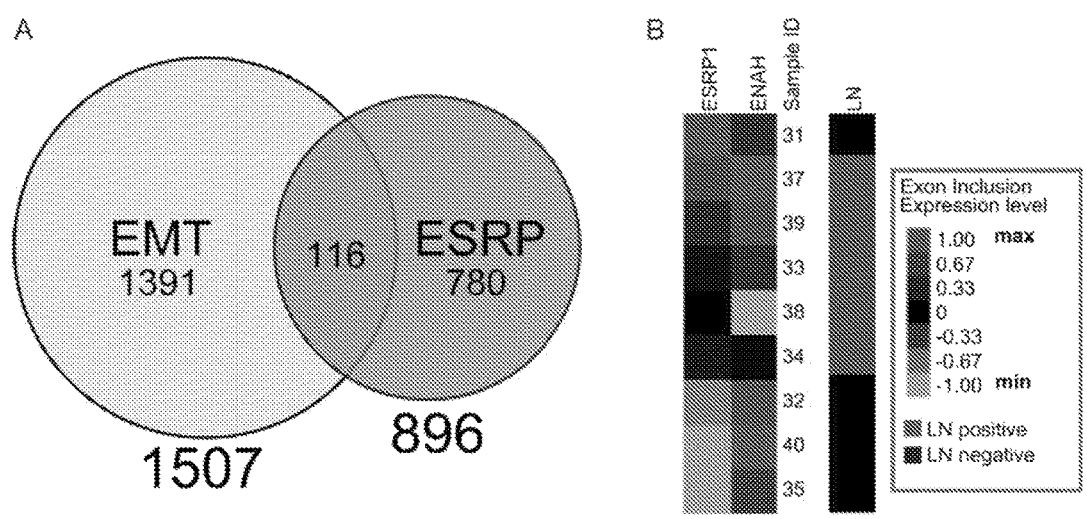
FIG. 16A-16B: ESRP1,2 regulate a subset of EMT-dependent skipped exon events. (16A) Venn diagram showing the overlap of skipped exon events reported in Warzecha et al 2009, 2010 [31,43], and identified from our EMT RNA-seq dataset (FDR<0.05). 1391 events are unique to EMT RNA-seq dataset, 780 events are unique to the union of Warzecha et al. 2009, 2010 [31,43] datasets, 116 are common to both datasets. The numbers beneath the circles denote the number of events reported in the current study and in Warzecha et al. 2009, 2010. (16B) Heatmap of the ESRP expression levels and exon inclusion level of ENAH alternative exon. The expression values and exon inclusion levels are resealed into [−1,1] and depicted as shades of red and green. Sample rows were sorted by ESRP1 expression. Sample ID is shown to the right of the heatplot. Lymphnode metastasis for corresponding samples is shown as red (LN positive) and black (LN negative) circles.

Cell Migration: One important consequence of EMT is altered cell migration. To access qualitatively whether expression of ESRP1 has an effect on migration properties of mesenchymal HMLE/pBP-Twist cells, cell movement was analyzed by time-lapse microscopy of cells migrating out of a matrigel drop. This assay is similar to a standard ex vivo EMT assay used in the studies of developmental EMT to assess cell migration of endocardial cushion explants [44]. Cells were reconstituted in a small volume of matrigel and allowed to migrate out of the cellmatrigel drop for 24 hrs (FIG. 10). Almost no difference in migration was observed in 8 hrs between control epithelial HMLE/pBP cells, mesenchymal HMLE/pBP-Twist cells and the same cells expressing ESRP1. However, by 19 hrs the epithelial HMLE/pBP cells continued to migrate as an epithelial sheet keeping in tight contact with each other, while HMLE/pBP-Twist mesenchymal cells acquired a spindle-shaped morphology, migrated as individual cells and for a longer distance than epithelial cells during the same time (FIG. 11). Interestingly, HMLE/pBP-Twist cells expressing ESRP1 became elongated but continued movement in contact with each other, unlike the scattered mesenchymal morphology of the HMLE/pBP-Twist cells. These differences in migration were further manifested at 24 hrs, indicative that ESRP1 expression conferred an epithelial-like migration behavior to mesenchymal HMLE/pBP-Twist cells (FIG. 10).

To analyze the migration characteristics of mesenchymal cells upon ESRP1 expression quantitatively, an "in monolayer" migration assay [45] was utilized that evaluates the movement of individual cells within a monolayer in contrast to a "sheet monolayer" motility assay which assesses collective cell migration towards an open wound [46]. Epithelial HMLE/pBP cells migrate efficiently only when plated in a monolayer, in contact with other cells, while mesenchymal HMLE/pBP-Twist cell movement is attenuated by cell-cell contact (H D Kim, F B G and D. Lauffenburger unpublished observations). Control HMLE/pBP epithelial cells, HMLE/pBP-Twist mesenchymal cells and HMLE/pBP-Twist cells expressing ESRP1-EGFP were labeled with the whole-cell tracking dye and plated in a confluent monolayer with the equivalent unlabeled cell types such that the labeled cells represent 5% cells within a confluent monolayer to assess migration in the presence of cell-cell contact. As expected, control epithelial cells exhibited significant movement in a 17 hr cell tracking experiment [45,47], while mesenchymal HMLE/pBP-Twist cells moved a little if at all (FIG. 5B). Surprisingly, upon expression of ESRP1, HMLE/pBP-Twist mesenchymal cells demonstrated significant locomotion resembling the movement of epithelial HMLE/pBP cells in a monolayer (FIG. 5B). Windrose plots of cell movement, where all cell tracks are placed into the same starting point, clearly demonstrated the extent of motion for each cell type (FIG. 5B). While many epithelial HMLE/pBP cells traversed paths of up to 300 µM in length, mesenchymal HMLE/pBP-Twist cells moved less than 100 µm. Interestingly, many ESRP1 expressing mesenchymal cells exhibited intermediate range of motion of about 200 µm (FIG. 5B).

Analysis of the cell movement parameters revealed that the speed of ESRP1-expressing HMLE/pBP-Twist mesenchymal cells was significantly increased compared to the speed demonstrated by mesenchymal cells without ectopic ESPR1 expression (FIG. 5C). The total path as well as the displacement covered by HMLE/pBP-Twist/ESRP1 cells were also significantly increased (FIG. 11B). Interestingly, control epithelial cells exhibited more directional movement, since their persistence was significantly higher than for the HMLE/pBP-Twist cells or for the HMLE/pBP-Twist cells expressing ESRP1 (FIG. 11B). Together, these data suggested that splicing changes resulting from ESRP1 expression are sufficient to partially switch the migration properties of mesenchymal cells to epithelial characteristics.

Figure 6:
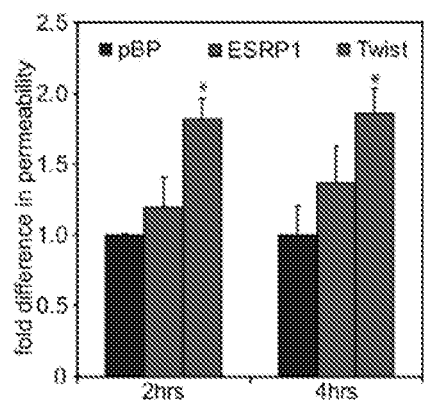
FIG. 6. Expression of ESRP1 changes actin organization and localization of junctional markers in mesenchymal cells towards epithelial morphology. Immunofluorescence of cells was observed using anti-ZO-1 antibody and Alexa350-phalloidin, or using anti-p120catenin antibody and Alexa405-phalloidin. Peripheral actin and stress fibers were determined, as was p120catenin at cell junctions. Figure shows a bar graph depicting movement of Texas Red-dextran across confluent monolayers of HMLE cells, as indicated, at 2 hrs and 4 hrs after addition of dextran compared to control cells expressing pBP (*, P<0.05; n=6). Error bars represent SD. (not shown).

The actin organization and structure of cell-cell contacts have a substantial effect on the migration of cells within monolayers. To characterize phenotypic changes underlying differences in cell migration behavior of epithelial HMLE/pBP cells, mesenchymal HMLE/pBP-Twist cells, and HMLE/pBP-Twist cells expressing ESRP1, immunofluorescence analysis was used to visualize actin organization and cell-cell junctions (FIG. 6A). As expected, three-dimensional structured illumination microscopy analysis revealed the presence of circumferential actin belt in epithelial HMLE/pBP cells, while actin stress fibers prevailed in mesenchymal HMLE/pBP-Twist cells (FIG. 6B). Interestingly, actin organization was altered in HMLE/pBP-Twist cells upon expression of ESRP1. While some stress fibers were present in the central part of the cell, prominent accumulation of peripheral circumferential actin, characteristic of epithelial cell morphology, was also observed. p120catenin, a marker for cell-cell adhesions, decorated areas of cell-cell contact in HMLE/pBP cells, while in HMLE/pBPTwist cells p120catenin localization was barely visible at cell contact points and could be observed only in areas where adjacent cells overlapped without forming obvious junctions (FIG. 6B). Expression of ESRP1 in HMLE/pBP-Twist cells led to increased recruitment of p120catenin to the sites of cell-cell adhesion (FIG. 6B). The tight junction marker ZO-1 as well as alpha-catenin localized to actin filaments that perpendicularly terminated at cell-cell border in immature cell-cell junctions of epithelial HMLE/pBP cells. In contrast, ZO-1 and alpha-catenin localized to the sites of focal cell-cell contact at the ends of stress fibers in mesenchymal MLE/pBP-Twist cells (FIG. 6A). Interestingly, expression of ESRP1 in HMLEpBP-Twist mesenchymal cells lead to ZO-1 and alpha-catenin localization pattern resembling their localization in epithelial cells. Thus, ESRP1 expression in mesenchymal cells partially reverted actin organization and cell-cell junction morphology towards the epithelial phenotype.

A defining feature of epithelia and endothelia is to separate compositionally distinct fluid phase compartments by providing a barrier to ion and solute passage; a prerequisite for the development of most organ systems in vertebrates [48,49]. To assess whether the change in actin organization and cell-cell junction morphology in mesenchymal cells upon expression of ESRP1 would have functional consequences, a cell-based assay was used to compare the ability of fluorescently tagged dextran to cross a confluent monolayer of epithelial HMLE/pBP cells, mesenchymal HMLE/pBP-Twist cells and the same cells expressing ESRP1. As expected, permeability of the mesenchymal HMLE/pBP-Twist cell monolayer was almost two-fold higher than permeability of the epithelial HMLE/pBP cell monolayer (FIG. 6C). Strikingly, expression of ESRP1 in HMLE/pBP-Twist mesenchymal cells significantly improved their barrier function resulting in the permeability that was less then 1.5 fold higher compared to the permeability of the control epithelial cells (FIG. 6C). Thus, epithelial-specific splicing changes conferred to mesenchymal HMLE/pBP-Twist cells by the expression of ESRP1 lead to a substantial improvement in their barrier function possibly caused by epithelial-like reorganization of peripheral actin and cell-cell junctions.

Depletion of RBFOX2 in mesenchymal cells leads to a partial reversion towards epithelial phenotype: As noted above, the analysis and [29] suggest that the RBFOX2 splicing factor likely controls a substantial subset of EMT-dependent alternative splicing (FIG. 2A,C). To assess the effect of RBFOX2 depletion on cell phenotype, we treated HMLE/pBPTwist mesenchymal cells with scrambled shRNA or with shRNA for RBFOX2. qPCR analysis demonstrated ~80% depletion of RBFOX2 mRNA, while RBFOX2 protein levels were virtually undetectable. RT-PCR analysis of the known RBFOX2 targets FAT and PLOD2 [26] confirmed functionality of RBFOX2 depletion. In mesenchymal cells treated with RBFOX2 shRNA, FAT alternative exon inclusion was reduced from 40% to 5%. A less dramatic but significant effect on exon inclusion was also observed for PLOD2 alternative exon. Interestingly, expression of many EMT markers was unaffected by RBFOX2 depletion. No difference in expression was observed for N-cadherin and fibronectin compared to scrambled shRNA-treated control cells. However, vimentin levels were reduced indicating of a partial loss of the mesenchymal expression program in HMLE/pBP-Twist cells upon RBFOX2 knockdown. Immunofluorescence analysis revealed that RBFOX2 depletion in mesenchymal HMLE/pBP-Twist cells shifted their morphology from spindly to cobblestone-like, resembling epithelial cell morphology. Stress fibers, prominent in HMLE/pBP-Twist cells, were not readily observed after RBFOX2 depletion. Junctional markers like ZO-1, p120catenin and alpha-catenin brightly decorated cell-cell contacts suggesting that cell junctions were foamed in these cells in contrast to HMLE/pBPTwist mesenchymal cells, where these markers were barely visible at sites of cell-cell contact. Qualitative assessment of cell migration properties using a matrigel drop assay described above demonstrated that HMLE/pBP-Twist cells expressing a scrambled shRNA exhibited individual cell migration pattern and scattered in 24 hrs of plating characteristic of mesenchymal cells. In contrast, cells expressing RBFOX2 shRNA migrated as a sheet staying in contact with each other. Together, these data suggests that, similar to ectopic ESRP1 expression, knockdown of RBFOX2 conferred a number of epithelial features to mesenchymal cells presumably by shifting their splicing pattern from mesenchymal to partially epithelial.

Discussion

Much of our understanding of the mechanisms that control the profound phenotypic changes associated with EMT has emerged as a consequence of gene expression analysis and characterization of key transcriptional regulators of EMT. Similarly, many clinical studies of cancer progression in patient samples have depended upon gene expression analysis. The recent development of new technologies such as high-throughput sequencing has enabled global analyses of gene regulation at the post-transcriptional level. Application of these technologies has revealed, that alternative splicing is both ubiquitous and highly tissue-specific [23], suggesting that evolution has commonly employed alternative splicing to expand the functional diversity of the human proteome. It is therefore not surprising that developmental processes such as EMT and diseases such as cancer employ alternative splicing as an important means of changing cell phenotype, making it essential to complement gene expression analysis by analyzing changes in splicing to obtain an accurate picture of the landscape of potential proteins expressed under given conditions.

The transcriptome of human mammary epithelial cells induced to undergo EMT by activation of Twist, a transcription factor important for EMT induction during embryonic development and metastasis, was profiled. Using this system, an EMT-associated global change was observed in alternative splicing of a number of genes that are involved in functions crucial for EMT progression, such as cell adhesion, cell motility, and cytoskeletal remodeling. Several of the splicing changes discovered in vitro were also found to occur in a panel of breast cancer cell lines and in vivo in primary human breast cancer samples. It was also demonstrated that expression of an epithelial specific splicing factor, ESRP1, was sufficient to cause a substantial shift in the actin organization, migration properties and barrier function of mesenchymal cells towards the epithelial phenotype. Altogether, the present evidence indicates that EMT contributes to tumorigenesis by changing alternative splicing of genes important for epithelial and mesenchymal cell morphology and motility in addition to the well known changes in the expression levels of messages related to epithelial and mesenchymal specific functions.

Changes in Alternative Splicing Contribute to Pathological EMT

Transcriptional regulation of EMT has been a focus of numerous studies in cancer cell lines and primary tumor samples in the last decade [16]. A number of transcription factors have been identified that repress key regulators of EMT such as E-cadherin and induce transcription of the drivers of mesenchymal phenotype, including N-cadherin and vimentin [17,19,20,50].

Changes in alternative isoform expression during EMT have been observed previously only for a handful of genes including FGFR2, p120catenin and ENAH [25-28]. Recently, the epithelial specific splicing factors ESRP1 and ESRP2 have been shown to regulate splicing of a subset of genes that contribute to the epithelial phenotype [31]. However, the extent to which coordinated changes in splicing might contribute to phenotypic and morphological changes during EMT has not been investigated systematically. The results herein demonstrate that more than a thousand genes undergo changes in alternative isoform expression during EMT, establishing the existence of a program of alternative RNA processing accompanying EMT. Interestingly, many of the alternative splicing events observed likely have a major effect on protein functions important for EMT, including regulation of cell migration, cell adhesion and actin cytoskeleton remodeling (See FIG. 4B; Table 4).

TABLE 4

Functional consequences of alternative splicing in EMT.

| Gene | EMT-relevant gene functional tendency | Change in the reading frame | dΨ | RNA and/or protein region altered by alternative splicing | Inclusion isoform expressed in |
|---|---|---|---|---|---|
| Regulation of actin cytoskeleton and cell adhesion | | | | | |
| WASF1 | regulation of actin cyloskeleton | alternative first exon (AFE) | −0.37 | 5'UTR | epithelial |
| VCL | stabilization of E-cadherin at adherens junctions[3] | intron retention (RI) | −0.22 | 5'UTR | epithelial |

TABLE 4-continued

Functional consequences of alternative splicing in EMT.

| Gene | EMT-relevant gene functional tendency | Change in the reading frame | dΨ | RNA and/or protein region altered by alternative splicing | Inclusion isoform expressed in |
|---|---|---|---|---|---|
| ABI-2 | formation and stability of cell junctions[16] | inframe A3SS | −0.21 | homeo-domain homologous region | epithelial |
| PTPRF | stabilization of adherens junctions[1] | inframa inc/del (SE) | −0.13 | FNIII-like domain 5 (LASE-c)[2] | epithelial |
| ILK | tumor invasion via inhibition of E-cadherin[15] | inframe A3SS | 0.34 | 5'UTR | mesenchymal |
| ABL2 | regulation of actin remodeling[20] | alternative first exon (AFE) | 0.39 | N-terminal | mesenchymal |
| SCRIB | tumor suppressor; supports epithelial cell polarity[24] | inframe inc/del (SE) | 0.39 | partially affects PKC phosphorylation motif | mesenchymal |
| CTNND1 | cell adhesion and signal transduction | inframe inc/del (SE) | 0.68 | N-terminal RhoA binding stabilization domain | mesenchymal |
| Induction of EMT | | | | | |
| FGFR2 | induction of EMT[7] | MXE | −1 | IgIII-like domain | epithelial |
| FGFR1 | induction of EMT[8] | MXE | −0.54 | IgIII-like domain | epithelial |
| STX2 | epithelial cell morphogenesis and activation[6] | premature Stop | −0.46 | C-terminal | epithelial |
| VEGFA | induction of EMP[12] | intron retention (RI) | 0.4 | 3'UTR | mesenchymal |
| TEAD1 | transcriptional activation of mesenchymal targets[4] | inframe inc/del (SE) | 0.61 | internal repeat downstream of TEA domain[5] | mesenchymal |
| Cell mobility and invasion | | | | | |
| FAT1 | enhancement of cell migration and invasion[9] | inframe inc/del (SE) | 0.38 | cytoplasmic domain (FAT1 + 12 [10]) | mesenchymal |
| PPFIBP1 | tumor cell motility and migration[11] | inframe inc/del (SE) | 0.42 | phosphorylation motif for Akt1 | mesenchymal |
| NF2 | tumor suppressor; inhibitor of cell migration[23] | alternative first exon (AFE) | 0.37 | N-terminal intermolecular association domain | mesenchymal |
| TGF-beta pathway | | | | | |
| E2F4 | mediator of TGF-beta response[14] | alternative last exon (ALE) | 0.24 | C-terminal | mesenchymal |
| SMAD2 | mediator of EMT induction via TGF-beta pathway[13] | Alternative first exon (AFE) | 0.4 | N-terminal | mesenchymal |
| BMP1 | promotion of tumor cell migration[22, 22] | inframe inc/del (SE) | −0.13 | PKA C-terminal phosphorylation site | epithelial |
| Wnt signaling pathway | | | | | |
| DKK3 | Wnt signaling antagonist[19] | alternative first exon (AFE) | 0.36 | 5'UTR | mesenchymal |
| CSNK1 A1 | promotes epithelial cell-cell adhesion[18] | A5SS | 0.43 | elongated C-terminus | mesenchymal |
| CSNK1 G3 | Wnt pathway regulation | inframe inc/del (SE) | 0.55 | C-terminal | mesenchymal |

Table 4 legend:
Column 1, EMT-relevant genes that are alternatively spliced;
Column 2, EMT-related function of the corresponding protein;
Column 3, the kind of alternative splicing event;
Column 4 indicates the change in the amount of the inclusion isoform (dΨ = Ψ(mes) − Ψ(epi));
Column 5 describes RNA region or a known protein domain affected;
Column 6 indicates whether inclusion isoform is expressed in epithelial or mesenchymal cells.

For example, inclusion of alternative exon in the C-terminus of ARHGEF11, a Rho guanine nucleotide exchange factor (GEF) 11, also known as PDZ-RhoGEF, is increased in mesenchymal cells. Interestingly, removal of the C27 terminus of ARHGEF11 results in a remarkable increase in its ability to induce RhoA activation in vivo and promotes neoplastic transformation [51]. Furthermore, components of key pathways that control cell motility, invasion and EMT itself are affected by alternative splicing, including components of Wnt and TGF-β signaling pathways. Some RNA regulatory proteins were also affected. For example, increased inclusion of exon 5 of the splicing factor MBNL1 was detected in epithelial cells, a change that occurs in models of myotonic dystrophy and alters the intracellular localization of the protein from cytoplasmic to nuclear [52-54]. Interestingly, several previously uncharacterized mRNA isoforms of genes that control important aspects of EMT have been found in this analysis. For example, a 40% increase in inclusion of a 26aa region in SCRIB (a homolog of Drosophila scribble), involved in regulation of apical-basal polarity and directional migration of epithelial cells [55,56], was observed in mesenchymal cells that might alter a PKC phosphorylation site. This suggests that a full length cDNA may not be an appropriate isoform to use for studying the function of SCRIB in epithelial cells. Altogether, the analysis demonstrates that alternative splicing in EMT leads to changes in protein functions in ways that contribute to the establishment of mesenchymal phenotype.

Could key aspects of EMT and/or MET be driven by splicing changes alone, independently of the transcriptional machinery? The experiments with ESRP1, an epithelial specific splicing factor, suggest that epithelial splicing changes initiated in mesenchymal cells by expression of ESRP1 are not sufficient to convert gene expression into an epithelial pattern. However, mesenchymal cells expressing ectopic ESRP1 altered their actin organization, barrier function and migration characteristics towards an epithelial phenotype indicative of a partial morphological reversion. This finding is provocative because it suggests that although transcriptional control is extremely important to drive EMT, alternative splicing is required to execute the complex changes needed for cells to undergo the dramatic phenotypic change from epithelial to mesenchymal states. Since ESRP1 regulates only a fraction of all EMT-associated alternative splicing events (FIG. 2A, 2C), it is likely that other splicing factors also play important roles in executing the EMT splicing program. Our RBP motif enrichment analysis suggests involvement of the Fox and MBNL families of splicing factors and several hnRNP proteins, including hnRNPs F/H, L and PTB. For Fox-2 and PTB, this potential was supported by significant overlap between exons associated with CLIP-Seq tags and exons that undergo EMT-associated splicing changes. Potentially, alteration of a combination of ESRP1 and other specific splicing factors could be sufficient to drive many aspects of EMT. Thus, if epithelial cells bypass the traditional EMT-inducing transcriptional networks to acquire mesenchymal-like phenotypes by global changes in splicing programs that enable an EMT-like transformation, invasion and metastasis occurring without changes in canonical EMT expression markers may arise from splicing-driven phenotypic changes.

EMT in Primary Breast Cancers:

Evidence for EMT in clinical carcinomas has been difficult to obtain, leading to a controversy regarding the role of EMT as a prerequisite for metastasis. The presence of regions of well-differentiated epithelial morphology within some invasive primary tumors and metastatic lesions, along with expression of epithelial markers in metastatic carcinomas appears to conflict with a role for EMT in metastatic progression [10]. A number of factors that may account for this discrepancy have been suggested, including: 1) incomplete EMT may be sufficient for cells to metastasize; 2) EMT might only occur in a small number of cells within the tumor mass that would quickly disappear by intravasating into blood or lymphatic vessels; and, 3) after colonization, tumor cells revert to an epithelial morphology at metastatic sites through a reciprocal process of mesenchymal to epithelial transformation (MET) [16]. Thus, clinical samples of primary tumor and metastatic nodules may not show evidence of EMT because the relevant cells display a mesenchymal phenotype only when they are in transit from the primary tumor to the site of mestastasis. Moreover, if indeed only a few cells in the primary tumor undergo EMT prior to migration, RNA from these cells would be diluted by RNA from the luminal parts of the tumor in qRT-PCR analyses. FNA samples seem to be an attractive alternative to assess EMT. In the case of benign tumors, where cells are tightly attached to each other, FNA collects groups of cells that on the microscopic spread would appear cohesive. In the case of IDC, where many cells are loosely attached to the tumor mass, FNA collects groups of cells that on the microscopic spread would appear discohesive, permitting analysis of motile loosely attached cells, some of which might presumably have undergone EMT. In the analysis of EMT-associated splicing changes in IDCs from breast cancer patients collected by FNA, two groups of IDCs were identified. In one group inclusion of a set of epithelial splicing events was confirmed, while in a second group inclusion of mesenchymal splicing events was confirmed, suggesting a post-EMT phenotype. These data indicate that in some of the IDCs, tumor cells underwent EMT, consistent with the idea that EMT can contribute to cancer progression. Since these FNA samples were obtained from recently diagnosed cancer patients, no follow up information is available regarding a possible relapse or metastatic status of the tumor.

If incomplete mesenchymal conversion requirement for metastasis is correct [10], IDCs where an epithelial splicing pattern was identified may represent cases of incomplete EMT that may or may not metastasize. IDCs where mesenchymal splicing events were identified are more likely to metastasize than tumors exhibiting the epithelial splicing pattern. The set of 6 splicing events unambiguously distinguishes two groups of IDCs: the epithelial splicing group and the mesenchymal splicing group. Therefore, at least in this study of 30 IDCs, EMT-associated splicing patterns are mutually exclusive in human breast cancers.

EMT-Associated Alternative Splicing Events as Prognostic Markers for Breast Cancer Metastasis:

Splicing aberrations have been associated with several diseases including cancer. Changes in the alternative splicing patterns result in production of new mRNA species or in changes in the levels of different spliced isoforms. In cancer, altered splicing can lead to production of protein isoforms with oncogenic properties [57]. A large-scale analysis of alternative splicing in ductal breast tumors of 600 cancer-associated genes identified 41 breast cancer-specific markers that discriminate between normal breast tissue and ductal breast tumors. Some of the splicing events correlated with the ER status of the tumors, while some correlated with the grade of the tumor [58]. A number of shared splicing events have been recently demonstrated in a panel of breast and ovarian cancers using a high throughput RT-PCR approach [59]. Exon array analysis was recently used to identify subtype-specific alternative splicing events in a panel of breast cancer cell lines [29]. Therefore, it appears likely that alternative splicing analysis will dramatically increase the pool of biomarkers for cancer diagnostics.

Since EMT is considered an early event in the metastatic process, splicing changes associated with EMT are of particular interest as useful prognostic and diagnostic markers for breast cancer metastasis. Analysis of the EMT-driven splicing events in the NCI-60 panel of breast cancer cell lines [41] demonstrated that many of the EMT-associated alternative isoforms are expressed in breast cancer cell lines. Furthermore, luminal and basal B cell lines could be distinguished based solely on their splicing patterns. In this regard, EMT-associated alternative splicing events may serve as useful markers for classification of breast cancer cell lines and human cancers. Moreover, splicing events were identified that are novel markers of EMT in vivo. Alternative splicing of ENAH, MLPH, ARHGEF11, MBNL1, FLNB and SLC37A2 transcripts have been confirmed in a number of IDCs, indicating that EMT-associated splicing signature is prognostic.

Table 5: Skipped and Mutually Exclusive alternative splicing events with FDR<0.05 and |ΔΨ|≥0.03.
Column 1 marks the type of event: SE—skipped exon, MXE—mutually exclusive exon. Column 2—Gene symbol. Column 3—Ensembl Gene ID. Column 4—the chromosome number where the gene is located. Column 5—DNA strand on which the gene is encoded. Column 6—exon coordinates of the flanking and alternative exons: for SE events—<upstream flanking exon>, <alternative exon>, <downstream flanking exon>/<upstream flanking exon>, <downstream flanking exon>; for MXE events—<upstream flanking exon>, <alternative exon 1>, <downstream flanking exon>/<upstream flanking exon>, <alternative exon 2>, <downstream flanking exon>. Column 7—the Ψ of the alternative event in the epithelial (pre-EMT) sample. Column 8—the Ψ of the alternative event in the mesenchymal (post-EMT) sample. Column 9—ΔΨ=Ψ(mes)−Ψ(epi). Column 10—FDR.

TABLE 5

| Event Type | GeneName | ensembl Gene ID | chr | strand | inc exon Bound | E.Psi | M.Psi | M-E.deltaPsi | FDR |
|---|---|---|---|---|---|---|---|---|---|
| SE | ACTN1 | ENSG00000072110 | chr14 | − | 68414928-68414993 | 1 | 0.678445 | −0.321555 | 0.00011435 |
| SE | ADARB1 | ENSG00000197381 | chr21 | + | 45379058-45379175 | 0.770538 | 0.345013 | −0.425525 | 0.04215437 |
| SE | ADD3 | ENSG00000148700 | chr10 | + | 111882053-111882148 | 0.382256 | 0.0245902 | −0.357666 | 7.87E-06 |
| SE | ANXA11 | ENSG00000122359 | chr10 | − | 81925843-81925891 | 0.539419 | 0.957077 | 0.417658 | 7.75E-09 |
| SE | APLP2 | ENSG00000084234 | chr11 | + | 129498717-129498884 | 0.646412 | 0.119556 | −0.526856 | 2.35E-119 |
| SE | ARHGAP17 | ENSG00000140750 | chr16 | − | 24858186-24858419 | 0.240401 | 0.556617 | 0.316216 | 5.43E-06 |
| SE | ARHGEF11 | ENSG00000132694 | chr1 | − | 155174834-155174929 | 0.0555074 | 0.679045 | 0.623538 | 3.49E-07 |
| SE | ASXL1 | ENSG00000171456 | chr20 | + | 30481365-30481517 | 0.672622 | 0.133519 | −0.539103 | 6.01E-11 |
| SE | ATP5C1 | ENSG00000165629 | chr10 | + | 7888943-7888979 | 0.885437 | 0.372854 | −0.512583 | 9.67E-05 |
| SE | ATXN2 | ENSG00000204842 | chr12 | − | 110375864-110376032 | 0.671256 | 1 | 0.328744 | 0.0317538 |
| SE | BAIAP2 | ENSG00000175866 | chr17 | + | 76699309-76699354 | 0.547764 | 0.0953846 | −0.452379 | 0.00063712 |
| SE | BBC3 | ENSG00000105327 | chr19 | − | 52423255-52423543 | 0.169312 | 1 | 0.830688 | 0.00611385 |
| SE | BCL2L12 | ENSG00000126453 | chr19 | + | 54865285-54865557 | 0.940983 | 0.59905 | −0.341933 | 1.63E-09 |
| SE | BCS1L | ENSG00000074582 | chr2 | + | 219233004-219233212 | 1 | 0.684492 | −0.315508 | 0.00179004 |
| SE | BCS1L | ENSG00000074582 | chr2 | + | 219233004-219233449 | 1 | 0.646465 | −0.353535 | 0.00038586 |
| SE | BCS1L | ENSG00000074582 | chr2 | + | 219233274-219233449 | 1 | 0.607595 | −0.392405 | 0.02508556 |
| SE | C10orf18 | ENSG00000108021 | chr10 | + | 5791499-5791632 | 0.590558 | 1 | 0.409442 | 0.0141094 |
| SE | C12orf29 | ENSG00000133641 | chr12 | + | 86958056-86958173 | 0.577114 | 1 | 0.422886 | 0.01206544 |
| SE | C17orf80 | ENSG00000141219 | chr17 | + | 68749978-68750085 | 0.555556 | 0 | −0.555556 | 0.04181589 |
| SE | C1orf9 | ENSG00000094975 | chr1 | + | 170789023-170789133 | 1 | 0.392857 | −0.607143 | 0.04845588 |
| SE | C6orf203 | ENSG00000130349 | chr6 | + | 107457922-107458004 | 0.64 | 0 | −0.64 | 0.02691861 |
| SE | C7orf44 | ENSG00000106603 | chr7 | − | 43637136-43637906 | 1 | 0.599584 | −0.400416 | 0.01444963 |
| SE | CD44 | ENSG00000026508 | chr11 | + | 35176244-35176369 | 0.834087 | 0.0129128 | −0.821174 | 9.50E-164 |
| SE | CD44 | ENSG00000026508 | chr11 | + | 35179205-35179318 | 0.78255 | 0.277228 | −0.505322 | 1.78E-109 |
| SE | CD44 | ENSG00000026508 | chr11 | + | 35189369-35189572 | 0.888482 | 0.0526138 | −0.835868 | 2.12E-160 |
| SE | CDC25B | ENSG00000101224 | chr20 | + | 3725274-3725358 | 1 | 0.346001 | −0.653999 | 0.00037634 |
| SE | CDK10 | ENSG00000185324 | chr16 | + | 88281498-88281724 | 0.434988 | 0 | −0.434988 | 0.00587646 |
| SE | CDK5RAP1 | ENSG00000101391 | chr20 | − | 31438790-31439000 | 1 | 0.691099 | −0.308901 | 0.00434407 |
| SE | CLSTN1 | ENSG00000171603 | chr1 | − | 9739126-9739155 | 0.0943605 | 0.588724 | 0.494364 | 0.00738743 |
| SE | CLSTN1 | ENSG00000171603 | chr1 | − | 9720139-9720199 | 0.434087 | 0.92365 | 0.489563 | 0.02238801 |
| SE | CREB5 | ENSG00000146592 | chr7 | + | 28824903-28824931 | 0.092219 | 0.603774 | 0.511555 | 0.03382628 |
| SE | CREM | ENSG00000095794 | chr10 | + | 35477302-35477425 | 0.678337 | 1 | 0.321663 | 0.00036399 |
| SE | CSNK1G3 | ENSG00000151292 | chr5 | + | 122968932-122968955 | 0.230423 | 0.782277 | 0.551854 | 0.00047256 |
| SE | CSNK1G3 | ENSG00000151292 | chr5 | + | 122878001-122878141 | 0 | 1 | 1 | 0.00274791 |
| SE | CTSD | ENSG00000117984 | chr11 | − | 1726821-1726932 | 1 | 0.487486 | −0.512514 | 0.01586222 |
| SE | CUGBP1 | ENSG00000149187 | chr11 | − | 47478989-47479060 | 1 | 0.223077 | −0.776923 | 0.03950546 |
| SE | DAG1 | ENSG00000173402 | chr3 | + | 49499691-49499852 | 0.421053 | 0 | −0.421053 | 0.0365623 |
| SE | DEPDC1 | ENSG00000024526 | chr1 | − | 68720317-68721168 | 0.498806 | 0.161514 | −0.337292 | 0.00071408 |
| SE | DGUOK | ENSG00000114966 | chr2 | + | 74037760-74037875 | 0.628684 | 0.932104 | 0.30342 | 2.17E-06 |
| SE | DHRS4 | ENSG00000157326 | chr14 | + | 23504811-23505032 | 0.570136 | 1 | 0.429864 | 0.02205406 |
| SE | DMWD | ENSG00000185800 | chr19 | − | 50979739-50979813 | 0.378109 | 0.761905 | 0.383796 | 3.99E-08 |
| SE | DNM2 | ENSG00000079805 | chr19 | + | 10780245-10780256 | 0.947874 | 0.442907 | −0.504967 | 1.12E-06 |
| SE | BBS1 | ENSG00000174483 | chr11 | + | 66047219-66047412 | 0.422164 | 0 | −0.422164 | 0.04246639 |
| SE | DTNB | ENSG00000138101 | chr2 | − | 25495888-25495908 | 0 | 0.670157 | 0.670157 | 0.0038951 |
| SE | ENAH | ENSG00000154380 | chr1 | − | 223759316-223759378 | 0.401746 | 0.0191506 | −0.382595 | 3.80E-11 |
| SE | EPB41L1 | ENSG00000088367 | chr20 | + | 34163762-34163816 | 0 | 0.827586 | 0.827586 | 0.02699343 |
| SE | EPB41L1 | ENSG00000088367 | chr20 | + | 34225100-34225290 | 1 | 0.252964 | −0.747036 | 0.00167773 |
| SE | EPN1 | ENSG00000063245 | chr19 | + | 60880224-60880396 | 0.390013 | 0.0896233 | −0.30039 | 7.20E-14 |
| SE | EPSTI1 | ENSG00000133106 | chr13 | − | 42442748-42442806 | 0.600939 | 1 | 0.399061 | 0.01819576 |
| SE | ETV1 | ENSG00000006468 | chr7 | − | 13995418-13995614 | 1 | 0.15756 | −0.84244 | 0.03616638 |
| SE | EVI5 | ENSG00000067208 | chr1 | − | 93012051-93012172 | 0 | 0.423841 | 0.423841 | 0.02817075 |
| SE | FAM49B | ENSG00000153310 | chr8 | − | 130985927-130986013 | 0.538922 | 0.851064 | 0.312142 | 0.04282995 |
| SE | FAM62B | ENSG00000117868 | chr7 | − | 158238233-158238295 | 0.537385 | 0.0361011 | −0.501284 | 3.09E-15 |
| SE | FAT | ENSG00000083857 | chr4 | − | 187748516-187748551 | 0.0344828 | 0.419355 | 0.384872 | 0.00076952 |
| SE | FBXL3 | ENSG00000005812 | chr13 | − | 76493649-76493997 | 0.639175 | 0.947502 | 0.308327 | 3.76E-07 |
| SE | FBXO38 | ENSG00000145868 | chr5 | + | 147786969-147787703 | 1 | 0.686039 | −0.313961 | 0.03618785 |
| SE | FER1L3 | ENSG00000138119 | chr10 | − | 95142664-95142702 | 0.565217 | 0.913978 | 0.348761 | 0.01527048 |
| SE | FGFR2 | ENSG00000066468 | chr10 | − | 123266823-123266967 | 0 | 1 | 1 | 4.90E-07 |
| SE | FIP1L1 | ENSG00000145216 | chr4 | + | 53939997-53940041 | 0.191617 | 0.512535 | 0.320918 | 0.00672654 |
| SE | ATP5SL | ENSG00000105341 | chr19 | − | 46631017-46631179 | 0.659913 | 0.268263 | −0.39165 | 1.02E-09 |
| SE | FLNB | ENSG00000136068 | chr3 | + | 58102625-58102696 | 0.99135 | 0.638109 | −0.353241 | 1.12E-06 |
| SE | GTPBP8 | ENSG00000163607 | chr3 | + | 114196672-114196802 | 0.66087 | 1 | 0.33913 | 4.87E-06 |
| SE | H2AFY | ENSG00000113648 | chr5 | − | 134716535-134716634 | 0.920716 | 0.547876 | −0.37284 | 1.40E-09 |
| SE | HACL1 | ENSG00000131373 | chr3 | − | 15603036-15603113 | 0.48731 | 0.826162 | 0.338852 | 0.02447797 |
| SE | HEG1 | ENSG00000173706 | chr3 | − | 126216247-126216546 | 0.76681 | 0.433634 | −0.333176 | 0.00694631 |

TABLE 5-continued

| Event Type | GeneName | ensembl Gene ID | chr | strand | inc exon Bound | E.Psi | M.Psi | M-E.deltaPsi | FDR |
|---|---|---|---|---|---|---|---|---|---|
| SE | HM13 | ENSG00000101294 | chr20 | + | 29619542-29619744 | 0.386707 | 0.0593142 | −0.327393 | 0.00131394 |
| SE | HMGCS1 | ENSG00000112972 | chr5 | − | 43343625-43343683 | 0.372642 | 0.754572 | 0.38193 | 0.00980539 |
| SE | HMGN1 | ENSG00000205581 | chr21 | − | 39639626-39641088 | 0.324527 | 1 | 0.675473 | 2.01E−21 |
| SE | HNRNPUL1 | ENSG00000105323 | chr19 | + | 46461445-46462543 | 0.943165 | 0.612139 | −0.331026 | 2.29E−31 |
| SE | KIAA1468 | ENSG00000134444 | chr18 | + | 58097687-58098069 | 0.148089 | 0.743405 | 0.595316 | 0.01817773 |
| SE | KIAA1468 | ENSG00000134444 | chr18 | + | 58098573-58098655 | 1 | 0 | −1 | 6.18E−05 |
| SE | KIF13A | ENSG00000137177 | chr6 | − | 17879324-17879428 | 0.688995 | 0.197531 | −0.491464 | 0.00899906 |
| SE | ZNF283 | ENSG00000176232 | chr19 | + | 49033045-49033171 | 0.511182 | 1 | 0.488818 | 0.03973441 |
| SE | LMBR1L | ENSG00000139636 | chr12 | − | 47784796-47784935 | 1 | 0.647975 | −0.352025 | 0.04617294 |
| SE | LOC149773 | | chr20 | − | 56529852-56530013 | 1 | 0.204255 | −0.795745 | 0.01794205 |
| SE | MARK3 | ENSG00000075413 | chr14 | + | 103036246-103036290 | 0.12615 | 1 | 0.87385 | 0.00025963 |
| SE | MATR3 | ENSG00000015479 | chr5 | + | 138643523-138643646 | 0.793388 | 0.299065 | −0.494323 | 0.0003781 |
| SE | MAX | ENSG00000125952 | chr14 | − | 64638017-64638043 | 0.202532 | 0.546867 | 0.344335 | 0.00014918 |
| SE | MBNL1 | ENSG00000152601 | chr3 | − | 153647183-153647236 | 0.742111 | 0.281818 | −0.460293 | 6.39E−05 |
| SE | MCOLN3 | ENSG00000055732 | chr1 | − | 85274981-85275139 | 0.421875 | 0 | −0.421875 | 0.00638918 |
| SE | MICAL3 | ENSG00000099972 | chr22 | − | 16689220-16689282 | 0.112676 | 1 | 0.887324 | 1.81E−06 |
| SE | MICAL3 | ENSG00000099972 | chr22 | − | 16675273-16675323 | 0.0615779 | 0.789041 | 0.727463 | 0.00763904 |
| SE | MLPH | ENSG00000115648 | chr2 | + | 238107946-238108029 | 0.0804672 | 0.662729 | 0.582262 | 9.55E−06 |
| SE | MTERFD2 | ENSG00000122085 | chr2 | − | 241684481-241684526 | 0.835267 | 0.387931 | −0.447336 | 0.01322099 |
| SE | MTMR2 | ENSG00000087053 | chr11 | − | 95287054-95287124 | 0.637931 | 1 | 0.362069 | 0.04355369 |
| SE | NFYA | ENSG00000001167 | chr6 | + | 41156528-41156614 | 0.0994561 | 1 | 0.900544 | 0.0302108 |
| SE | NIN | ENSG00000100503 | chr14 | − | 50292960-50295098 | 0.699381 | 1 | 0.300619 | 3.82E−05 |
| SE | NISCH | ENSG00000010322 | chr3 | + | 52489935-52490093 | 0.625407 | 0.258065 | −0.367342 | 0.00516997 |
| SE | RPS2 | ENSG00000140988 | chr16 | − | 1953655-1954367 | 0.4875 | 0.151358 | −0.336142 | 7.28E−05 |
| SE | NUMB | ENSG00000133961 | chr14 | − | 72815742-72815885 | 0.696316 | 0.171061 | −0.525255 | 6.26E−09 |
| SE | ODF2L | ENSG00000122417 | chr1 | − | 86623729-86623861 | 0.645161 | 1 | 0.354839 | 0.00314879 |
| SE | OSBPL3 | ENSG00000070882 | chr7 | − | 24869344-24869436 | 0.150121 | 0.841248 | 0.691127 | 6.47E−05 |
| SE | OSBPL8 | ENSG00000091039 | chr12 | − | 75377770-75377806 | 0.461538 | 0.111111 | −0.350427 | 0.01676312 |
| SE | PBRM1 | ENSG00000163939 | chr3 | − | 52563780-52563935 | 0.709677 | 0.10596 | −0.603717 | 3.76E−07 |
| SE | PICALM | ENSG00000073921 | chr11 | − | 85378944-85379090 | 0.510116 | 0.106248 | −0.403868 | 6.26E−12 |
| SE | PLD3 | ENSG00000105223 | chr19 | + | 45563409-45563677 | 0.817814 | 0.495327 | −0.322487 | 0.00119361 |
| SE | PLEKHA1 | ENSG00000107679 | chr10 | + | 124177782-124177822 | 0.0992761 | 0.704846 | 0.60557 | 0.00977889 |
| SE | PLEKHA1 | ENSG00000107679 | chr10 | + | 124177782-124177926 | 0.0283061 | 0.386941 | 0.358635 | 0.04758508 |
| SE | PLEKHA1 | ENSG00000107679 | chr10 | + | 124124847-124125058 | 0.195519 | 1 | 0.804481 | 0.01228056 |
| SE | PLEKHM2 | ENSG00000116786 | chr1 | + | 15920446-15920470 | 0.467641 | 0.776903 | 0.309262 | 0.00432366 |
| SE | PLOD2 | ENSG00000152952 | chr3 | − | 147278339-147278401 | 0.412811 | 0.989331 | 0.57652 | 2.37E−08 |
| SE | PPFIBP1 | ENSG00000110841 | chr12 | + | 27721264-27721296 | 0.148148 | 0.574949 | 0.426801 | 0.0001236 |
| SE | PPIE | ENSG00000084072 | chr1 | + | 39983634-39987026 | 0.549236 | 1 | 0.450764 | 0.03094101 |
| SE | PVT1 | | chr8 | + | 128877322-128877456 | 0.671329 | 1 | 0.328671 | 0.00277478 |
| SE | PVT1 | ENSG00000221315 | chr8 | + | 128936583-128936747 | 0.60251 | 0.0531561 | −0.549354 | 0.01163834 |
| SE | OFD1 | ENSG00000046651 | chrX | + | 13691785-13691895 | 0.672673 | 1 | 0.327327 | 0.00036918 |
| SE | RAD18 | ENSG00000070950 | chr3 | − | 8975604-8975685 | 1 | 0.470588 | −0.529412 | 0.03227243 |
| SE | RBM3 | ENSG00000102317 | chrX | + | 48319147-48319415 | 0.833522 | 0.303318 | −0.530204 | 2.73E−09 |
| SE | RCOR3 | ENSG00000117625 | chr1 | + | 209552320-209552452 | 0.315407 | 0 | −0.315407 | 0.00535655 |
| SE | RFX1 | ENSG00000132005 | chr19 | − | 13965337-13965707 | 0.868587 | 0.392037 | −0.47655 | 0.01525018 |
| SE | RNMT | ENSG00000101654 | chr18 | + | 13749941-13750207 | 0.60344 | 1 | 0.39656 | 0.00967014 |
| SE | RPS24 | ENSG00000138326 | chr10 | − | 79469268-79469989 | 0.0858246 | 0.50144 | 0.415615 | 3.46E−213 |
| SE | SBF1 | ENSG00000100241 | chr22 | − | 49242329-49242406 | 0.679793 | 0.285431 | −0.394362 | 0.01860405 |
| SE | SCRIB | ENSG00000180900 | chr8 | − | 144961710-144961772 | 0.142328 | 0.535005 | 0.392677 | 8.90E−16 |
| SE | SDCCAG3 | ENSG00000165689 | chr9 | − | 138424363-138424512 | 0.576299 | 0.147059 | −0.42924 | 4.54E−07 |
| SE | SEC31A | ENSG00000138674 | chr4 | − | 84001808-84001885 | 0.413864 | 0.768192 | 0.354328 | 0.0050853 |
| SE | SEC31A | ENSG00000138674 | chr4 | − | 83982317-83982658 | 0.755074 | 0.430535 | −0.324539 | 9.98E−20 |
| SE | SEPT2 | ENSG00000125354 | chr2 | + | 241905587-241905687 | 0.0569504 | 0.489322 | 0.432372 | 6.50E−09 |
| SE | SFRS14 | ENSG00000064607 | chr19 | − | 18965447-18965549 | 0.859275 | 0.548203 | −0.311072 | 0.02929586 |
| SE | SLC12A9 | ENSG00000146828 | chr7 | + | 100292426-100292734 | 1 | 0.55914 | −0.44086 | 0.01556689 |
| SE | SLC25A22 | ENSG00000177542 | chr11 | − | 786043-786367 | 0.356454 | 1 | 0.643546 | 0.03782749 |
| SE | SLC37A2 | ENSG00000134955 | chr11 | + | 124461310-124461366 | 1 | 0 | −1 | 0.02299246 |
| SE | SLC39A11 | ENSG00000133195 | chr17 | − | 68599558-68599850 | 0.37721 | 0.016546 | −0.360664 | 0.03710532 |
| SE | SLK | ENSG00000065613 | chr10 | + | 105760564-105760656 | 0.469475 | 0 | −0.469475 | 3.32E−09 |
| SE | SNORA24 | ENSG00000207130 | chr4 | − | 119419547-119419740 | 0.80976 | 0.21808 | −0.59168 | 1.13E−26 |
| SE | SNHG1 | | chr11 | − | 62378936-62378986 | 0.77394 | 0.232 | −0.54194 | 0.03260575 |
| SE | SPAG9 | ENSG00000008294 | chr17 | − | 46408223-46408261 | 0.123314 | 1 | 0.876686 | 0.00101524 |
| SE | SPIN1 | ENSG00000106723 | chr9 | + | 90223585-90223686 | 0.693976 | 1 | 0.306024 | 0.02093431 |
| SE | SPTAN1 | ENSG00000197694 | chr9 | + | 130395083-130395142 | 0.92916 | 0.598131 | −0.331029 | 2.98E−05 |
| SE | STX16 | ENSG00000124222 | chr20 | + | 56668085-56668096 | 0.11336 | 0.505643 | 0.392283 | 3.93E−05 |
| SE | STX16 | ENSG00000124222 | chr20 | + | 56668085-56668096 | 0.276757 | 1 | 0.723243 | 0.00040989 |
| SE | STX2 | ENSG00000111450 | chr12 | − | 129846493-129846618 | 1 | 0.536585 | −0.463415 | 0.03005871 |
| SE | STYXL1 | ENSG00000127952 | chr7 | − | 75468144-75468209 | 1 | 0.634921 | −0.365079 | 0.02617002 |
| SE | SULF2 | ENSG00000196562 | chr20 | − | 45721550-45721603 | 0.430397 | 1 | 0.569603 | 0.00715846 |
| SE | TBC1D5 | ENSG00000131374 | chr3 | − | 17444946-17445015 | 0.868571 | 0.410256 | −0.458315 | 0.01612981 |
| SE | TEAD1 | ENSG00000187079 | chr11 | + | 12857012-12857023 | 0.292237 | 0.902821 | 0.610584 | 4.49E−05 |
| SE | TMEM107 | ENSG00000179029 | chr17 | − | 8020002-8020046 | 0.887817 | 0.507937 | −0.37988 | 0.00012007 |
| SE | TMEM132A | ENSG00000006118 | chr11 | + | 60449256-60450132 | 0.439108 | 1 | 0.560892 | 0.00587122 |
| SE | FAM176A | ENSG00000115363 | chr2 | − | 75641314-75641553 | 0.856635 | 0.386895 | −0.46974 | 0.00022507 |
| SE | FAM176A | ENSG00000115363 | chr2 | − | 75606746-75606833 | 0.242003 | 1 | 0.757997 | 3.48E−05 |
| SE | FAM176A | ENSG00000115363 | chr2 | − | 75606746-75606833 | 0.515556 | 1 | 0.484444 | 0.00150214 |
| SE | TMEM175 | ENSG00000127419 | chr4 | + | 931904-932403 | 1 | 0.109777 | −0.890223 | 0.02363012 |

TABLE 5-continued

| Event Type | GeneName | ensembl Gene ID | chr | strand | inc exon Bound | E.Psi | M.Psi | M-E.deltaPsi | FDR |
|---|---|---|---|---|---|---|---|---|---|
| SE | TMEM18 | ENSG00000151353 | chr2 | − | 665758-666238 | 1 | 0.602353 | −0.397647 | 0.00200112 |
| SE | TMEM18 | ENSG00000151353 | chr2 | − | 665758-666238 | 0.0426524 | 0.430976 | 0.388324 | 0.00013405 |
| SE | TOMM40L | ENSG00000158882 | chr1 | + | 159464050-159464151 | 1 | 0.628743 | −0.371257 | 0.00694341 |
| SE | TOP3B | ENSG00000100038 | chr22 | − | 20660277-20660559 | 1 | 0.05 | −0.95 | 0.02515524 |
| SE | TOP3B | ENSG00000100038 | chr22 | − | 20660353-20660559 | 1 | 0.287037 | −0.712963 | 0.01710942 |
| SE | TSC2 | ENSG00000103197 | chr16 | + | 2067600-2067728 | 0.832972 | 0.0997662 | −0.733206 | 0.01344996 |
| SE | TSPAN14 | ENSG00000108219 | chr10 | + | 82218283-82218423 | 0.324419 | 0.863934 | 0.539515 | 0.00535478 |
| SE | TULP4 | ENSG00000130338 | chr6 | + | 158842698-158845198 | 1 | 0.593564 | −0.406436 | 3.39E−09 |
| SE | CTNND1 | ENSG00000198561 | chr1 | + | 57315433-57315721 | 0.144906 | 0.834435 | 0.689529 | 0.00147294 |
| SE | CTNND1 | ENSG00000198561 | chr1 | + | 57315433-57315721 | 0.379631 | 0.937157 | 0.557526 | 1.68E−08 |
| SE | UBXN11 | ENSG00000158062 | chr1 | − | 26500004-26500102 | 1 | 0.583658 | −0.416342 | 0.02797018 |
| SE | USO1 | ENSG00000138768 | chr4 | + | 76935513-76935533 | 0.955224 | 0 | −0.955224 | 6.07E−16 |
| SE | VPS29 | ENSG00000111237 | chr12 | − | 109421723-109421734 | 0.615385 | 1 | 0.384615 | 1.72E−07 |
| SE | WARS | ENSG00000140105 | chr14 | − | 99911373-99911440 | 0.214724 | 0.803801 | 0.589077 | 0.00430163 |
| SE | WARS | ENSG00000140105 | chr14 | − | 99911373-99911496 | 0.234783 | 0.828627 | 0.593844 | 8.08E−05 |
| SE | WDR73 | ENSG00000177082 | chr15 | − | 82990208-82990320 | 0.548134 | 0.0243519 | −0.523782 | 0.0305429 |
| SE | WSB1 | ENSG00000109046 | chr17 | + | 22658897-22659072 | 0.897059 | 0.34375 | −0.553309 | 0.00588716 |
| SE | ZC3H11A | ENSG00000058673 | chr1 | + | 202032044-202032247 | 0.642447 | 0.313341 | −0.329106 | 0.03918161 |
| SE | ZFAND5 | ENSG00000107372 | chr9 | − | 74168206-74168342 | 0.311163 | 0.715715 | 0.404552 | 1.12E−16 |
| SE | ZNF584 | ENSG00000171574 | chr19 | + | 63613185-63613270 | 0.494995 | 0.801431 | 0.306436 | 0.00996676 |
| SE | rumora | | chr7 | + | 27105218-27105510 | 0.850095 | 0.091954 | −0.758141 | 0.00020167 |
| MXE | ABCF3 | ENSG00000161204 | chr3 | + | 185387879-185387925/ 185388146-185388243 | 0.524297 | 0.160899 | −0.363398 | 2.39E−05 |
| MXE | ABHD12 | ENSG00000100997 | chr20 | − | 25248835-25248954/ 25245684-25245714 | 0.527495 | 0.834979 | 0.307484 | 0.00017554 |
| MXE | ALKBH6 | ENSG00000181392 | chr19 | − | 41196086-41196164/ 41195763-41195831 | 0.390081 | 0.903195 | 0.513114 | 7.38E−08 |
| MXE | AP3S1 | ENSG00000177879 | chr5 | + | 115258683-115258754/ 115266481-115266588 | 0.480541 | 0.153921 | −0.32662 | 1.61E−11 |
| MXE | ARHGEF1 | ENSG00000076928 | chr19 | + | 47100941-47101028/ 47101167-47101253 | 0.492075 | 0.157234 | −0.334841 | 7.90E−08 |
| MXE | B3GALNT1 | ENSG00000169255 | chr3 | − | 162301621-162301715/ 162290426-162290544 | 1 | 0.211921 | −0.788079 | 0.04813515 |
| MXE | C16orf63 | ENSG00000133393 | chr16 | − | 15885366-15885563/ 15881162-15881246 | 0.475 | 0.822785 | 0.347785 | 0.00050717 |
| MXE | C16orf63 | ENSG00000133393 | chr16 | − | 15885366-15885563/ 15881162-15881246 | 0.364343 | 0.801756 | 0.437413 | 7.31E−07 |
| MXE | CDC123 | ENSG00000151465 | chr10 | + | 12319149-12319271/ 12320462-12320490 | 0.668687 | 0.336323 | −0.332364 | 1.51E−10 |
| MXE | CIZ1 | ENSG00000148337 | chr9 | − | 129992429-129992544/ 129989963-129990034 | 0.563617 | 0.205571 | −0.358046 | 3.59E−07 |
| MXE | CRTC3 | ENSG00000140577 | chr15 | + | 88958689-88958724/ 88962119-88962204 | 0.565365 | 0 | −0.565365 | 1.87E−07 |
| MXE | DAG1 | ENSG00000173402 | chr3 | + | 49489286-49489342/ 49499691-49499852 | 0.439426 | 1 | 0.560574 | 0.03828733 |
| MXE | DAG1 | ENSG00000173402 | chr3 | + | 49499691-49499852/ 49505264-49505410 | 0.813745 | 0 | −0.813745 | 0.00617427 |
| MXE | DAP3 | ENSG00000132676 | chr1 | + | 153961797-153961826/ 153962407-153962434 | 0.831533 | 0.27027 | −0.561263 | 4.01E−09 |
| MXE | DHX35 | ENSG00000101452 | chr20 | + | 37045756-37045833/ 37050870-37050974 | 0.225564 | 0.764456 | 0.538892 | 0.01499959 |
| MXE | DOCK9 | ENSG00000088387 | chr13 | − | 98296179-98296315/ 98295584-98295627 | 1 | 0.583113 | −0.416887 | 0.00939693 |
| MXE | EBPL | ENSG00000123179 | chr13 | − | 49141914-49141983/ 49135194-49135332 | 0.546269 | 0.206888 | −0.339381 | 7.61E−05 |
| MXE | EPB41L1 | ENSG00000088367 | chr20 | + | 34163762-34163816/ 34225100-34225290 | 0 | 0.661359 | 0.661359 | 0.00042484 |
| MXE | EPB41L1 | ENSG00000088367 | chr20 | + | 34172996-34173152/ 34225100-34225290 | 0 | 0.337149 | 0.337149 | 0.01255246 |
| MXE | EPB41L1 | ENSG00000088367 | chr20 | + | 34163762-34163816/ 34225100-34225290 | 0 | 0.698276 | 0.698276 | 8.51E−05 |
| MXE | EPB41L1 | ENSG00000088367 | chr20 | + | 34172996-34173152/ 34225100-34225290 | 0 | 0.341772 | 0.341772 | 0.00826645 |
| MXE | EXO1 | ENSG00000174371 | chr1 | + | 240082217-240082336/ 240083283-240083406 | 0.483158 | 0.118967 | −0.364191 | 0.01230905 |
| MXE | EXOC7 | ENSG00000182473 | chr17 | − | 71598819-71598911/ 71598005-71598073 | 0.17256 | 0.722749 | 0.550189 | 0.01256309 |
| MXE | FAM49B | ENSG00000153310 | chr8 | − | 131052371-131052423/ 130985927-130986013 | 0.37659 | 0.0734613 | −0.303129 | 0.00683475 |
| MXE | FGFR1 | ENSG00000077782 | chr8 | − | 38399700-38399850/ 38398472-38398616 | 0.543681 | 0.00255738 | −0.541124 | 2.47E−28 |
| MXE | FGFR2 | ENSG00000066468 | chr10 | − | 123268186-123268333/ 123266823-123266967 | 1 | 0 | −1 | 3.55E−07 |
| MXE | FNBP4 | ENSG00000109920 | chr11 | − | 47743398-47743490/ 47732656-47732792 | 0.53461 | 0.208871 | −0.325739 | 0.04686105 |
| MXE | GALNT7 | ENSG00000109586 | chr4 | + | 174455521-174455703/ 174455841-174456023 | 0 | 0.303922 | 0.303922 | 2.84E−07 |

TABLE 5-continued

| Event Type | GeneName | ensembl Gene ID | chr | strand | inc exon Bound | E.Psi | M.Psi | M-E.deltaPsi | FDR |
|---|---|---|---|---|---|---|---|---|---|
| MXE | C16orf48 | ENSG00000124074 | chr16 | − | 66256400-66256572/ 66255341-66255466 | 0.526157 | 0.897709 | 0.371552 | 0.00196034 |
| MXE | GTPBP8 | ENSG00000163607 | chr3 | + | 114194563-114194661/ 114196672-114196802 | 0.674195 | 0.281902 | −0.392293 | 0.0013309 |
| MXE | H2AFV | ENSG00000105968 | chr7 | − | 44849401-44849478/ 44847023-44847136 | 0.390231 | 0.699575 | 0.309344 | 2.41E−12 |
| MXE | HACL1 | ENSG00000131373 | chr3 | − | 15608111-15608191/ 15606051-15606123 | 0.857909 | 0.38537 | −0.472539 | 0.00419124 |
| MXE | HCFC1R1 | ENSG00000103145 | chr16 | − | 3013849-3013970/ 3013476-3013532 | 0.551975 | 0.123867 | −0.428108 | 0.00159291 |
| MXE | HDAC5 | ENSG00000108840 | chr17 | − | 39525275-39525421/ 39525066-39525178 | 0.413329 | 0.731722 | 0.318393 | 0.0364467 |
| MXE | HEXA | ENSG00000213614 | chr15 | − | 70427081-70427153/ 70425922-70426105 | 0.364302 | 0.755776 | 0.391474 | 5.88E−05 |
| MXE | HLA-B | ENSG00000204523 | chr6 | − | 31345693-31345841/ 31345249-31345281 | 0.484917 | 0.150118 | −0.334799 | 7.84E−96 |
| MXE | HSPC111 | ENSG00000048162 | chr5 | − | 175747842-175747950/ 175746447-175746506 | 0.640714 | 0.339979 | −0.300735 | 9.21E−05 |
| MXE | PLAGL1 | ENSG00000118495 | chr6 | − | 144323299-144323372/ 144310815-144311290 | 0.128999 | 0.44995 | 0.320951 | 0.00205822 |
| MXE | KIAA1468 | ENSG00000134444 | chr18 | + | 58097987-58098069/ 58098573-58098655 | 0.115385 | 0.933333 | 0.817948 | 8.72E−06 |
| MXE | MLPH | ENSG00000115648 | chr2 | + | 238100759-238100898/ 238107946-238108029 | 0.918691 | 0.605521 | −0.31317 | 3.79E−07 |
| MXE | NADK | ENSG00000008130 | chr1 | − | 1675350-1675507/ 1674866-1674948 | 0.490795 | 0.181834 | −0.308961 | 2.99E−09 |
| MXE | ODF2L | ENSG00000122417 | chr1 | − | 86625186-86625357/ 86623729-86623861 | 0.610345 | 0.11546 | −0.494885 | 0.00537948 |
| MXE | PAF1 | ENSG00000006712 | chr19 | − | 44572549-44572641/ 44572120-44572241 | 0.618131 | 0.297887 | −0.320244 | 1.62E−08 |
| MXE | PARL | ENSG00000175193 | chr3 | − | 185067107-185067247/ 185063235-185063283 | 0.576184 | 0.253913 | −0.322271 | 0.00067699 |
| MXE | PBRM1 | ENSG00000163939 | chr3 | − | 52567305-52567469/ 52563780-52563935 | 0.236669 | 0.680672 | 0.444003 | 0.00159179 |
| MXE | MED15 | ENSG00000099917 | chr22 | + | 19235723-19235774/ 19239223-19239435 | 0.445651 | 0.762392 | 0.316741 | 2.47E−07 |
| MXE | PPP2R3C | ENSG00000092020 | chr14 | − | 34646261-34646331/ 34638209-34638341 | 0.461666 | 0.781792 | 0.320126 | 0.04006261 |
| MXE | PRKRA | ENSG00000180228 | chr2 | − | 179020478-179020559/ 179017395-179017473 | 0.337423 | 0.714286 | 0.376863 | 0.00088088 |
| MXE | PTMA | ENSG00000187514 | chr2 | + | 232284302-232284373/ 232284910-232284937 | 0.965142 | 0.211864 | −0.753278 | 5.32E−05 |
| MXE | PBXIP1 | ENSG00000163346 | chr1 | − | 153192771-153192857/ 153190895-153191021 | 0.342852 | 0.777481 | 0.434629 | 9.61E−05 |
| MXE | JTB | ENSG00000143543 | chr1 | − | 152216076-152216113/ 152215793-152216022 | 0.641026 | 0.282655 | −0.358371 | 2.45E−11 |
| MXE | RNF138 | ENSG00000134758 | chr18 | + | 27926661-27926847/ 27945715-27945880 | 0.584527 | 0.178717 | −0.40581 | 4.35E−06 |
| MXE | RNF14 | ENSG00000013561 | chr5 | + | 141333332-141333491/ 141339872-141340100 | 0.418803 | 0.765583 | 0.34678 | 2.50E−07 |
| MXE | RNF14 | ENSG00000013561 | chr5 | + | 141334553-141334704/ 141339872-141340100 | 0.330432 | 0.70298 | 0.372548 | 3.39E−06 |
| MXE | RNF185 | ENSG00000138942 | chr22 | + | 29918670-29918688/ 29921455-29921567 | 0.552275 | 0.245034 | −0.307241 | 0.00010917 |
| MXE | RPUSD3 | ENSG00000156990 | chr3 | − | 9860149-9860285/ 9858883-9858927 | 0.564516 | 0.240354 | −0.324162 | 0.00014967 |
| MXE | SEPT2 | ENSG00000125354 | chr2 | + | 241905587-241905687/ 241908291-241908375 | 0.272727 | 0.894737 | 0.62201 | 0.03822668 |
| MXE | SH3GLB2 | ENSG00000148341 | chr9 | − | 130814336-130814398/ 130812770-130812793 | 0.399402 | 0.827704 | 0.428302 | 0.00276125 |
| MXE | SORBS3 | ENSG00000120896 | chr8 | + | 22479284-22479330/ 22479803-22479942 | 0.350554 | 0.0435181 | −0.307036 | 0.04726082 |
| MXE | FAS | ENSG00000026103 | chr10 | + | 90761736-90761818/ 90763080-90763104 | 0.427195 | 0.783401 | 0.356206 | 0.00724902 |
| MXE | SYT7 | ENSG00000011347 | chr11 | − | 61071225-61071356/ 61070079-61070303 | 0.45614 | 0.898768 | 0.442628 | 0.00027762 |
| MXE | MED24 | ENSG00000008838 | chr17 | − | 35463077-35463159/ 35445895-35445933 | 0.386813 | 0.806034 | 0.419221 | 0.00350977 |
| MXE | TOP3B | ENSG00000100038 | chr22 | − | 20666811-20666846/ 20660277-20660559 | 0 | 0.87946 | 0.87946 | 0.04755559 |
| MXE | TRIM5 | ENSG00000132256 | chr11 | − | 5645495-5645517/ 5643787-5643887 | 0.718631 | 0.270154 | −0.448477 | 0.02309609 |
| MXE | TRMT1 | ENSG00000104907 | chr19 | − | 13081972-13082120/ 13081729-13081815 | 0.644165 | 0.29192 | −0.352245 | 0.01135109 |
| MXE | TRMT1 | ENSG00000104907 | chr19 | − | 13084519-13084631/ 13081972-13082120 | 0.554098 | 0.915776 | 0.361678 | 3.56E−05 |

TABLE 5-continued

| Event Type | GeneName | ensembl Gene ID | chr | strand | inc exon Bound | E.Psi | M.Psi | M-E.deltaPsi | FDR |
|---|---|---|---|---|---|---|---|---|---|
| MXE | TSPAN4 | ENSG00000214063 | chr11 | + | 840288-840367/ 852550-852741 | 0.607023 | 0.294118 | −0.312905 | 0.00045947 |
| MXE | WBP2 | ENSG00000132471 | chr17 | − | 71356246-71356338/ 71355472-71355606 | 0.571532 | 0.885972 | 0.31444 | 7.93E−20 |
| MXE | ZDHHC20 | ENSG00000180776 | chr13 | − | 20897791-20897817/ 20893200-20893303 | 0.416107 | 0 | −0.416107 | 0.01405639 |

SE = Skipped Exon. MXE = Mutually Exclusive exons.
In Table 5, alternative exon coordinates (Included exon boundaries) for SE (skipped exons) are shown. For MXE (mutually exclusive exons), coordinates are shown as follows: (included exon boundaries epithelial sample/included exon boundaries mesenchymal sample). The sequence of a given alternative exon is straightforward to obtain by entering the chromosome number and alternative exon coordinates into, for example, UCSC genome browser: genome.ucsc.edu/cgi-bin/hgGateway. The human genome or hg18 assembly is chosen and the chromosome number (chr 14 for ACTN1) and exon coordinates: chr14: 68414928-68414993 can be copied and submitted and the position of this exon in the genome and additional information including sequence is therein provided.

TABLE 6

Splicing signatures used to unambiguously classify NCI-60 breast cancer cell lines into basal and luminal subtypes. Ascending Psi values.

| NAME | array.dIR | M-E.dPsi | cassette exon bound |
|---|---|---|---|
| coherent events \| dPsi \| > 0.1 | | | |
| CD44 | −2.887408088 | −0.821174 | 35176244-35176369 |
| NUMB | −1.001286765 | −0.525255 | 72815742-72815885 |
| FAM62B | −1.508786765 | −0.501284 | 158238233-158238295 |
| SLK | −2.913419118 | −0.469475 | 105760564-105760656 |
| ENAH | −3.529227941 | −0.382595 | 223759316-223759378 |
| H2AFY | −1.185036765 | −0.37284 | 134716535-134716634 |
| OSBPL8 | −1.575275735 | −0.350427 | 75377770-75377806 |
| C17orf61andPLSCR3 | −1.056378676 | −0.293977 | 7237644-7237879 |
| STARD10andCENTD2 | −1.102279412 | −0.284517 | 72081446-72081478 |
| MAP3K7 | −2.288198529 | −0.18007 | 91310992-91311072 |
| BMP1 | −2.453400735 | −0.136815 | 22112480-22112845 |
| BTG3 | −1.623786765 | −0.116082 | 17898334-17898465 |
| YWHAB | 1.384264706 | 0.100771 | 42949703-42949797 |
| ILF3 | 0.774705882 | 0.119182 | 10656092-10656152 |
| PAM | 1.899632353 | 0.246754 | 102337719-102338039 |
| SCRIB | 1.114007353 | 0.392677 | 144961710-144961772 |
| CLSTN1 | 3.145845588 | 0.489563 | 9720143-9720199 |
| MLPH | 1.197481618 | 0.582262 | 238107946-238108029 |
| TXNDC14andCTNND1 | 0.722647059 | 0.689529 | 57315433-57315721 |
| coherent events \| dPsi \| > 0.2 | | | |
| CD44 | −2.8874081 | −0.821174 | 35176244-35176369 |
| NUMB | −1.0012868 | −0.525255 | 72815742-72815885 |
| FAM62B | −1.5087868 | −0.501284 | 158238233-158238295 |
| SLK | −2.9134191 | −0.469475 | 105760564-105760656 |
| ENAH | −3.5292279 | −0.382595 | 223759316-223759378 |
| H2AFY | −1.1850368 | −0.37284 | 134716535-134716634 |
| OSBPL8 | −1.5752757 | −0.350427 | 75377770-75377806 |
| C17orf61andPLSCR3 | −1.0563787 | −0.293977 | 7237644-7237879 |
| STARD10andCENTD2 | −1.1022794 | −0.284517 | 72081446-72081478 |
| PAM | 1.89963235 | 0.246754 | 102337719-102338039 |
| SCRIB | 1.11400735 | 0.392677 | 144961710-144961772 |
| CLSTN1 | 3.14584559 | 0.489563 | 9720143-9720199 |
| MLPH | 1.19748162 | 0.582262 | 238107946-238108029 |
| TXNDC14andCTNND1 | 0.72264706 | 0.689529 | 57315433-57315721 |
| coherent events \| dPsi \| > 0.3 | | | |
| CD44 | −2.8874081 | −0.821174 | 35176244-35176369 |
| NUMB | −1.0012868 | −0.525255 | 72815742-72815885 |
| FAM62B | −1.5087868 | −0.501284 | 158238233-158238295 |
| SLK | −2.9134191 | −0.469475 | 105760564-105760656 |
| ENAH | −3.5292279 | −0.382595 | 223759316-223759378 |
| H2AFY | −1.1850368 | −0.37284 | 134716535-134716634 |
| OSBPL8 | −1.5752757 | −0.350427 | 75377770-75377806 |
| SCRIB | 1.11400735 | 0.392677 | 144961710-144961772 |
| CLSTN1 | 3.14584559 | 0.489563 | 9720143-9720199 |
| MLPH | 1.19748162 | 0.582262 | 238107946-238108029 |
| TXNDC14andCTNND1 | 0.72264706 | 0.689529 | 57315433-57315721 |

In Table 6, two gene names together indicates that these transcripts may be fused. Methods Cell culture: Immortalized human mammary epithelial cells (HMLEs) expressing either the empty pBabe puro vector (pBP), pBP-Twist or pWZL-Twist-ER were obtained from Robert Weinberg's laboratory at the Whitehead Institute for Biomedical Research (Cambridge, Mass.) and cultured as described previously [61]. 4-hydroxy tamoxifen (4-OHT) treatment was performed as described previously [32]. See Methods.

Antibodies, Western Blotting, and Immunofluorescence: Cells were lysed in the presence of 50 mM Tris, pH 8.0, 150 mM NaCl, 0.1% SDS, 0.5% Na-Deoxycholate and 1.0% NP-40 on ice. Twenty micrograms of total protein from each sample were resolved on an 8%-10% SDS-PAGE Gel with Laemmli Running Buffer and transferred to PVDF membranes. The blots were then probed with various antibodies, such as anti-Mena, and anti-Mena-11a, anti-E-cadherin (BD Transduction, Franklin Lakes, N.J.), anti-Fibronectin (BD Transduction, Franklin Lakes, N.J.), antivimentin V9 (Neo-Markers, Thermo Scientific, Fremont, Calif.), or anti-N-cadherin (BD Transduction, Franklin Lakes, N.J.). For immunofluorescence microscopy, cells were plated on glass coverslips, fixed and stained as previously described [1] AlexaFluor405 phalloidin (Molecular Probes) was used at 1:100. Cells were imaged using a Deltavision-OMX or a Deltavision microscope (Applied Precision, Olympus IX71, 100×/1.4NA Plan Apo objective) and processed using a Softworx software (SGI, Mountain View, Calif.).

Plasmids, virus production and infection of target cells: The pMSCV-ESRP1-GFP construct was generated by replacing the Mena cDNA of pMSCV-Mena-GFP [2] with the hESRP1 cDNA (Open Biosystems, clone LIFESEQ3617421). Retroviral packaging, infection, and fluorescence-activated cell sorting (FACS) were performed as previously described [3]. Short hairpin RNA (shRNA) for the knockdown of RBFOX2 was described previously [4] as pB1sH1Fox-2. Hairpin was subcloned into pLKO.1 vector for lentivirus production and infection as described previously [5].

cDNA library preparation for Illumina sequencing: Total RNA was extracted from untreated HMLE/Twist-ER cells (epithelial sample) and after prolonged 4-OHT treatment (mesenchymal sample) using RNeasy Plus Mini kit (Qiagen, Valencia, Calif.). Poly-T capture beads were used to isolate mRNA from 10 mg of total RNA. mRNA was fragmented and used for a first-strand cDNA synthesis by random hexamer-primed reverse transcription and subsequent second-strand cDNA synthesis. Sequencing adaptors were ligated using the Illumina Genomic DNA sample prep kit. Fragments 200 bp long were isolated by gel electrophoresis, amplified by 16 cycles of PCR, and sequenced on the Illumina Genome Analyser (Illumina, San Diego, Calif.), as described previously [23].

Computational analyses of RNA-Seq, exon array data, motif analysis and clustering: Computational and statistical methods are described in the Methods. Briefly, for analysis of RNA-seq data, reads were mapped to the union of the genome and a database of junctional sequences derived from AceView/Acembly annotation.

Expression analysis was based on reads that were mapped to constitutive exons among annotated RefGene transcripts of each gene. Splicing analysis was based on read density supporting either isoforms of an alternative splicing event from a database of alternative isoform events. For more details see the Methods. Raw sequencing reads were deposited in the NCBI Small Read Archive with the accession number SRA012428.4.

Reverse Transcriptase PCR Analysis: Total RNA for validation of splicing events in HMLE/Twist-ER cells was extracted using RNeasy Plus Mini kit (Qiagen, Valencia, Calif.) and reverse transcribed with Superscript II (Invitrogen, Life Technologies, Carslbad, Calif.). The resulting cDNA was used for 25 cycles of PCR with primers listed in the Methods. Then samples were subjected to 10% TBE gel electrophoresis (Bio-Rad, Hercules, Calif.), stained with SYBR Safe DNA Gel Stain (Invitrogen Life Technologies, Carslbad, Calif.), scanned (Typhoon, GE Healthcare, Piscataway, N.J.) and quantified (ImageQuant 5.2). Total RNA from FNA samples was extracted using RNeasy Plus Micro kit (Qiagen, Valencia, Calif.). The resulting cDNAs were used for qPCR analysis using iQ Syber-Green Supermix (Bio-Rad, Hercules, Calif.) in triplicates. qPCR and data collection were performed on iCycler (Bio-Rad, Hercules, Calif.). Primer sequences used to amplify cDNAs and the detailed description of quantification analysis are listed in the methods below.

Human tissue selection and FNA Biopsy Procedure: Lumpectomy and mastectomy specimens that arrive to grossing rooms at Albert Einstein College of Medicine hospitals, Montefiore and Weiler for pathological examination were used for tissue collection. The specimens were sectioned as usual at 0.5 or 1.0 cm intervals to locate and visualize the lesion of interest. Four to 5 FNA aspiration biopsies (passes) were performed on grossly visible lesions using 25 gauge needles. When an FNA needle is inserted into a malignant tumor it preferentially collects loose tumor cells, as can be noted on FNA obtained smears in FIG. 5. A small number of other cell types may also be present, most commonly inflammatory cells and macrophages. The aspirated material was collected in the cryo-vials, and to assess the adequacy of the sample, a small portion of the aspirated material was taken out of the vial, smeared on a glass slide, air-dried and stained by standard Diff-Quick protocol. The adequacy of the sample was determined by cytopathologic microscopic examination of the smears. Only samples composed of 95% of either benign or malignant epithelial cells were used in the study. Standard cytopathologic criteria such as cell size, nuclear/cytoplasmic ratio, nuclear contours, cell crowding and cohesiveness of the cells were the major criteria for classification into benign or malignant category. Samples containing a mixture of malignant and benign cells, necrotic cell debris, or more than 5% of inflammatory or stromal cells as determined by cytopathologic microscopic examination were discarded. FNA biopsy samples were immediately snap frozen in liquid nitrogen and stored frozen for RNA isolation followed by a qPCR analysis. Specimens were collected without patient identifiers following protocols approved by the Montefiore Medical Center Institutional Review Board.

Cell migration assays: Matrigel overlay assay was performed as previously described [44]. 105 cells were mixed with 3.5 mg/ml matrigel and polymerized in a drop on top of the matrigel covered coverslip. Images of migrating cells at 0, 8 hr, 19 hrs, 24 hrs time points were obtained on a Nikon Eclipse TE200 using a 10×DIC objective. Cell migration assay was performed as previously described [45,63]. Cells were incubated with CMFDA (Invitrogen) for 10 minutes and seeded overnight. Labeled and unlabeled cells were seeded at a 1:20 ratio. In 24 hrs, cells were placed on an environment controlled Nikon TE2000 microscope (Nikon Instruments; Melville, N.Y.) and were imaged every 10-minutes for 12 hrs. Image sequences were analyzed with Bitplane Imaris software (Zurich, Switzerland) using the built-in "Spots" function. 12-hour tracks were generated using the "Brownian Motion" algorithm.

Permeability assay: HMLE/pBP-EGFP, HMLE/pBP-Twist-EGFP and HMLE/pBP-Twist/ESRP1-EGFP cells were seeded at confluence on polycarbonate transwell membrane inserts (3.0 μm pore size; Falcon 353492) and cultured for 3 d. 70 kD of Texas red-dextran (Invitrogen, Life Technologies, Carlsbad, Calif.) was added to the top chamber at 2 mg/ml, and its movement into the bottom chamber was monitored over 4 hrs by spectrophotometer.

qPCR analysis quantification: GAPDH mRNA was used to normalize RNA inputs. 2 pairs of primers were used for each alternative splicing event. One pair of primers was complimentary to a region outside alternative exon, the other pair had one primer internal to alternative exon and the other primer flanking alternative exon. All quantitations were normalized to an endogenous control GAPDH. The relative inclusion value for each target splicing event was expressed as $2^{-(Ct-Cc)}$ (Ct and Cc are the mean threshold cycle differences after normalizing to GAPDH).

Primers used for qPCR analysis of cell line cDNA and FNA samples cDNA (from left to right then top to bottom, SEQ ID NOS: 1-42, respectively):

| Gene name | Alternative exon Forward primer 5'-3' | Alternative exon Reverse primer 5'-3' | Outside region Forward primer 5'-3' | Outside region Reverse primer 5'-3' |
| --- | --- | --- | --- | --- |
| GAPDH | CATGAGAAGTATGACAACAGCCT | AGTCCTTCCACGATACCAAAGT | N/A | N/A |
| ENAH | CAACAAGAAAACCTTGGGAAA | GGACCTGTTGTCAAAAACAATCT | GAACAAAAGAGGACAAAGGTGA | TGCCATTCATTGTATTTGTTCTTT |
| SLC37A2 | GGTCCTAACCCACCAGTGAT | ACTGGGACCCTCCATGCT | GGGCTGAGTTGTGTCTCCAT | GAGAGATGCCCATTTTCCAG |
| MBNL1 | CTCAGTCGGCTGTCAAATCA | AGAGCAGGCCTCTTTGGTAA | TTCATCCACCCCCACATTTA | TTGGCTAGTTGCATTTGCTG |
| FLNB | TGTGATCTATGTGCGCTTCG | CATTTACCGGTGCCTCCTC | ATCGCCTCCACTGTGAAAAC | AGTGCCATCTGGGGTCAG |
| ARHGEF11 | TGGCATGCTGACATAAAAGC | GGTTGTCCCTGCACTACCAG | TGACAGAAGGTGTGGGTGTC | AACCTGCGACATCTGATCCT |
| MLPH | GATGGCCTCCCACCATTC | CAGGTAGGTCAGCAGGCATT | AGGAAGCTGGAGGAGCTGAC | CCCAACTGATTTGTCCCTGT |
| KIF13A | CAGGGTTATGTGCCTGAGGT | CAAGCCCCTAATGCCTGTAA | AGAAGGGACCACCATGTCAG | CTCACGGGTCTTGGAGAAAG |
| PLOD2 | GCAGTGGATAATAGCCTTCCA | GACTCCCCTACTCCGGAAAC | CTAGCATTTCGGCAAAGAGC | TGTACTTAATTAAAGGAAAGACACTCC |
| PLEKHA1 | AAGGCTGTCGAACCCTTGTA | GAGGCTGTGGAATGTGAGGT | GTCAAGCCAGGGAACTTCAA | TTTCCTGAGGGCCATTTTTA |
| CLSTN1 | CACCTTCTTATCCGCGAGTT | AACTGAGCCTGTGACTGTGG | GAGCGGGTAATCCTCAGTCA | AATGGCACCACTACGTCCTC |

Primers used for the semi-quantitative RT-PCR Skipped Exon events analysis: (from left to right then top to bottom, SEQ ID NOS: 43-104, respectively):

| Gene name | Forward primer 5'-3' | Reverse primer 5'-3' |
| --- | --- | --- |
| SLC37A2 | CTAGCCTGCTTGCTCCTTTG | TGGAAGTTTCCATTGTCTTGC |
| CUGBP1 | AGAGTTCCCGCAAGTCCTTT | TCAAAGTTCCCTGTGTTGTGA |
| ENAH | GGTGAAGATTCAGAGCCTGTAACTTC | CACTGGGCTGTGATAAGGGTG |
| MBNL1 | CATTTGCAAGCCAAGATCAA | TGGGGGAAGTACAGCTTGAG |
| FLNB | TCCTAACAGCCCCTTCACTG | TTCCTGACAGCAAACGGAAT |
| KIF13A | GTTCTCCAAGCTGGCATTGT | GGCCTCTTCTAAGCCAGGAG |
| MICAL3 | GGTCAGCTTGGCATTCAGTT | AGCTGAGCTTCTCCGAGGAC |
| MICAL3 | GCTGCCTCCCCTTCTATCTC | ACGAGGAGGAGGAAGAGTCC |
| PACSIN3 | CTTAGCTGCTGCTGGCTTCT | ACCTCACCCAAAGCCTCACT |

-continued

| Gene name | Forward primer 5'- 3' | Reverse primer 5'-3' |
|---|---|---|
| EPB41L1 | AGCTGGTGTGGACAGAGGAG | CGGCCTCACTGTAGTCCTTC |
| ARHGEF11 | TGGCATGCTGACATAAAAGC | AGAGGCAGCAGGAGGTTACA |
| PLEKHA1 | GCCCTGAAGAGATGCACAGT | GAGGCTGTGGAATGTGAGGT |
| CLSTN1 | TCGGAAAAACTGGGTCATGT | AATGGCACCACTACGTCCTC |
| PLOD2 | CAAAAATCTGCCAGAGGTCA | GATATGGCTCTTTGCCGAAA |
| MLPH | AGTACTTGGCCGATGTGGAC | CTCAGGGCCTCCTCCTCTAC |
| SNX14 | GCAACATAGCTCCCTCCATT | AATCACCAACACGCAATTCA |
| PPFIBP1 | CGGCACTCGAAAAGTCAGAT | CCAGCCAGATCTAGGTGCTC |
| FAT | TGTATGTCCGGCAGAGGAAC | GGAAAGCCTGTCTGAAGTGC |
| NEK1 | TAATCTGTTGGCGCTCATTG | AAACGGGAAGCTATGCAGAA |
| NFYA | GGATCTCCAGAGTGGACAGG | TCCACTGACCTGCACCATTA |
| ROBO1 | TTCGCCTCCTCTCTGGTAAG | ACCCTGTGTCACCTGAGGAC |
| DTNB | TGTATGTGGTGACCCTGTGG | AGGAAGGATGAACTGGAGCA |
| STX2 | TCCAAGGATCACAAGCAAAA | ATCAGAGCAAGGCAAGAAGG |
| CSNK1G3 | GTTCAAATGCACCCATCACA | CCCCAGGATCTGTCTGTGTC |
| TEAD1 | CTTGCCAGAAGGAAATCTCG | CAGCCCCAGCTTGTTATGAA |
| VDP | GAAAATGCCACCCAGAAAGA | TGCAATGGGACAATTGCTTA |
| ATP5C1 | GCCAAGCTGTCATCACAAAA | GGACAAAGGCAGCAGTAAGC |
| TSC2 | CGGTCCAATGTCCTCTTGTC | CACTGGTGAGGGACGTCTG |
| ASXL1 | GCCTCGAGTTGTCCTGACTC | TCTGTTGCGCTTCATTTGAC |
| APLP2 | CATGTCAGACAAGGAAATTACTCA | ATCATTGGTTGGCAGAGGAG |
| CENTD3 | TCCTCGTACACAGGCTCCTC | TATGCCTTTGCTGCCTATCC |

Primers used for semi-quantitative RT-PCR Mutually Exclusive Exon analysis (from left to right then top to bottom, SEQ ID NOS: 105-116, respectively):

| Gene name | Forward flanking primer | Reverse internal primer1 | Reverse internal primer 2 |
|---|---|---|---|
| FGFR2 | CAGGTAGTCTGGGGAAGCTG | GCAGAAGTGCTGGCTCTGTT | CACCACGGACAAAGAGATTG |
| FGFR1 | GCCCCTGTGCAATAGATGAT | AATGTGACAGAGGCCCAGAG | ACCACCGACAAAGAGATGGA |
| DOCK9 | TCAGGCAAACCTCAGTAGCA | ACATTGCCTGTTTCCCGTAA | TCAAGTGTGCTTGGAATTTCTG |
| Septin-2 | CAAGGCGAAGATTCTCATTACC | GCTGCCAAATGAGTTTTGGT | CCTTGGACAAGACCAAAGTCA |

Mapping of sequencing reads: Sequencing reads were preprocessed by the Illumina/Solexa Pipeline. MAQ [4] was used for mapping reads to the hg18 human genome and junction database. The Acembly gene annotation [5] was used to define exon boundaries and splicing junctions. A junction database was generated by concatenating exonic sequences at junctions. For 39 nucleotide (nt) reads, 38 nt from both upstream and downstream exons of a junction were concatenated to represent the junctional sequence. The reference transcriptome on which reads were mapped was the union of the junction database and the genome. The sequence of mTwist cDNA was included in the reference to account for the expression of mTwist during induction of EMT. Only uniquely mapped reads with less than 3 nt mismatches were retained. In addition, to ensure the fidelity of mapping to junctions, a junctional read was kept for subsequent analysis only when both exons flanking the junction were covered by at least 4 nt on the reads. Uniquely mappable positions were found by simulating all reads from both strands of the genomic and the junctional sequences and filtering for positions with unique sequences. These uniquely mappable positions were used in subsequent analysis as the effective lengths of exons. To assess a potential contamination from rRNA, we attempted mapping of all reads onto an rRNA reference constructed from human rRNA sequences downloaded from Silva databases (www.arb-silva.de/).

Inference of gene expression levels: Inference of Gene expression levels was guided by pre-defined transcript annotation from RefGene [6]. To eliminate biases in estimating gene expression due to alternative splicing resulting in some regions of the transcripts differentially present between samples, only constitutively expressed regions, i.e., regions expressed in all annotated transcripts, of a gene were considered. Because the protocol used for mRNA-seq in this study did not provide strand information of the original template, ambiguous regions where there were annotated transcriptions from both strands on the genome were ignored. Noise for expression analysis was modeled as a Poisson random variable parameterized by reads mapping to non-exonic regions of the genome. Let $P_g$ be the probability for a read to land on exons of gene g and $l_g$ be the length of the exons of gene g, $l_e$ be the sum of the length of all exonic regions in the genome. $P_g = l_g / l_e$. Let $r_{e0}$ be the number of noisy reads distributed onto exonic regions in the genome, $d_{ne}$ be the density of reads aligning in non-exonic regions of the genome. $r_{e0}$ is estimated from non-exonic read density, i.e., $r_{e0} = d_{ne} \times l_e$. Random variable $X_g$ is the number of reads aligned on gene g under the null model and $X_g \sim$ Poisson ($\lambda = r_{e0} P_g = l_g d_{ne}$). The p-value for expression of a gene with x reads aligned can thus be derived as $P(X_g \geq x, \lambda = r_{e0} P_g)$. Benjamini-Hochberg (B-H) FDR procedure [7] was used to get FDR for expression ($FDR_{exp}$). TMM normalization [8] were used to find a scaling normalization factor for normalizing expression in mesenchymal sample using epithelial sample as the reference. Gene expression values were expressed in Reads Per Kilobase of Exon Model Per Million Mapped Reads (RPKM) which normalizes read counts to length of exons and total reads from the sample mapped to the reference [9]. We added the poisson noise $\lambda = r_{e0} P_g$ to each gene's read counts such that RPKM from genes with no reads aligned can be log-transformed. The RPKM values were normalized using the TMM normalization constant. Let E be pre-EMT sample, M be post-EMT sample. We used two criteria (DE1 and DE2) for differential expression. For DE1, We used the Audic-Claverie statistics [10] requiring B-H FDR for differential expression ($FDR_{de}$)<0.05. For DE2: we applied an arbitrary threshold of 3 fold. Differentially expressed (DE) genes were classified into two classes. Class 1 DE genes were those satisfying DE1 criterion but not DE2 criterion. Class 1 DE genes were labeled as either "Up" or "Down", if RPKM(M)>RPKM(E) and RPKM(E)>RPKM(M), respectively. Class 2 DE genes were those satisfying both DE 1 and DE2 criteria. These genes were labeled as either "Up3×" or "Down3×", for 3 fold up or 3 fold down from epithelial to mesenchymal cells, respectively. Genes were called ubiquitously expressed or not changed if FDRexp in both samples <0.05 and did not pass DE1 criterion. Genes were labeled as "not expressed" if FDRexp>=0.05.

Inference of alternative mRNA processing events and alternative transcription initiation: Inference of alternative mRNA processing events and alternative transcription initiation was guided by transcript annotation information from AceView [5]. A splice graph was constructed from all transcripts annotated for a gene such that exons were represented by nodes and edges were formed by connecting exons when there is a junction between them. The splice graph was traversed to identify splicing events depicted in FIG. 2. To quantify splicing, we used a measure called "Percent spliced-in" or Psi ($\Psi$) [11]. $\Psi$ was calculated by dividing the inclusion read density by the sum of the inclusion and exclusion read densities. Inclusion and exclusion isoforms were defined differently for different AS events and are illustrated in FIG. 2. Calculation of value for each event is similar to Wang et al., 2008 [11], with slight changes to the filters, briefly: inclusion reads (NI) are the reads that are mapped to the inclusion junction(s) or the inclusion-specific (cassette) exon body. Exclusion reads (NE) are the reads that are mapped to the exclusion junction(s) or the exclusion-specific exon body (if applicable). In SE, RI, 5'AltSS, 3'AltSS, NE+ is the sum of exclusion reads plus the reads that are mapped to flanking exons; otherwise NE+ is just exclusion reads. Fisher's exact test was performed on a 2×2 table using NI and NE+ from the two samples. An event is detectable if inclusion pos (IP)>=1 and exclusion pos (EP)>=1. At least one isoform of an event is detected if the event is detectable and that inclusion reads (NI)+exclusion reads (NE) in both samples >=1 and that NI and NE in the pooled sample >=10. Both isoforms of an event are detected if the event is detected and both NI>=1 and NE>=1 in the pooled sample. Correction for multiple testings for the Fisher's exact test was performed by B-H FDR procedures on "both isoform detected" set. The "significant AS events" (sigset) were selected from the set of "both isoform detected" events where FDR<0.05 and |$\Delta\Psi$|>=0.1. For gene ontology (GO) enrichment analysis, we defined a set of background events with enough read coverage to detect significant events as the "powerset". The minimal inclusion-exclusion reads and minimal NI, NE+ reads required to give power to detect was decided by finding the following bounds within the sigset: Let NI be inclusion reads, NE be exclusion reads and NEp be NE+reads.

To account for $\Psi$ calculation as a function of NI and NE, we defined two bounds:

B1=min over events i and samples j [NI(i,j)+NE(i,j)]

B2=min over events i (sum over samples j [NI(i,j)+NE(i,j)])

To account for Fisher exact test as a function of NI and NE+, we define B3 and B4 statistics:

B3=min over events i and samples j [NI(i,j)+NEp(i,j)]

B4=min over events i (sum over samples j [NI(i,j)+NEp(i,j)])

The sets with power to detect alternative splicing (powerset) was selected from the "both isoform detected" subset of known events where for each event i:

min over samples j [NI(i,j)+NE(i,j)]>=B1 sum over samples j [NI(i,j)+NE(i,j)]>=B2 min over samples j [NI(i,j)+NEp(i,j)]>=B3 sum over samples j [NI(i,j)+NEp(i,j)]>=B4

In order to ensure that the sigset and powerset have similar distribution of B4 statistics, B4 was iteratively scaled up and other bounds in proportion, until the median of (sum over samples j [NI(i,j)+NEp(i,j)]) of the powerset is equal or slightly higher than that of the sigset. The background set was defined as the union of the powerset and the sigset.

Motif enrichment analysis and prediction of mRNA processing factors operating in EMT: Significant SE events were divided into two sets. Upregulated sets are those with FDR of alternative splicing FDR(AS)<0.05 and $\Delta\Psi$>0.1. Downregulated sets are those with FDR (AS)<0.05 and $\Delta\Psi$<−0.1. These two sets were subjected to motif enrichment analysis separately. 250 bp regions of introns flanking epithelial- or mesenchymal-specifically spliced exons and the upstream and downstream exons were collected for motif enrichment analysis. Sequences were divided into equally sized (100 sequences/bin) bins according to composition of G and C nucleotides (% GC). A separate background pentamer (5mer)-generating first-order Markov model (1MM) was built from mononucleotide and bi-nucleotide frequencies of the sequences in each bin. Background probability of a 5mer was calculated per bin and averaged to get the overall background probability. The actual frequency of a 5mer was obtained by counting its occurrences in all foreground sequences. p-value of a 5mer was calculated by a binomial complementary cumulative density function (ccdf) of its observed frequency over the background probability distribution generated by the 1MM. To find motifs enriched in EMT-regulated exons relative to the non-regulated exons, another analysis based on hypergeometric enrichment of 5mers was performed. The number of occurrences of 5mers was counted from foreground, i.e., the significant set of events (FDR(AS)<0.05 and $\Delta\Psi$>0.1 or $\Delta\Psi$<−0.1), and the corresponding background (union of the significant set with the powerset). To account for CG %, the foreground was first binned into CG % bins. The background sequences were similarly binned. The background sequences were randomly sampled per bin proportional to the bin sizes in the foreground. A hypergeometric enrichment p-value was calculated using the foreground and background frequencies. Correction for multiple testing for both motif analyses was done following B-H FDR procedure.

Expression of RNA binding proteins and splicing factors was explored by finding annotated RNA binding proteins and splicing factors (according to gene ontology annotation and a list of known splicing factors) from the expression data. To overlap EMT events with published CLIP-seq data, binding clusters or binding sites from published CLIP-seq experiments of various splicing factors were compared against the sigsets and powersets of the different EMT events. PTB data was obtained from bed-formatted interval files from GEO database entry [12]. SFRS1 CLIP-data were bed files obtained from Sanford Lab website [13]. RBFOX2 data was downloaded from UCSC genome browser [14]. CLIP-seq clusters from these studies were overlapped with the differentially regulated events in this current study to get the fraction of events in the sigset or the powerset with or without overlaps with CLIP-seq clusters. ESRP RNAi-seq and over-expression-seq data was kindly provided by R. Carstens (Personal Communication; [15]). EMT and ESRP data were overlapped by matching inclusion exon coordinates. The p-values for enrichment or depletion of overlaps were calculated by fisher exact test.

Detection of expression of RNA binding proteins can also be employed as a diagnostic/prognostic marker. RNA binding proteins, as regulators of the EMT splicing signature, can be quantitated for differential expression. A list of RNA binding proteins that exhibited a statistically significant change and with a fold change of 1.5× either up or down in mesenchymal cells compared to control epithelial cells was generated (see above).

Gene ontology (GO) enrichment analysis: Genes were mapped to GO_BP_FAT (Biological Processes) and KEGG pathway annotations using DAVID tool [16,17]. Statistical significance of term enrichment was derived from hypergeometric enrichment p-value of foreground annotation overlap over background annotation overlap for each term. Only terms with >=20 and <=100 genes annotated in the background were tested. In addition, terms with <10 genes annotated in the foreground set were discarded. For expression GO enrichment analysis, up-regulated genes were selected as genes with FDR(exp)<0.05 in mesenchymal sample, FDR(DE)<0.05 and RPKM(M)/RPKM(E)>=3 (Class 2 DE genes, upregulated subset). Down-regulated genes were selected as genes with FDR(exp)<0.05 in epithelial sample, FDR(DE)<0.05 and RPKM(E)/RPKM(M)>=3 (Class 2 DE genes, downregulated subset). These were used as foreground lists. To account for the fact that power of detecting differential expression increases with coverage, background list was composed of the union of the foreground set and a subset of all detectable genes (genes with strand-unambiguous and uniquely mappable positions in constitutive regions) where total number of reads mapped to the analyzed regions of that gene in two samples is bigger than or equal to the lower bound of that in the foreground set. For alternative splicing GO enrichment analysis, significant events (FDR<0.05, $|\Delta\Psi|$>0.1) from all event types were selected, collapsed into unique gene names. The background set consisted of union of the significant set and power set collapsed into unique gene names. B-H procedure was used to account for the false discovery rate associated with multiple comparisons.

NCI-60 breast cancer cell lines exon array and EMT RNA-seq comparison: Cancer cell line exon array data were obtained from GEO database record GSE16732 [18]. The RMA-processed matrix (in log 2) was used for the analysis. Probe sets were remapped to AceView/acembly exons requiring 10 bp overlap. Probesets targeting the same exon were summarized into a single exon value by taking the median. Exons with exon value <log 2(10) were discarded. SE Events from AceView were used to combine exon values into event values as Inclusion probe ratio (IPR). IPR was defined per sample and event as IPR(event,sample)=CX(event,sample)−[UFX(event,sample)+DFX(event,sample)]/2 where CX(event,sample),UFX(event,sample),DFX(event,sample) are the exon values of the cassette exon, upstream flanking exon and the downstream flanking, respectively. The set of IPR values of the events that were detected in EMT RNA-seq (FDR<0.05, $|\Delta\Psi|$>0.1) as well as in the exon array (307 events) were used to cluster the cancer cell lines. These values were row-centered by median and row-normalized before hierarchical clustering using Pearson correlation and average linkage. As a control, the powerset+foreground set of events (8839) were also overlapped with the array data and their IPR values were clustered the same way. To assess the quality of a clustering classification, we derived a simple metric that assessed how well the clustering of the selected splicing events on the cancer cell lines IPR values separated the cancer cell lines into luminal and basal B subtypes [19] by counting the number of outliers. First, the clustering tree was divided into two subtrees rooted by the two children of the root. Each subtree was then treated as a group where the leaves of the subtree are the members of that group. For each group (subtree), we counted the number of basal B cell lines and luminal cell lines. Cell lines of the minority cell type were treated as outliers. The total number of outliers was the sum of outliers in the two groups. To test the significance of the clustering classification, we performed a randomization-clustering procedure. Random sets of 307 events (same size as the foreground set) were chosen from the background set and subjected to clustering using the same metrics as we did with the foreground set. The randomization-clustering procedure was repeated 10000 times. The p-value was derived as the number of random sets with fewer or the same number of total outliers as/than resulted from clustering of the foreground set divided by the total number of random sets tested (i.e., 10000).

To find a subset of "core" EMT splicing events that separates the luminal and basal B groups, the following procedures were undertaken: cell lines were grouped into Luminal and Basal B groups according to [19] and listed below. Inclusion probe ratio (IPR) per sample group per event was defined using the mean exon values of that group by IPR(event,group)=CXmean(event,group) [UFXmean(event,group)+DFXmean(event,group)]/2 where CXmean(event,group), UFXmean(event,group) and DFXmean(event,group) denote the group mean exon values for cassette exon, upstream flanking exon and downstream flanking exon, respectively. The variance was estimated by IPRvar=CXvar(group)+[UFXvar(group)+DFXvar(group)]/4. Splicing changes ("differential inclusion ratio"–DIR) were inferred by subtracting IPR(Luminal) from IPR (BasalB). A value >0 indicates more inclusion isoform in basal cells. A value <0 indicates more inclusion isoform in luminal cells. The significance of the change detected by array were assessed by a Welch t-test on the IPR and the standard error of the mean (SEM) derived from IPRvar of the basal and luminal samples. Array-detected events with FDR<0.25 were selected for subsequent analysis. These events were compared to the set of significant EMT Skipped Exon (SE) events (FDR<0.05, |ΔΨ|>0.1, 0.2, or 0.3). Of 481 significant RNA-seq SE events, 268 were detected by array above the probe detection threshold, of which, 28 were called significantly changed in the array (array FDR<0.25, EMT RNA-seq FDR<0.05, |ΔΨ|>0.1). A coherent event was defined as an event called significant in both the NCI-60 cancer cell line exon array dataset [18] and EMT RNA-seq data and had the same direction of change in EMT as in comparison of luminal to basal B cell lines. Clustering analysis of breast cancer cell lines from the NCI-60 panel was performed using the 24 coherent events from 28 events called significantly changed in both exon array data and RNA-seq data. The IPR values were used event (row)-centered by median and event-normalized such that sum of squares per event equals 1. Hierarchical clustering using Pearson correlation and average linkage was performed on the transformed data.

Breast cancer cell lines from the NCI-60 panel [18] used for analysis:
Luminal:

| | |
|---|---|
| GSM419256 | BT474 |
| GSM419257 | BT483 |
| GSM419259 | CAMA-1 |
| GSM419264 | MCF7 |
| GSM419265 | MDA-MB-134VI |
| GSM419267 | MDA-MB-175VIII |
| GSM419270 | MDA-MB-361 |
| GSM419271 | MDA-MB-415 |
| GSM419274 | MDA-MB-453 |
| GSM419279 | SKBR-3 |
| GSM419285 | SUM185 |
| GSM419289 | SUM44 |
| GSM419290 | SUM52 |
| GSM419291 | T47D |
| GSM419292 | UACC812 |
| GSM419294 | ZR751 |
| GSM419295 | ZR7530 |

Basal B:

| | |
|---|---|
| GSM419258 | BT549 |
| GSM419263 | Hs578T |
| GSM419266 | MDA-MB-157 |
| GSM419268 | MDA-MB-231 |
| GSM419272 | MDA-MB-435 |
| GSM419273 | MDA-MB-436 |
| GSM419282 | SUM1315 |
| GSM419283 | SUM149 |
| GSM419284 | SUM159 |

Hierarchical clustering of FNA samples: Hierarchical clustering of FNA samples were done on Ratio to Average (RA) values (fold change to average inclusion ratios in fibroadenoma samples) using Biopython (biopython.org) Cluster3 module (Spearman correlation, average linkage) [20]. Cluster tree and heatmap was visualized in Java-TreeView [21].

Method for assessing dependency between gene expression and alternative splicing: To assess dependency of gene expression changes and alternative splicing regulation, we compared the cumulative distribution of log expression changes during EMT in the set of genes differentially spliced during EMT (foreground) and a background set of genes which are not differentially spliced during EMT. Kolmogorov-Smirnov (KS) test was performed on the CDF curves to estimate the p-value of the distribution differences.

REFERENCES

1. Weigelt B, Peterse J L, van't Veer L J (2005) Breast cancer metastasis: markers and models. Nat Rev Cancer 5: 591-602.
2. van't Veer L J, Dai H, van de Vijver M J, He Y D, Hart A A, et al. (2002) Gene expression profiling predicts clinical outcome of breast cancer. Nature 415: 530-536.
3. Slodkowska E A, Ross J S (2009) MammaPrint 70-gene signature: another milestone in personalized medical care for breast cancer patients. Expert Rev Mol Diagn 9: 417-422.
4. Christofori G (2006) New signals from the invasive front. Nature 441: 444-450.
5. Vincent-Salomon A, Thiery J P (2003) Host microenvironment in breast cancer development: epithelial-mesenchymal transition in breast cancer development. Breast Cancer Res 5: 101-106.
6. Yang J, Weinberg R A (2008) Epithelial-mesenchymal transition: at the crossroads of development and tumor metastasis. Dev Cell 14: 818-829.
7. Yilmaz M, Christofori G (2009) EMT, the cytoskeleton, and cancer cell invasion. Cancer Metastasis Rev 28: 15-33.
8. Nelson W J (2008) Regulation of cell-cell adhesion by the cadherin-catenin complex. Biochem Soc Trans 36: 149-155.
9. Condeelis J, Pollard J W (2006) Macrophages: obligate partners for tumor cell migration, invasion, and metastasis. Cell 124: 263-266.
10. Christiansen J J, Rajasekaran A K (2006) Reassessing epithelial to mesenchymal transition as a prerequisite for carcinoma invasion and metastasis. Cancer Res 66: 8319-8326.
11. Abba M C, Drake J A, Hawkins K A, Hu Y, Sun H, et al. (2004) Transcriptomic changes in human breast cancer progression as determined by serial analysis of gene expression. Breast Cancer Res 6: R499-513.
12. Sorlie T, Perou C M, Tibshirani R, Aas T, Geisler S, et al. (2001) Gene expression patterns of breast carcinomas distinguish tumor subclasses with clinical implications. Proc Natl Acad Sci USA 98: 10869-10874.
13. Thompson E W, Newgreen D F, Tarin D (2005) Carcinoma invasion and metastasis: a role for epithelial-mesenchymal transition? Cancer Res 65: 5991-5995; discussion 5995.

14. Rubin M A, Putzi M, Mucci N, Smith D C, Wojno K, et al. (2000) Rapid ("warm") autopsy study for procurement of metastatic prostate cancer. Clin Cancer Res 6: 1038-1045.
15. Blick T, Widodo E, Hugo H, Waltham M, Lenburg M E, et al. (2008) Epithelial mesenchymal transition traits in human breast cancer cell lines. Clin Exp Metastasis 25: 629-642.
16. Hugo H, Ackland M L, Buick T, Lawrence M G, Clements J A, et al. (2007) Epithelial—mesenchymal and mesenchymal—epithelial transitions in carcinoma progression. J Cell Physiol 213: 374-383.
17. Mani S A, Yang J, Brooks M, Schwaninger G, Zhou A, et al. (2007) Mesenchyme Forkhead 1 (FOXC2) plays a key role in metastasis and is associated with aggressive basal-like breast cancers. Proc Natl Acad Sci USA 104: 10069-10074.
18. Thisse B, el Messal M, Perrin-Schmitt F (1987) The twist gene: isolation of a Drosophila zygotic gene necessary for the establishment of dorsoventral pattern. Nucleic Acids Res 15: 3439-3453.
19. Yang J, Mani S A, Donaher J L, Ramaswamy S, Itzykson R A, et al. (2004) Twist, a master regulator of morphogenesis, plays an essential role in tumor metastasis. Cell 117: 927-939.
20. Bolos V, Peinado H, Perez-Moreno M A, Fraga M F, Esteller M, et al. (2003) The transcription factor Slug represses E-cadherin expression and induces epithelial to mesenchymal transitions: a comparison with Snail and E47 repressors. J Cell Sci 116:499-511.
21. Comijn J, Berx G, Vermassen P, Verschueren K, van Grunsven L, et al. (2001) The twohanded E box binding zinc finger protein SIP1 downregulates E-cadherin and induces invasion. Mol Cell 7: 1267-1278.
22. Blencowe B J (2006) Alternative splicing: new insights from global analyses. Cell 126: 37-47.
23. Wang E T, Sandberg R, Luo S, Khrebtukova I, Zhang L, et al. (2008) Alternative isoform regulation in human tissue transcriptomes. Nature 456: 470-476.
24. Srebrow A, Kornblihtt A R (2006) The connection between splicing and cancer. J Cell Sci 119: 2635-2641.
25. Savagner P, Valles A M, Jouanneau J, Yamada K M, Thiery J P (1994) Alternative splicing in fibroblast growth factor receptor 2 is associated with induced epithelial-mesenchymal transition in rat bladder carcinoma cells. Mol Biol Cell 5: 851-862.
26. Pino M S, Balsamo M, Di Modugno F, Mottolese M, Alessio M, et al. (2008) Human Mena+11a isoform serves as a marker of epithelial phenotype and sensitivity to epidermal growth factor receptor inhibition in human pancreatic cancer cell lines. Clin Cancer Res 14: 4943-4950.
27. Warzecha C C, Sato T K, Nabet B, Hogenesch J B, Carstens R P (2009) ESRP1 and ESRP2 are epithelial cell-type-specific regulators of FGFR2 splicing. Mol Cell 33: 591-601.
28. Keirsebilck A, Bonne S, Staes K, van Hengel J, Nollet F, et al. (1998) Molecular cloning of the human p120ctn catenin gene (CTNND1): expression of multiple alternatively spliced isoforms. Genomics 50: 129-146.
29. Lapuk A, Man H, Jakkula L, Pedro H, Bhattacharya S, et al. Exon-level microarray analyses identify alternative splicing programs in breast cancer. Mol Cancer Res 8: 961-974.
30. Yeo G W, Coufal N G, Liang T Y, Peng G E, Fu X D, et al. (2009) An RNA code for the FOX2 splicing regulator revealed by mapping RNA-protein interactions in stem cells. Nat Struct Mol Biol 16: 130-137.
31. Warzecha C C, Jiang P, Amirikian K, Dittmar K A, Lu H, et al. An ESRP-regulated splicing programme is abrogated during the epithelial-mesenchymal transition. Embo J.
32. Mani S A, Guo W, Liao M J, Eaton E N, Ayyanan A, et al. (2008) The epithelial-mesenchymal transition generates cells with properties of stem cells. Cell 133: 704-715.
33. Shang Y, Hu X, DiRenzo J, Lazar M A, Brown M (2000) Cofactor dynamics and sufficiency in estrogen receptor-regulated transcription. Cell 103: 843-852.
34. Thierry-Mieg D, Thierry-Mieg J (2006) AceView: a comprehensive cDNA-supported gene and transcripts annotation. Genome Biol 7 Suppl 1: S12 11-14.
35. Mortazavi A, Williams B A, McCue K, Schaeffer L, Wold B (2008) Mapping and quantifying mammalian transcriptomes by RNA-Seq. Nat. Methods 5: 621-628.
36. Audic S, Claverie J M (1997) The significance of digital gene expression profiles. Genome Res 7: 986-995.
37. Taube J H, Herschkowitz J I, Komurov K, Zhou A Y, Gupta S, et al. Core epithelial-to mesenchymal transition interactome gene-expression signature is associated with claudinlow and metaplastic breast cancer subtypes. Proc Natl Acad Sci USA 107: 15449-15454.
38. LaGamba D, Nawshad A, Hay E D (2005) Microarray analysis of gene expression during epithelial-mesenchymal transformation. Dev Dyn 234: 132-142.
39. Xue Y, Zhou Y, Wu T, Zhu T, Ji X, et al. (2009) Genome-wide analysis of PTB-RNA interactions reveals a strategy used by the general splicing repressor to modulate exon inclusion or skipping. Mol Cell 36: 996-1006.
40. Yoneda T, Williams P J, Hiraga T, Niewolna M, Nishimura R (2001) A bone-seeking clone exhibits different biological properties from the MDA-MB-231 parental human breast cancer cells and a brain-seeking clone in vivo and in vitro. J Bone Miner Res 16: 1486-1495.
41. Riaz M, Elstrodt F, Hollestelle A, Dehghan A, Klijn J G, et al. (2009) Low-risk susceptibility alleles in 40 human breast cancer cell lines. BMC Cancer 9: 236.
42. Maas R A, Bruning P F, Breedijk A J, Top B, Peterse H L (1995) Immunomagnetic purification of human breast carcinoma cells allows tumor-specific detection of multidrug resistance gene 1-mRNA by reverse transcriptase polymerase chain reaction in fine-needle aspirates. Lab Invest 72: 760-764.
43. Warzecha C C, Shen S, Xing Y, Carstens R P (2009) The epithelial splicing factors ESRP1 and ESRP2 positively and negatively regulate diverse types of alternative splicing events. RNA Biol 6: 546-562.
44. Mori M, Nakagami H, Koibuchi N, Miura K, Takami Y, et al. (2009) Zyxin mediates actin fiber reorganization in epithelial-mesenchymal transition and contributes to endocardial morphogenesis. Mol Biol Cell 20: 3115-3124.
45. Joslin E J, Opresko L K, Wells A, Wiley H S, Lauffenburger D A (2007) EGF-receptor mediated mammary epithelial cell migration is driven by sustained ERK signaling from autocrine stimulation. J Cell Sci 120: 3688-3699.
46. Vitorino P, Meyer T (2008) Modular control of endothelial sheet migration. Genes Dev 22:3268-3281.

47. Ewald A J, Brenot A, Duong M, Chan B S, Werb Z (2008) Collective epithelial migration and cell rearrangements drive mammary branching morphogenesis. Dev Cell 14: 570-581.
48. Balda M S, Whitney J A, Flores C, Gonzalez S, Cereijido M, et al. (1996) Functional dissociation of paracellular permeability and transepithelial electrical resistance and disruption of the apical-basolateral intramembrane diffusion barrier by expression of a mutant tight junction membrane protein. J Cell Biol 134: 1031-1049.
49. Troxell M L, Gopalakrishnan S, McCormack J, Poteat B A, Pennington J, et al. (2000) Inhibiting cadherin function by dominant mutant E-cadherin expression increases the extent of tight junction assembly. J Cell Sci 113 (Pt 6): 985-996.
50. Medici D, Hay E D, Olsen B R (2008) Snail and Slug promote epithelial-mesenchymal transition through beta-catenin-T-cell factor-4-dependent expression of transforming growth factor-beta3. Mol Biol Cell 19: 4875-4887.
51. Chikumi H, Barac A, Behbahani B, Gao Y, Teramoto H, et al. (2004) Homo- and heterooligomerization of PDZ-RhoGE F, LARG and p115RhoGEF by their C-terminal region regulates their in vivo Rho GEF activity and transforming potential. Oncogene 23: 233-240.
52. Terenzi F, Ladd A N Conserved developmental alternative splicing of muscleblind-like (MBNL) transcripts regulates MBNL localization and activity. RNA Biol 7.
53. Lin X, Miller J W, Mankodi A, Kanadia R N, Yuan Y, et al. (2006) Failure of MBNL1-dependent post-natal splicing transitions in myotonic dystrophy. Hum Mol Genet 15:2087-2097.
54. Terenzi F, Ladd A N Conserved developmental alternative splicing of muscle blind-like (MBNL) transcripts regulates MBNL localization and activity. RNA Biol 7: 43-55.
55. Phua D C, Humbert P O, Hunziker W (2009) Vimentin regulates scribble activity by protecting it from proteasomal degradation. Mol Biol Cell 20: 2841-2855.
56. Qin Y, Capaldo C, Gumbiner B M, Macara I G (2005) The mammalian Scribble polarity protein regulates epithelial cell adhesion and migration through E-cadherin. J Cell Biol 171: 1061-1071.
57. Pajares M J, Ezponda T, Catena R, Calvo A, Pio R, et al. (2007) Alternative splicing: an emerging topic in molecular and clinical oncology. Lancet Oncol 8: 349-357.
58. Venables J P, Klinck R, Bramard A, Inkel L, Dufresne-Martin G, et al. (2008) Identification o alternative splicing markers for breast cancer. Cancer Res 68: 9525-9531.
59. Venables J P, Klinck R, Koh C, Gervais-Bird J, Bramard A, et al. (2009) Cancer-associated regulation of alternative splicing. Nat Struct Mol Biol 16: 670-676.
60. Borjesson P K, Postema E J, Roos J C, Colnot D R, Marres H A, et al. (2003) Phase I therapy study with (186) Re-labeled humanized monoclonal antibody BIWA 4 (bivatuzumab) in patients with head and neck squamous cell carcinoma. Clin Cancer Res 9: 3961S-3972S.
61. Elenbaas B, Spirio L, Koerner F, Fleming M D, Zimonjic D B, et al. (2001) Human breast cancer cells generated by oncogenic transformation of primary mammary epithelial cells. Genes Dev 15: 50-65.
62. Vuolo M, Suhrland M J, Madan R, Oktay M H (2009) Discrepant cytologic and radiographic findings in adjacent galactocele and fibroadenoma: a case report. Acta Cytol 53: 211-214.
63. Kim H D, Guo T W, Wu A P, Wells A, Gertler F B, et al. (2008) Epidermal growth factor-induced enhancement of glioblastoma cell migration in 3D arises from an intrinsic increase in speed but an extrinsic matrix- and proteolysis-dependent increase in persistence. Mol Biol Cell 19: 4249-4259.
64. Gertler F B, Niebuhr K, Reinhard M, Wehland J, Soriano P (1996) Mena, a relative of VASP and Drosophila Enabled, is implicated in the control of microfilament dynamics. Cell 87: 227-239.
65. Philippar U, Roussos E T, Oser M, Yamaguchi H, Kim H D, et al. (2008) A Mena invasion isoform potentiates EGF-induced carcinoma cell invasion and metastasis. Dev Cell 15: 813-828.
66. Bear J E, Loureiro J J, Libova I, Fassler R, Wehland J, et al. (2000) Negative regulation of fibroblast motility by Ena/VASP proteins. Cell 101: 717-728.
67. Li H, Ruan J, Durbin R (2008) Mapping short DNA sequencing reads and calling variants using mapping quality scores. Genome research 18: 1851.
68. Thierry-Mieg D, Thierry-Mieg J (2006) AceView: a comprehensive cDNA-supported gene and transcripts annotation. Genome Biology 7: S12.
69. Pruitt K, Tatusova T, Maglott D (2006) NCBI reference sequences (RefSeq): a curated non-redundant sequence database of genomes, transcripts and proteins. Nucleic acids research.
70. Benjamini Y, Hochberg Y (1995) Controlling the false discovery rate: a practical and powerful approach to multiple testing. Journal of the Royal Statistical Society Series B (Methodological): 289-300.
71. Robinson M D, Oshlack A A scaling normalization method for differential expression analysis of RNA-seq data. Genome Biol 11: R25.
72. Mortazavi A, Williams B, McCue K, Schaeffer L, Wold B (2008) Mapping and quantifying mammalian transcriptomes by RNA-Seq. Nature methods 5: 621-628.
73. Audic S, Claverie J (1997) The significance of digital gene expression profiles. Genome research 7: 986.
74. Wang E, Sandberg R, Luo S, Khrebtukova I, Zhang L, et al. (2008) Alternative isoform regulation in human tissue transcriptomes. Nature 456: 470-476.
75. Xue Y, Zhou Y, Wu T, Zhu T, Ji X, et al. (2009) Genome-wide Analysis of PTB-RNA Interactions Reveals a Strategy Used by the General Splicing Repressor to Modulate Exon Inclusion or Skipping. Molecular cell 36: 996-1006.
76. Sanford J, Wang X, Mort M, VanDuyn N, Cooper D, et al. (2009) Splicing factor SFRS1 recognizes a functionally diverse landscape of RNA transcripts. Genome research 19: 381.
77. Yeo G, Coufal N, Liang T, Peng G, Fu X, et al. (2009) An RNA code for the FOX2 splicing regulator revealed by mapping RNA-protein interactions in stem cells. Nature structural & molecular biology 16: 130.
78. Warzecha C C, Jiang P, Amirikian K, Dittmar K A, Lu H, et al. An ESRP-regulated splicing programme is abrogated during the epithelial-mesenchymal transition. Embo J.
79. Da Wei Huang B, Lempicki R (2008) Systematic and integrative analysis of large gene lists using DAVID bioinformatics resources.

80. Dennis Jr G, Sherman B, Hosack D, Yang J, Gao W, et al. (2003) DAVID: database for annotation, visualization, and integrated discovery. Genome Biol 4: P3.
81. Riaz M, Elstrodt F, Hollestelle A, Dehghan A, Klijn J G, et al. (2009) Low-risk susceptibility alleles in 40 human breast cancer cell lines. BMC Cancer 9: 236.
82. Blick T, Widodo E, Hugo H, Waltham M, Lenburg M E, et al. (2008) Epithelial mesenchymal transition traits in human breast cancer cell lines. Clin Exp Metastasis 25: 629-642.
83. de Hoon M, Imoto S, Nolan J, Miyano S (2004) Open source clustering software. Bioinformatics 20: 1453-1454.
84. Saldanha A (2004) Java Treeview—extensible visualization of microarray data. Bioinformatics 20: 3246.

What is claimed is:

1. A method for identifying the proportion of alternatively spliced mRNA isoforms or expression products in a gene set relative to the total mRNA isoforms or expression products in the set in a tumor from a subject, comprising:
treating a sample of the tumor obtained from the subject so as to permit a determination of mRNA levels or determination of gene expression product levels in the sample; detecting (1) the proportion of alternatively spliced mRNA isoforms of one of the following sets of human genes relative to the total mRNA isoforms of the following human genes in the sample or (2) the proportion of alternatively spliced gene expression products of one of the following sets of human genes relative to the total gene expression products of the following human genes in the sample:
(a) CD44, NUMB, FAM62B, SLK, ENAH, H2AFY, and OSBPL8;
(b) SCRIB, CLSTN1, MLPH, TXNDC14 and CTNND1;
(c) SCRIB, CLSTN1, MLPH, and TXNDC14; or
(d) SCRIB, CLSTN1, MLPH, and CTNND1, wherein the alternatively spliced mRNA isoforms are detected by (1) contacting the mRNA with a labeled nucleic acid that hybridizes under high stringency conditions to the isoform mRNA or cDNA or (2) by contacting the gene expression products with an antibody that binds specifically to an isoform gene expression product, measuring the amount of labeled nucleic acid hybridization or amount of protein-antibody complex formed, and determining the proportion of alternatively spliced mRNA isoforms or expression products in the gene set relative to the total mRNA isoforms or expression products in the set in the tumor.

2. The method of claim 1, wherein the sample is a breast cancer sample.

3. The method of claim 2, wherein the tumor is an invasive duct carcinoma.

4. The method of claim 3, wherein the sample is obtained by fine needle aspiration.

5. The method of claim 1, wherein the alternatively spliced mRNA isoforms or alternatively spliced gene expression products result from a skipped exon, a mutually exclusive exon, a retained intron, an alternative 5' splice site, an alternative 3' splice site, an alternative 3' UTR, an alternative first exon, and/or an alternative last exon.

6. The method of claim 1, wherein detecting the alternatively spliced mRNA isoforms is effected indirectly by isolating mRNA from the sample and subjecting it to a reverse transcriptase polymerase chain reaction so as to produce cDNAs corresponding to the alternatively spliced mRNA isoforms and then quantitating the cDNA corresponding to the alternatively spliced mRNA isoforms.

7. The method of claim 1, wherein detecting the alternatively spliced gene expression products is effected indirectly by isolating alternatively spliced gene expression products corresponding to the alternatively spliced mRNA isoforms and then quantitating the alternatively spliced gene expression products corresponding to the alternatively spliced mRNA isoforms.

8. The method of claim 1 wherein the detecting the levels of alternatively spliced mRNA isoforms is effected using an exon microarray.

9. A method for identifying the proportion of alternatively spliced mRNA isoforms or expression products in a gene set relative to the total mRNA isoforms or expression products in the set in a tumor from a subject, comprising:

treating a sample of the tumor obtained from the subject so as to permit determination of mRNA levels or gene expression product levels in the sample;

detecting (1) the proportion of alternatively spliced mRNA isoforms of one of the following sets of human genes relative to the total mRNA isoforms of the following human genes in the sample or (2) the proportion of alternatively spliced gene expression products of one of the sets of following human genes relative to the total gene expression products of the following human genes in the sample:

(a) CD44, NUMB, FAM62B, SLK, ENAH, H2AFY, OSBPL8, C17orf61/PLSCR3, STARD10/CENTD2, MAP3K7, BMP1, and BTG3;

(b) YWHAB, ILF3, PAM, SCRIB, CLSTN1, MLPH, TXNDC14 and CTNND1;

(c) YWHAB, ILF3, PAM, SCRIB, CLSTN1, MLPH, and TXNDC14; or (d) YWHAB, ILF3, PAM, SCRIB, CLSTN1, MLPH, and CTNND1; wherein the alternatively spliced mRNA isoforms are detected by (1) contacting the mRNA with a labeled nucleic acid that hybridizes under high stringency conditions to an isoform mRNA or cDNA or (2) by contacting the gene expression products with an antibody that binds specifically to an isoform gene expression product, and detecting the amount bound;

measuring the amount of labeled nucleic acid hybridization or amount of protein-antibody complex formed, and determining the proportion of alternatively spliced mRNA isoforms or expression products in the gene set relative to the total mRNA isoforms or expression products in the set in the tumor.

10. A method for identifying the proportion of alternatively spliced mRNA isoforms or expression products in a gene set relative to the total mRNA isoforms or expression products in the set in a tumor from a subject, comprising:

treating a sample of the tumor obtained from the subject so as to permit determination of mRNA levels or gene expression product levels in the sample;

detecting (1) the proportion of alternatively spliced mRNA isoforms of one of the sets of the following human genes relative to the total mRNA isoforms of the following human genes in the sample or (2) the proportion of alternatively spliced gene expression products of one of the sets of the following human genes relative to the total gene expression products of the following human genes in the sample:

(a) ENAH, SLC37A2, MBNL1 and FLNB;

(b) MLPH and ARHGEF11; or (c) ENAH, SLC37A2, MBNL1, FLNB, MLPH and ARHGEF11;

wherein the alternatively spliced mRNA isoforms are detected by (1) contacting the mRNA with a labeled nucleic acid that hybridizes under high stringency conditions to an isoform mRNA or cDNA or (2) by contacting the gene expression products with an antibody that binds specifically to an isoform gene expression product, and detecting the amount bound;

measuring the amount of labeled nucleic acid hybridization or amount of protein-antibody complex formed, and determining the proportion of alternatively spliced mRNA isoforms or expression products in the gene set relative to the total mRNA isoforms or expression products in the set in the tumor.

* * * * *

SEQUENCE LISTING

```
<160> NUMBER OF SEQ ID NOS: 116

<210> SEQ ID NO 1
<211> LENGTH: 23
<212> TYPE: DNA
<213> ORGANISM: Artificial Sequence
<220> FEATURE:
<223> OTHER INFORMATION: primer directed to human GADPH

<400> SEQUENCE: 1
catgagaagt atgacaacag cct                                                 23

<210> SEQ ID NO 2
<211> LENGTH: 22
<212> TYPE: DNA
<213> ORGANISM: ARTIFICIAL SEQUENCE
<220> FEATURE:
<223> OTHER INFORMATION: PRIMER DIRECTED TO HUMAN GADPH

<400> SEQUENCE: 2
agtccttcca cgataccaaa gt                                                  22

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN ENAH

<400> SEQUENCE: 3
caacaagaaa accttgggaa a                                                   21

<210> SEQ ID NO 4
<211> LENGTH: 23
<212> TYPE: DNA
<213> ORGANISM: ARTIFICIAL SEQUENCE
<220> FEATURE:
<223> OTHER INFORMATION: PRIMER DIRECTED TO HUMAN ENAH

<400> SEQUENCE: 4
ggacctgttg tcaaaaacaa tct                                                 23

<210> SEQ ID NO 5
<211> LENGTH: 23
<212> TYPE: DNA
<213> ORGANISM: ARTIFICIAL SEQUENCE
<220> FEATURE:
<223> OTHER INFORMATION: PRIMER DIRECTED TO HUMAN ENAH

<400> SEQUENCE: 5
gaacaaaaag aggacaaagg tga                                                 23

<210> SEQ ID NO 6
<211> LENGTH: 24
<212> TYPE: DNA
```

```
<213> ORGANISM: ARTIFICIAL SEQUENCE
<220> FEATURE:
<223> OTHER INFORMATION: PRIMER DIRECTED TO HUMAN ENAH

<400> SEQUENCE: 6
tgccattcat tgtatttgtt cttt                                          24

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SLC37A2

<400> SEQUENCE: 7
ggtcctaacc caccagtgat                                               20

<210> SEQ ID NO 8
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN SLC32A7

<400> SEQUENCE: 8
actgggaccc tccatgct                                                 18

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SLC32A7

<400> SEQUENCE: 9
gggctgagtt gtgtctccat                                               20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SLC32A7

<400> SEQUENCE: 10
gagagatgcc cattttccag                                               20

<210> SEQ ID NO 11
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MBNL1

<400> SEQUENCE: 11
ctcagtcggc tgtcaaatca                                               20

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MBNL1

<400> SEQUENCE: 12
agagcaggcc tctttggtaa                                               20
```

<210> SEQ ID NO 13
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MBNL1

<400> SEQUENCE: 13
ttcatccacc cccacattta                                             20

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  MBNL1

<400> SEQUENCE: 14
ttggctagtt gcatttgctg                                             20

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FLNB

<400> SEQUENCE: 15
tgtgatctat gtgcgcttcg                                             20

<210> SEQ ID NO 16
<211> LENGTH: 19
<212> TYPE: DNA
<213> ORGANISM: ARTIFICIAL SEQUENCE
<220> FEATURE:
<223> OTHER INFORMATION: PRIMER DIRECTED TO HUMAN FLNB

<400> SEQUENCE: 16
catttaccgg tgcctcctc                                              19

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FLNB

<400> SEQUENCE: 17
atcgcctcca ctgtgaaaac                                             20

<210> SEQ ID NO 18
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN FLNB

<400> SEQUENCE: 18
agtgccatct ggggtcag                                               18

<210> SEQ ID NO 19
<211> LENGTH: 20
<212> TYPE: DNA
<213> ORGANISM: ARTIFICIAL SEQUENCE
<220> FEATURE:

<223> OTHER INFORMATION: PRIMER DIRECTED TO HUMAN ARHGEF11

<400> SEQUENCE: 19
tggcatgctg acataaaagc                                        20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ARHGEF11

<400> SEQUENCE: 20
ggttgtccct gcactaccag                                        20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ARHGEF11

<400> SEQUENCE: 21
tgacagaagg tgtgggtgtc                                        20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ARHGEF11

<400> SEQUENCE: 22
aacctgcgac atctgatcct                                        20

<210> SEQ ID NO 23
<211> LENGTH: 18
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 23
gatggcctcc caccattc                                          18

<210> SEQ ID NO 24
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 24
caggtaggtc agcaggcatt                                        20

<210> SEQ ID NO 25
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 25
aggaagctgg aggagctgac                                        20

```
<210> SEQ ID NO 26
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 26
cccaactgat ttgtccctgt                                          20

<210> SEQ ID NO 27
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN KIF13A

<400> SEQUENCE: 27
cagggttatg tgcctgaggt                                          20

<210> SEQ ID NO 28
<211> LENGTH: 20
<212> TYPE: DNA
<213> ORGANISM: ARTIFICIAL SEQUENCE
<220> FEATURE:
<223> OTHER INFORMATION: PIMER DIRECTED TO HUMAN KIF13A

<400> SEQUENCE: 28 caagcccta atgcctgtaa                                           20

<210> SEQ ID NO 29
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN KIF13A

<400> SEQUENCE: 29
agaagggacc accatgtcag                                          20

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN KIF13A

<400> SEQUENCE: 30
ctcacgggtc ttggagaaag                                          20

<210> SEQ ID NO 31
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN PLOD2

<400> SEQUENCE: 31
gcagtggata atagccttcc a                                        21

<210> SEQ ID NO 32
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLOD2
```

```
<400> SEQUENCE: 32 gactcccta ctccggaaac                                              20

<210> SEQ ID NO 33
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLOD2

<400> SEQUENCE: 33
ctagcatttc ggcaaagagc                                             20

<210> SEQ ID NO 34
<211> LENGTH: 27
<212> TYPE: DNA
<213> ORGANISM: ARTIFICIAL SEQUENCE
<220> FEATURE:
<223> OTHER INFORMATION: PRIMER DIRECTED TO HUMAN PLOD2

<400> SEQUENCE: 34
tgtacttaat taaggaaag acactcc                                      27

<210> SEQ ID NO 35
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 35
aaggctgtcg aaccctgta                                              20

<210> SEQ ID NO 36
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 36
gaggctgtgg aatgtgaggt                                             20

<210> SEQ ID NO 37
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 37
gtcaagccag ggaacttcaa                                             20

<210> SEQ ID NO 38
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 38
tttcctgagg gccatttta                                              20

<210> SEQ ID NO 39
<211> LENGTH: 20
```

```
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 39
caccttctta tccgcgagtt                                              20

<210> SEQ ID NO 40
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 40
aactgagcct gtgactgtgg                                              20

<210> SEQ ID NO 41
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 41
gagcgggtaa tcctcagtca                                              20

<210> SEQ ID NO 42
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 42
aatggcacca ctacgtcctc                                              20

<210> SEQ ID NO 43
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SLC37A2

<400> SEQUENCE: 43
ctagcctgct tgctcctttg                                              20

<210> SEQ ID NO 44
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN SLC37A2

<400> SEQUENCE: 44
tggaagtttc cattgtcttg c                                            21

<210> SEQ ID NO 45
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CUGBP1

<400> SEQUENCE: 45
```
agagttcccg caagtcctttﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠ 20

<210> SEQ ID NO 46
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN CUGBP1

<400> SEQUENCE: 46
tcaaagttcc ctgtgttgtg aﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠ 21

<210> SEQ ID NO 47
<211> LENGTH: 26
<212> TYPE: DNA
<213> ORGANISM: ARTIFICIAL SEQUENCE
<220> FEATURE:
<223> OTHER INFORMATION: PRIMER DIRECTED TO HUMAN ENAH

<400> SEQUENCE: 47
ggtgaagatt cagagcctgt aacttcﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠ 26

<210> SEQ ID NO 48
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN ENAH

<400> SEQUENCE: 48
cactgggctg tgataagggt gﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠ 21

<210> SEQ ID NO 49
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MBNL1

<400> SEQUENCE: 49
catttgcaag ccaagatcaaﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠﾠ 20

<210> SEQ ID NO 50
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MBNL1

<400> SEQUENCE: 50
tgggggaagt acagcttgag 20

<210> SEQ ID NO 51
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FLNB

<400> SEQUENCE: 51
tcctaacagc cccttcactg 20

<210> SEQ ID NO 52
<211> LENGTH: 20
<212> TYPE: DNA
<213> ORGANISM: ARTIFICIAL SEQUENCE

```
<220> FEATURE:
<223> OTHER INFORMATION: PRIMER DIRECTED TO HUMAN FLNB

<400> SEQUENCE: 52
ttcctgacag caaacggaat                                               20

<210> SEQ ID NO 53
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN KIF13A

<400> SEQUENCE: 53
gttctccaag ctggcattgt                                               20

<210> SEQ ID NO 54
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN KIF13A

<400> SEQUENCE: 54
ggcctcttct aagccaggag                                               20

<210> SEQ ID NO 55
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MICAL3

<400> SEQUENCE: 55
ggtcagcttg gcattcagtt                                               20

<210> SEQ ID NO 56
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MICAL3

<400> SEQUENCE: 56
agctgagctt ctccgaggac                                               20

<210> SEQ ID NO 57
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MICAL3

<400> SEQUENCE: 57
gctgcctccc cttctatctc                                               20

<210> SEQ ID NO 58
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MICAL3

<400> SEQUENCE: 58
acgaggagga ggaagagtcc                                               20
```

<210> SEQ ID NO 59
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PACSIN3

<400> SEQUENCE: 59
cttagctgct gctggcttct                                               20

<210> SEQ ID NO 60
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PACSIN3

<400> SEQUENCE: 60
acctcaccca aagcctcact                                               20

<210> SEQ ID NO 61
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN EPB41L1

<400> SEQUENCE: 61
agctggtgtg gacagaggag                                               20

<210> SEQ ID NO 62
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN EPB41L1

<400> SEQUENCE: 62
cggcctcact gtagtccttc                                               20

<210> SEQ ID NO 63
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ARHGEF11

<400> SEQUENCE: 63
tggcatgctg acataaaagc                                               20

<210> SEQ ID NO 64
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ARHGEF11

<400> SEQUENCE: 64
agaggcagca ggaggttaca                                               20

<210> SEQ ID NO 65
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 65
gccctgaaga gatgcacagt                                           20

<210> SEQ ID NO 66
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLEKHA1

<400> SEQUENCE: 66
gaggctgtgg aatgtgaggt                                           20

<210> SEQ ID NO 67
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 67
tcggaaaaac tgggtcatgt                                           20

<210> SEQ ID NO 68
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CLSTN1

<400> SEQUENCE: 68
aatggcacca ctacgtcctc                                           20

<210> SEQ ID NO 69
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLOD2

<400> SEQUENCE: 69
caaaaatctg ccagaggtca                                           20

<210> SEQ ID NO 70
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PLOD2

<400> SEQUENCE: 70
gatatggctc tttgccgaaa                                           20

<210> SEQ ID NO 71
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 71
agtacttggc cgatgtggac                                           20

<210> SEQ ID NO 72

```
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN MLPH

<400> SEQUENCE: 72
ctcagggcct cctcctctac                                              20

<210> SEQ ID NO 73
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SNX14

<400> SEQUENCE: 73
gcaacatagc tccctccatt                                              20

<210> SEQ ID NO 74
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SNX14

<400> SEQUENCE: 74
aatcaccaac acgcaattca                                              20

<210> SEQ ID NO 75
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PPFIBP1

<400> SEQUENCE: 75
cggcactcga aaagtcagat                                              20

<210> SEQ ID NO 76
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN PPFIBP1

<400> SEQUENCE: 76
ccagccagat ctaggtgctc                                              20

<210> SEQ ID NO 77
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FAT

<400> SEQUENCE: 77
tgtatgtccg gcagaggaac                                              20

<210> SEQ ID NO 78
<211> LENGTH: 20
<212> TYPE: DNA
<213> ORGANISM: ARTIFICIAL SEQUENCE
<220> FEATURE:
<223> OTHER INFORMATION: HUMAN PRIMER DIRECTED TO HUMAN FAT

<400> SEQUENCE: 78
```

```
ggaaagcctg tctgaagtgc                                              20

<210> SEQ ID NO 79
<211> LENGTH: 20
<212> TYPE: DNA
<213> ORGANIS: ARTIFICIAL SEQUENCE
<220> FEATURE:
<223> OTHER INFORMATION: PRIMER DIRECTED TO HUMAN NEK1

<400> SEQUENCE: 79
taatctgttg gcgctcattg                                              20

<210> SEQ ID NO 80
<211> LENGTH: 20
<212> TYPE: DNA
<213> ORGANISM: ARTIFICIAL SEQUENCE
<220> FEATURE:
<223> OTHER INFORMATION: HUMAN PRIMER DIRECTED TO HUMAN NEK1

<400> SEQUENCE: 80
aaacgggaag ctatgcagaa                                              20

<210> SEQ ID NO 81
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  NFYA1

<400> SEQUENCE: 81
ggatctccag agtggacagg                                              20

<210> SEQ ID NO 82
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  NFYA1

<400> SEQUENCE: 82
tccactgacc tgcaccatta                                              20

<210> SEQ ID NO 83
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ROBO1

<400> SEQUENCE: 83
ttcgcctcct ctctggtaag                                              20

<210> SEQ ID NO 84
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ROBO1

<400> SEQUENCE: 84
accctgtgtc acctgaggac                                              20

<210> SEQ ID NO 85
<211> LENGTH: 20
<212> TYPE: DNA
```

```
<213> ORGANISM: ARTIFICIAL SEQUENCE
<220> FEATURE:
<223> OTHER INFORMATION: PRIMER DIRECTED TO HUMAN DTNB

<400> SEQUENCE: 85
tgtatgtggt gaccctgtgg                                               20

<210> SEQ ID NO 86
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN DTNB

<400> SEQUENCE: 86
aggaaggatg aactggagca                                               20

<210> SEQ ID NO 87
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN STX2

<400> SEQUENCE: 87
tccaaggatc acaagcaaaa                                               20

<210> SEQ ID NO 88
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN STX2

<400> SEQUENCE: 88
atcagagcaa ggcaagaagg                                               20

<210> SEQ ID NO 89
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CSNK1G3

<400> SEQUENCE: 89
gttcaaatgc acccatcaca                                               20

<210> SEQ ID NO 90
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CSNK1G3

<400> SEQUENCE: 90
ccccaggatc tgtctgtgtc                                               20

<210> SEQ ID NO 91
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TEAD1

<400> SEQUENCE: 91
cttgccagaa ggaaatctcg                                               20
```

<210> SEQ ID NO 92
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TEAD1

<400> SEQUENCE: 92
cagccccagc ttgttatgaa					20

<210> SEQ ID NO 93
<211> LENGTH: 20
<212> TYPE: DNA
<213> ORGANISM: ARTIFICIAL SEQUENCE
<220> FEATURE:
<223> OTHER INFORMATION: PRIMER DIRCETED TO HUMAN VDP

<400> SEQUENCE: 93
gaaaatgcca cccagaaaga					20

<210> SEQ ID NO 94
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN VDP

<400> SEQUENCE: 94
tgcaatggga caattgctta					20

<210> SEQ ID NO 95
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ATP5C1

<400> SEQUENCE: 95
gccaagctgt catcacaaaa					20

<210> SEQ ID NO 96
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ATP5C1

<400> SEQUENCE: 96
ggacaaaggc agcagtaagc					20

<210> SEQ ID NO 97
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN TSC2

<400> SEQUENCE: 97
cggtccaatg tcctcttgtc					20

<210> SEQ ID NO 98
<211> LENGTH: 19
<212> TYPE: DNA
<213> ORGANISM: ARTIFICIAL SEQUENCE
<220> FEATURE:

```
<223> OTHER INFORMATION: PRIMER DIRECTED TO HUMAN TSC2

<400> SEQUENCE: 98
cactggtgag ggacgtctg                                                19

<210> SEQ ID NO 99
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ASLX1

<400> SEQUENCE: 99
gcctcgagtt gtcctgactc                                               20

<210> SEQ ID NO 100
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN ASLX1

<400> SEQUENCE: 100
tctgttgcgc ttcatttgac                                               20

<210> SEQ ID NO 101
<211> LENGTH: 24
<212> TYPE: DNA
<213> ORGANISM: ARTIFICIAL SEQUENCE
<220> FEATURE:
<223> OTHER INFORMATION: PRIMER DIRECTED TO HUMAN APLP2

<400> SEQUENCE: 101
catgtcagac aaggaaatta ctca                                          24

<210> SEQ ID NO 102
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN APLP2

<400> SEQUENCE: 102
atcattggtt ggcagaggag                                               20

<210> SEQ ID NO 103
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CENTD3

<400> SEQUENCE: 103
tcctcgtaca caggctcctc                                               20

<210> SEQ ID NO 104
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN CENTD3

<400> SEQUENCE: 104
tatgcctttg ctgcctatcc                                               20
```

```
<210> SEQ ID NO 105
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FGFR2

<400> SEQUENCE: 105
caggtagtct ggggaagctg                                              20

<210> SEQ ID NO 106
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN FGFR2

<400> SEQUENCE: 106
gcagaagtgc tggctctgtt                                              20

<210> SEQ ID NO 107
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  FGFR2

<400> SEQUENCE: 107
caccacggac aaagagattg                                              20

<210> SEQ ID NO 108
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  FGFR1

<400> SEQUENCE: 108
gcccctgtgc aatagatgat                                              20

<210> SEQ ID NO 109
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  FGFR1

<400> SEQUENCE: 109
aatgtgacag aggcccagag                                              20

<210> SEQ ID NO 110
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN  FGFR1

<400> SEQUENCE: 110
accaccgaca aagagatgga                                              20

<210> SEQ ID NO 111
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN DOCK9
```

-continued

<400> SEQUENCE: 111
tcaggcaaac ctcagtagca                                                20

<210> SEQ ID NO 112
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN DOCK9

<400> SEQUENCE: 112
acattgcctg tttcccgtaa                                                20

<210> SEQ ID NO 113
<211> LENGTH: 22
<212> TYPE: DNA
<213> ORGANISM: ARTIFICIAL SEQUENCE
<220> FEATURE:
<223> OTHER INFORMATION: PRIMER DIRECTED TO HUMAN DOCK9

<400> SEQUENCE: 113
tcaagtgtgc ttggaatttc tg                                             22

<210> SEQ ID NO 114
<211> LENGTH: 22
<212> TYPE: DNA
<213> ORGANISM: ARTIFICIAL SEQUENCE
<220> FEATURE:
<223> OTHER INFORMATION: PRIMER DIRECTED TO HUMAN SEPTIN-2

<400> SEQUENCE: 114
caaggcgaag attctcatta cc                                             22

<210> SEQ ID NO 115
<211> LENGTH: 20
<212> TYPE: DNA
<213> ORGANISM: ARTIFICIAL SEQUENCE
<220> FEATURE:
<223> OTHER INFORMATION: PRIMER DIRECTED TO HUMAN SEPTIN-2

<400> SEQUENCE: 115
gctgccaaat gagttttggt                                                20

<210> SEQ ID NO 116
<211> LENGTH: 21
<212> TYPE: DNA
<213> ORGANISM: ARTIFICIAL SEQUENCE
<220> FEATURE:
<223> OTHER INFORMATION: PRIMER DIRECTED TO HUMAN SEPTIN-2

<400> SEQUENCE: 116
ccttggacaa gaccaaagtc a                                              21